United States Patent
Ergüden et al.

(10) Patent No.: US 6,936,609 B2
(45) Date of Patent: Aug. 30, 2005

(54) IMIDAZOTRIAZINES FOR USE AS PHOSPHODIESTERASE INHIBITORS

(75) Inventors: Jens-Kerim Ergüden, Wulfrath (DE); Marcus Bauser, Wuppertal (DE); Nils Burkhardt, Velbert (DE); Dietmar Flubacher, Freiburg (DE); Arno Friedl, Bergisch Gladbach (DE); Irene Gerlach, Cologne (DE); Volker Hinz, Cologne (DE); Reinhard Jork, Haan (DE); Paul Naab, Wuppertal (DE); Ulrich Niewöhner, deceased, late of Wermelskirchen (DE); Maria Theresia Niewöhner, legal representative, Wermelskirchen (DE); Thorsten Oliver Repp, Wesseling (DE); Karl-Heinz Schlemmer, Wuppertal (DE); Jürgen Stoltefuss, Haan (DE); David Brückner, Essen (DE); Martin Hendrix, Cologne (DE); Dagmar Schauss, Solingen (DE); Adrian Tersteegen, Velbert (DE)

(73) Assignee: Bayer HealthCare AG, Leverkusen (DE)

( * ) Notice: Subject to any disclaimer, the term of this patent is extended or adjusted under 35 U.S.C. 154(b) by 22 days.

(21) Appl. No.: 10/481,281

(22) PCT Filed: Jun. 10, 2002

(86) PCT No.: PCT/EP02/06322

§ 371 (c)(1),
(2), (4) Date: Jun. 25, 2004

(87) PCT Pub. No.: WO03/000693

PCT Pub. Date: Jan. 3, 2003

(65) Prior Publication Data

US 2004/0249148 A1 Dec. 9, 2004

(30) Foreign Application Priority Data

Jun. 22, 2001 (DE) .......................... 101 30 167

(51) Int. Cl.[7] .................. C07D 487/04; A61K 31/53; A61K 31/415; A61P 25/28

(52) U.S. Cl. ........................................ 514/243; 544/184
(58) Field of Search ........................ 544/184; 514/243

(56) References Cited

U.S. PATENT DOCUMENTS 3,941,785 A    3/1976   Clarke et al. ............ 260/249.5

FOREIGN PATENT DOCUMENTS

| DE | 2811780 | 9/1978 |
| WO | 9924433 | 5/1999 |
| WO | 0124781 | 4/2001 |

OTHER PUBLICATIONS

West, Anthony R., Solid State Chemistry and its Applications, Wiley, New York, 1988, pp. 358 & 365.*
Lucas et al. Pharmacological Reviews 52 (3), 375–413, 2000.*
Beavo, J. A., "Cyclic Nucleotide Phosphodiesterases: Functional Implications of Multiple Isoforms", Pharmacological Reviews, 75(4): 725–748 (Oct. 1995).
Beavo, J. A, Conti, M., and Heaslip, R. J., "Multiple Cyclic Nucleotide Phosphodiesterases", Molecular Pharmacology, 46(3): 399–405 (Sep. 1994).
Charles, I., Latham, D. W. S., Hartley, D., Oxford, A. W., and Scopes, D. I. C., "Bicyclic Heterocycles with Nitrogen at the Ring Junction. Part 2. 1. Application of the Dakin–West Reaction to the Synthesis of Immidazo–[5,1–f]–1,2, 4–triazin–4–(3H)–ones", J. Chem. Soc., Perkin Trans. I, 5(1): 1139–1146 (May 1980).
Soderling, S. H., and Beavo, J. A., "Regulation of cAMP and cGMP Signaling: New Phosphodiesterases and New Functions", Current Opinion in Cell Biology, 12(2): 174–179 (Apr. 2000).

* cited by examiner

Primary Examiner—Venkataraman Balasubramanian
(74) Attorney, Agent, or Firm—Susan M. Pellegrino

(57) ABSTRACT

The invention relates to new imidazotriazines, processes for their preparation, and their use for the production of medicaments for the treatment and/or prophylaxis of neurodegenerative disorders, in particular Parkinson's disease.

7 Claims, No Drawings

IMIDAZOTRIAZINES FOR USE AS PHOSPHODIESTERASE INHIBITORS

The invention relates to new imidazotriazines, processes for their preparation, and their use for the production of medicaments for the treatment and/or prophylaxis of neurodegenerative disorders, in particular Parkinson's disease.

The cyclic nucleotides cGMP and cAMP belong to the most important intracellular messengers. Phosphodiesterases (PDEs) play an essential role in the regulation of the concentrations of cGMP and cAMP. Hitherto, 11 phosphodiesterase isoenzyme groups are known (PDE 1–7: Beavo et al. *Mol. Pharmacol.* 1994, 399–405; PDE 8–10: Soderling and Beavo *Curr. Opin. Cell Biol.* 2000, 12, 174–179; PDE 11: Fawcett et al. *Proc. Natl. Acad. Sci. U. S. A.* 2000, 97, 3702–3707).

The PDE 10A hydrolyses both cAMP and cGMP (Fujishige *J. Biol. Chem.* 1999, 274, 18438–18445). Transcribed PDE 10A was identified especially in the putamen and caudate nucleus regions of the brain and in thyroid and testicular tissue. In comparison to normal tissue, the PDE 10A mRNA is moreover expressed to an increased extent in certain tumour tissues, such as, for example, in tissues of breast, liver, colon and lung tumours.

The synthesis of 4-amino-2,5-diphenyl-7-methylthio-imidazo[5,1-f]-[1,2,4]triazines is known from *Synthesis* 1989, 843–847.

U.S. Pat. No. 3,941,785 describes 2-amino-imidazo[5,1-f]-[1,2,4]triazines as PDE inhibitors having spasmolytic action for the treatment of asthma, bronchitis, chronic heart failure and skin disorders.

The present invention relates to compounds of the general formula (I),

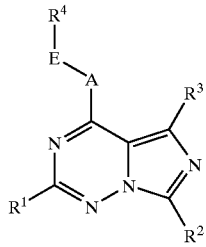

(I)

in which $R^1$ represents $(C_6–C_{10})$-aryl, which is optionally identically or differently substituted by radicals selected from the group consisting of halogen, formyl, carbamoyl, cyano, hydroxyl, trifluoromethyl, trifluoromethoxy, nitro, $(C_1–C_6)$-alkyl or $(C_1–C_6)$-alkoxy, and optionally by a radical of the formula $—SO_2NR^5R^6$, in which $R^5$ and $R^6$ independently of one another denote hydrogen or $(C_1–C_6)$-alkyl, or $NR^5R^6$ denotes 4- to 8-membered heterocyclyl, bonded via a nitrogen atom, optionally identically or differently substituted by radicals selected from the group consisting of oxo, halogen, $(C_1–C_6)$-alkyl and $(C_1–C_6)$-acyl, $R^2$ represents a saturated or partially unsaturated hydrocarbon radical having 1 to 10 carbon atoms, $R^3$ represents methyl or ethyl, A represents O, S or $NR^7$, where $R^7$ is hydrogen or $(C_1–C_6)$-alkyl optionally substituted by $(C_1–C_3)$-alkoxy, E represents a bond or $(C_1–C_3)$-alkanediyl, $R^4$ represents $(C_6–C_{10})$-aryl or 5- to 10-membered heteroaryl, where aryl and heteroaryl are optionally identically or differently substituted by radicals selected from the group consisting of halogen, formyl, carboxyl, carbamoyl, $—SO_3H$, aminosulphonyl, cyano, hydroxyl, trifluoromethyl, trifluoromethoxy, nitro, $(C_1–C_6)$-alkyl, $(C_1–C_6)$-alkoxy, 1,3-dioxa-propane-1,3-diyl, $(C_1–C_6)$-alkylthio, $(C_1–C_6)$-alkylsulphinyl and $(C_1–C_6)$-alkylsulphonyl, $—NR^8R^9$ and optionally methyl-substituted, 5- to 6-membered heteroaryl or phenyl, in which $R^8$ and $R^9$ independently of one another denote hydrogen, $(C_1–C_6)$-alkyl or $(C_1–C_6)$-acyl, and their salts, hydrates and/or solvates.

The compounds according to the invention can exist in stereoisomeric forms, which either behave as image and mirror image (enantiomers), or which do not behave as image and mirror image (diastereomers). The invention relates both to the enantiomers or diastereomers and to their respective mixtures. These mixtures of the enantiomers and diastereomers can be separated into the stereoisomerically uniform constituents in a manner known per se.

The compounds according to the invention can also be present in the form of their salts, hydrates and/or solvates.

Preferred salts in the context of the invention are physiologically acceptable salts of the compounds according to the invention.

Physiologically acceptable salts of the compounds according to the invention can be acid addition salts of the compounds with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which can also be mentioned, however, are salts with customary bases, such as, for example, alkali metal salts (e.g. sodium or potassium salts), alkaline earth metal salts (e.g. calcium or magnesium salts) or ammonium salts, derived from ammonia or organic amines such as, for example, diethylamine, triethylamine, ethyldiisopropylamine, procaine, dibenzylamine, N-methylmorpholine, dihydroabietylamine, 1-ephenamine or methyl-piperidine.

Hydrates of the compounds according to the invention are stoichiometric compositions of the compounds or their salts with water.

Solvates of the compounds according to the invention are stoichiometric compositions of the compounds or their salts with solvents.

In the context of the present invention, the substituents in general have the following meaning:

$(C_1–C_6)$-Acyl in the context of the invention represents a straight-chain or branched acyl radical having 1 to 6 carbon atoms. Examples which may be mentioned are: acetyl, ethylcarbonyl, propylcarbonyl, isopropylcarbonyl, butylcarbonyl, isobutylcarbonyl, pentylcarbonyl and hexylcarbonyl. A straight-chain or branched acyl radical having 1 to 4 carbon atoms is preferred. Acetyl and ethylcarbonyl are particularly preferred.

$(C_1–C_3)$-Alkanediyl in the context of the invention represents a straight-chain or branched alkanediyl radical having 1 to 3 carbon atoms. Examples which may be mentioned are methylene, ethylene, ethane-1,1-diyl, propylene, propane-1,2-diyl, propane-2,2-diyl. Methylene is preferred.

(C$_1$–C$_6$)-Alkoxy represents a straight-chain or branched alkoxy radical having 1 to 6 carbon atoms. A straight-chain or branched alkoxy radical having 1 to 4 carbon atoms is preferred. Examples which may be mentioned are: methoxy, ethoxy, n-propoxy, isopropoxy, tert-butoxy, n-pentoxy and n-hexoxy. A straight-chain or branched alkoxy radical having 1 to 3 carbon atoms is particularly preferred.

(C$_1$–C$_6$)-Alkyl represents a straight-chain or branched alkyl radical having 1 to 6 carbon atoms. A straight-chain or branched alkyl radical having 1 to 4 carbon atoms is preferred. Examples which may be mentioned are: methyl, ethyl, n-propyl, isopropyl, tert-butyl, n-pentyl and n-hexyl. A straight-chain or branched alkyl radical having 1 to 3 carbon atoms is particularly preferred.

(C$_1$–C$_6$)-Alklysulphinyl represents a straight-chain or branched aikylsulphinyl radical having 1 to 6 carbon atoms. A straight-chain or branched alkylsulphinyl radical having 1 to 4 carbon atoms is preferred. Examples which may be mentioned are: methylsulphinyl, ethylsulphinyl, n-propylsulphinyl, isopropylsulphinyl, tert-butylsulphinyl, n-pentylsulphinyl and n-hexylsulphinyl. A straight-chain or branched alkylsulphinyl radical having 1 to 3 carbon atoms is particularly preferred.

(C$_1$–C$_6$)-Alkylsulphonyl represents a straight-chain or branched alkylsulphonyl radical having 1 to 6 carbon atoms. A straight-chain or branched alkylsulphonyl radical having 1 to 4 carbon atoms is preferred. Examples which may be mentioned are: methylsulphonyl, ethylsulphonyl, n-propylsulphonyl, isopropylsulphonyl, tert-butylsulphonyl, n-pentylsulphonyl and n-hexylsulphonyl. A straight-chain or branched alkylsulphonyl radical having 1 to 3 carbon atoms is particularly preferred.

(C$_1$–C$_6$)-Alkylthio in the context of the invention represents a straight-chain or branched alkylthio radical having 1 to 6 carbon atoms. A straight-chain or branched alkylthio radical having 1 to 4 carbon atoms is preferred. Examples which may be mentioned are: methylthio, ethylthio, n-propylthio, isopropylthio, tert-butylthio, n-pentylthio and n-hexylthio. A straight-chain or branched alkylthio radical having 1 to 3 carbon atoms is particularly preferred.

(C$_6$–C$_{10}$)-Aryl in the context of the invention represents an aromatic radical having 6 to 10 carbon atoms. Preferred aryl radicals are phenyl and naphthyl.

Halogen in the context of the invention in general represents fluorine, chlorine, bromine and iodine. Fluorine, chlorine and bromine are preferred. Fluorine and chlorine are particularly preferred.

5- to 10-membered heteroaryl in the context of the invention in general represents an aromatic, mono- or bicyclic radical having 5 to 10 ring atoms and up to 5 hetero atoms from the series S, O and/or N. 5- to 6-membered heteroaryls having up to 4 heteroatoms are preferred. The heteroaryl radical can be bonded via a carbon atom or hetero atom. Examples which may be mentioned are: thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

4- to 8-membered heterocyclyl bonded via a nitrogen atom in the context of the invention in general represents a mono- or polycyclic, heterocyclic radical having 4 to 8 ring atoms and up to 3, preferably 2 hetero atoms or hetero groups from the series N, O, S, SO, SO$_2$, where at least one of the hetero atoms or hetero groups is a nitrogen atom. 5- to 7-membered heterocyclyl is preferred. Mono- or bicyclic heterocyclyl is preferred. Monocyclic heterocyclyl is particularly preferred. Preferred heteroatoms are O, N and S.

The heterocyclyl radicals can be saturated or partially unsaturated. Saturated heterocyclyl radicals are preferred. The heterocyclyl radicals can be bonded via a carbon atom or a heteroatom. 5- to 7-membered, monocyclic saturated heterocyclyl radicals having up to two hetero atoms from the series O, N and S are particularly preferred. Examples which may be mentioned are: pyrrolidin-2-yl, pyrrolidin-3-yl, pyrrolinyl, piperidinyl, morpholinyl, perhydroazepinyl.

A saturated or partially unsaturated hydrocarbon radical having 1 to 10 carbon atoms in the context of the invention represents a straight-chain or branched, cyclic or partially cyclic, non-aromatic, organic radical, which contains 1 to 10 carbon atoms, which can contain one or more double and/or triple bonds and which, depending on the degree of saturation and cyclization, is saturated with hydrogen atoms. Saturated organic radicals are preferred. The hydrocarbon radical can consist of a straight-chain or branched alkyl radical, where two geminal, vicinal or non-adjacent hydrogen atoms of the alkyl radical can in turn be replaced by a straight-chain or branched alkanediyl radical. Examples which may be mentioned are: straight-chain or branched (C$_1$–C$_{10}$)-alkyl, (C$_3$–C$_{10}$)-cycloalkyl and mono- or di-alkylcycloalkyl, cycloalkyl-alkyl, and also [(alkyl)cycloalkyl]alkyl containing a total of 3 to 10 carbon atoms. Examples which may be mentioned are: methyl, ethyl, vinyl, n-propyl, i-propyl, allyl, propargyl, butyl, pentyl, but-2-yl, n-hept-3-yl, cyclopropyl, 2-methyl-cycloprop-1-yl, cyclobutyl, cyclopentyl, cyclohexyl, 4,4-dimethyl-cyclohexane-1,1-diyl, 4-tert-butyl-cyclohexyl, 2-cyclohexyl-prop-1-yl.

When radicals in the compounds according to the invention are optionally substituted, if not specified otherwise, substitution with up to three identical or different substituents is preferred.

The compounds of the general formula (I) can also be present as tautomers, such as shown below by way of example for A=NH:

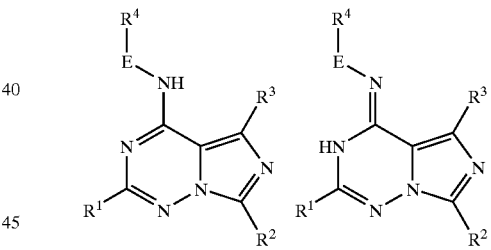

A further embodiment of the invention relates to compounds of the general formula (I),
in which
R$^1$ represents phenyl, which is optionally identically or differently mono- to disubstituted by radicals selected from the group consisting of fluorine, chlorine, methoxy, ethoxy or a radical of the formula —SO$_2$NR$^5$R$^6$,
where
NR$^5$R$^6$ is 5- to 7-membered heterocyclyl bonded via a nitrogen atom,
R$^2$ represents (C$_1$–C$_8$)-alkyl or (C$_3$–C$_8$)-cycloalkyl,
R$^3$ represents methyl or ethyl,
A represents O or NH,
E represents a bond,
R$^4$ represents phenyl, which is optionally identically or differently substituted by radicals selected from the group consisting of fluorine, chlorine, methoxy or ethoxy, and their salts, hydrates and/or solvates.

A further embodiment of the invention relates to compounds of the general formula (I), in which A represents O or NH, and
$R^1$, $R^2$, $R^3$, E and $R^4$ have the abovementioned meaning,
and their salts, hydrates and/or solvates.

A further embodiment of the invention relates to compounds of the general formula (I), in which E represents a bond, and
$R^1$, $R^2$, $R^3$, A and $R^4$ have the abovementioned meaning,
and their salts, hydrates and/or solvates.

A further embodiment of the invention relates to compounds of the general formula (I), in which $R^2$ represents $(C_1-C_8)$-alkyl or $(C_3-C_8)$-cycloalkyl, and
$R^1$, $R^3$, A, E and $R^4$ have the abovementioned meaning,
and their salts, hydrates and/or solvates.

A further embodiment of the invention relates to compounds of the general formula (I), in which $R^3$ represents methyl, and
$R^1$, $R^2$, A, E and $R^4$ have the abovementioned meaning,
and their salts, hydrates and/or solvates.

A further embodiment of the invention relates to compounds of the general formula (I), in which $R^4$ represents phenyl, which is mono- to trisubstituted by methoxy,
$R^1$, $R^2$, $R^3$, A and E have the abovementioned meaning,
and their salts, hydrates and/or solvates.

A further embodiment of the invention relates to compounds of the general formula (I), in which $R^4$ represents 3,4,5-trimethoxyphenyl, and
$R^1$, $R^2$, $R^3$, A and E have the abovementioned meaning,
and their salts, hydrates and/or solvates.

A further embodiment of the invention relates to compounds of the general formula (I), in which $R^4$ represents 3,4,5-trimethoxyphenyl,
A represents O or NH,
E represents a bond, and
$R^1$, $R^2$ and $R^3$ have the abovementioned meaning,
and their salts, hydrates and/or solvates.

A further embodiment of the invention relates to compounds of the general formula (I), in which $R^2$ represents $(C_1-C_8)$-alkyl or $(C_3-C_8)$-cycloalkyl,
$R^3$ represents methyl or ethyl,
$R^4$ represents 3,4,5-trimethoxyphenyl,
A represents O or NH,
E represents a bond, and
$R^1$ has the abovementioned meaning,
and their salts, hydrates and/or solvates.

The invention furthermore relates to processes for the preparation of the compounds of the formula (I).

In process
[A] compounds of the general formula (II),

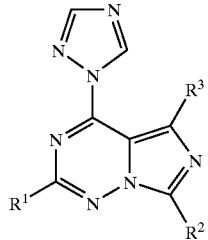

in which
$R^1$, $R^2$ and $R^3$ have the meaning indicated above,
are reacted with compounds of the general formula (III),

in which
$R^4$, A and E have the meaning indicated above,
to give compounds of the general formula (I),

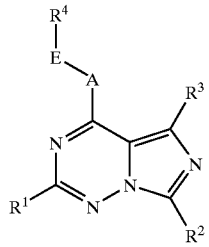

in which
$R^1$, $R^2$, $R^3$, $R^4$, A and E have the meaning indicated above,
in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, dimethylformamide, dimethylacetamide, 1,2-dimethoxyethane, dimethyl sulphoxide, acetonitrile or pyridine, preferred solvents are pyridine, glycol dimethyl ether, diethylene glycol dimethyl ether, tetrahydrofuran, dioxane or dimethyl sulphoxide, or without solvent in the form of a melt, optionally in the presence of a base, such as, for example, alkali metal hydroxides such as sodium or potassium hydroxide, or alkali metal carbonates such as caesium carbonate, sodium or potassium carbonate, or sodium or potassium methoxide, or sodium or potassium ethoxide or potassium tert-butoxide, or amides such as sodium amide, lithium bis-(trimethylsilyl)amide, lithium diisopropylamide, or organometallic compounds such as butyllithium or phenyllithium, or other bases such as sodium hydride, DBU, triethylamine or diisopropylethylamine, preferably sodium hydride, triethylamine, potassium tert-butoxide or DBU, optionally in the presence of auxiliary reagents, preferably potassium fluoride or dimethylaminopyridine, optionally in the presence of crown ethers, preferably 15-crown-5, 18-crown-8 or 12-crown-4, preferably in a temperature range from room temperature up to reflux of the solvents at normal pressure.

The compounds of the general formula (III) are known or can be synthesized from the appropriate starting materials according to known processes.

In process
[B] compounds of the general formula (IV),

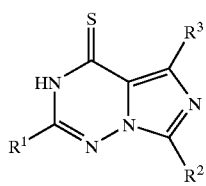

(IV)

in which $R^1$, $R^2$ and $R^3$ have the meaning indicated above, are reacted with compounds of the general formula (V),

(V)

in which $R^4$ and E have the meaning indicated above, and $X^1$ represents a leaving group, preferably mesylate, tosylate or halogen, particularly preferably bromine or iodine, to give compounds of the general formula (Ia),

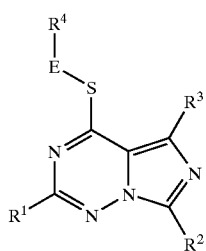

(Ia)

in which $R^1$, $R^2$, $R^3$, $R^4$ and E have the meaning indicated above, in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, dimethylformamide, dimethylacetamide, 1,2-dimethoxyethane, dimethyl sulphoxide, acetonitrile or pyridine, those preferred are dimethyl sulphoxide, dimethylformamide or tetrahydrofuran, optionally in the presence of a base, such as, for example, alkali metal carbonates such as caesium carbonate, sodium or potassium carbonate, or potassium tert-butoxide, or amides such as sodium amide, lithium bis-(trimethylsilyl)amide, lithium diisopropylamide, or organometallic compounds such as butyllithium or phenyllithium, or other bases such as sodium hydride, DBU, triethylamine or diisopropylethylamine, preferably triethylamine, sodium carbonate or sodium hydrogencarbonate, preferably in a temperature range from room temperature up to reflux of the solvents at normal pressure.

The compounds of the general formula (V) are known or can be synthesized from the appropriate starting materials according to known processes.

For the preparation of the compounds of the formula (II), compounds of the general formula (VI),

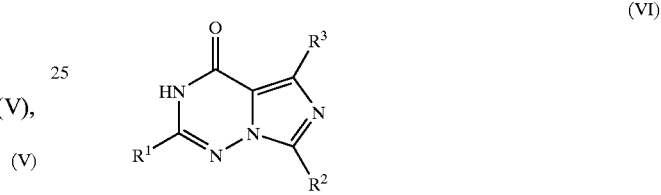

(VI)

in which $R^1$, $R^2$ and $R^3$ have the meaning indicated above, are reacted with 1,2,4-triazole in the presence of a chlorinating agent, preferably phosphorus oxychloride, phosphorus pentachloride, sulphuryl chloride and/or thionyl chloride, optionally in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, dimethylformamide, dimethylacetamide, 1,2-dimethoxyethane, dimethyl sulphoxide, acetonitrile, diethylphenylamine or pyridine, those preferred are pyridine, trichloromethane, diethylphenylamine, dioxane or acetonitrile, optionally in the presence of a base, such as for example alkali metal carbonates such as caesium carbonate, sodium or potassium carbonate, or other bases such as DBU, triethylamine, diethylphenylamine or diisopropylethylamine, those preferred are triethylamine, pyridine or diethylphenylamine, preferably in a temperature range from –20° C. to room temperature at normal pressure (cf. e.g. Knutsen et al. *J. Chem. Soc., Perkin Trans* 1, 1985, 621–630; A. Kraszewski, J. Stawinski, *Tetrahedron Lett.* 1980, 21, 2935).

For the preparation of the compounds of the formula (VIa),

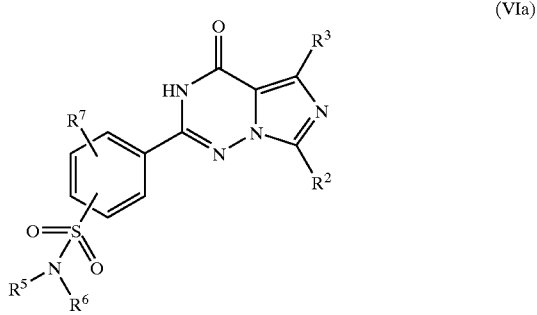

in which
R² and R³ have the meaning indicated above,
R⁵ and R⁶ independently of one another represent hydrogen or (C₁–C₆)-alkyl,
or
NR⁵R⁶ represents a 4- to 8-membered heterocyclyl bonded via a nitrogen atom, optionally identically or differently substituted by radicals selected from the group consisting of oxo, halogen, (C₁–C₆)-alkyl and (C₁–C₆)-acyl, and
R⁷ represents hydrogen, halogen, formyl, carbamoyl, cyano, hydroxyl, trifluoromethoxy, nitro, (C₁–C₆)-alkyl or (C₁–C₆)-alkoxy,
compounds of the general formula (VIb),

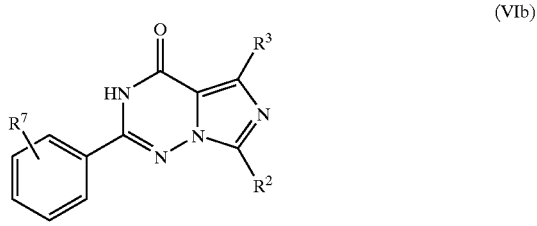

in which
R², R³ and R⁷ have the meaning indicated above,
are reacted in two stages, firstly with chlorosulphonic acid and subsequently with compounds of the formula (VII),

in which
R⁵ and R⁶ have the meaning indicated above.

The first stage is optionally carried out in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, dimethylacetamide, 1,2-dimethoxyethane, dimethyl sulphoxide, acetonitrile or pyridine, those preferred are methylene chloride, trichloromethane, tetrahydrofuran or 1,2-dichloroethane, preferably in a temperature range from −20° C. to room temperature at normal pressure.

The second stage is carried out in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, dimethylformamide, dimethylacetamide, 1,2-dimethoxyethane, dimethyl sulphoxide, acetonitrile or pyridine, those preferred are methylene chloride, trichloromethane, tetrahydrofuran or dimethylformamide, preferably in a temperature range from room temperature up to reflux of the solvents at normal pressure.

The compounds of the general formula (VII) are known or can be synthesized from the appropriate starting materials according to known processes.

For the preparation of the compounds of the formula (IV), compounds of the general formula (VI) are reacted with phosphorus pentasulphide, optionally in inert solvents; these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, 1,2-dimethoxyethane, dimethyl sulphoxide, acetonitrile or pyridine, pyridine is preferred, preferably in a temperature range from 50° C. up to reflux of the solvents at normal pressure. (cf. e.g. Knutsen et al. *J. Chem. Soc., Perkin Trans* 1, 1984, 229–238).

Optionally, this reaction is also carried out using Lawesson's reagent in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, 1,2-dimethoxyethane, dimethyl sulphoxide or pyridine, those preferred are toluene or xylene, preferably in a temperature range from 50° C. up to reflux of the solvents at normal pressure.

For the preparation of the compounds of the formula (VI), compounds of the general formula (VIII),

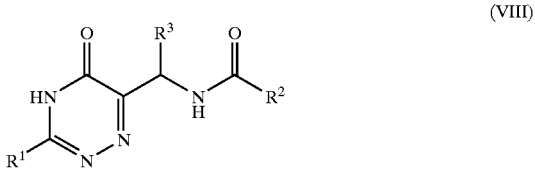

in which
R¹, R² and R³ have the meaning indicated above,
are reacted with suitable dehydrating reagents (e.g. Lewis acids), preferably phosphorus oxychloride, phosphorus pentoxide, polyphosphoric acid or methylsulphonyl chloride, optionally in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, dimethylacetamide, 1,2-dimethoxyethane, dimethyl sulphoxide, acetonitrile or pyridine, that preferred is 1,2-dichloroethane, preferably in a temperature range from 40° C. up to reflux of the solvents at normal pressure. (cf. for example Charles et al. *J. Chem. Soc., Perkin Trans* 1, 1980, 1139).

Compounds of the formula (VIb) are prepared from compounds of the formula (VIII),
in which
$R^1$ represents phenyl, which is optionally substituted by halogen, formyl, carbamoyl, cyano, hydroxyl, trifluoromethoxy, nitro, $(C_1–C_6)$-alkyl or $(C_1–C_6)$-alkoxy,
under the same conditions as compounds of the formula (VI) are prepared.

For the preparation of the compounds of the formula (VIII), compounds of the general formula (IX),

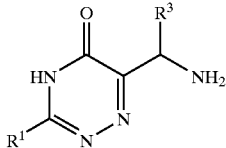

(IX)

or their salts, e.g. hydrochloride salts,
in which
$R^1$ and $R^3$ have the meaning indicated above,
are reacted with compounds of the general formula (X),

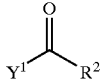

(X)

in which
$R^2$ has the meaning indicated above, and
$Y^1$ represents halogen, preferably bromine or chlorine, or hydroxyl,
in the case that $Y^1$ represents halogen,
in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, acetone, dimethylformamide, dimethylacetamide, 1,2-dimethoxyethane, 2-butanone, dimethyl sulphoxide, acetonitrile, pyridine or hexamethylphosphoramide, those preferred are tetrahydrofuran or methylene chloride, optionally in the presence of a base, such as, for example, alkali metal hydroxides such as sodium or potassium hydroxide, or alkali metal carbonates such as caesium carbonate, sodium or potassium carbonate, or amides such as lithium diisopropylamide, or other bases such as DBU, triethylamine or diisopropylethylamine, preferably triethylamine, preferably in a temperature range from 0° C. to 50° C. at normal pressure,
in the case that $Y^1$ represents hydroxyl,
in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, acetone, dimethylformamide, dimethylacetamide, 1,2-dimethoxyethane, dimethyl sulphoxide, acetonitrile or pyridine, those preferred are tetrahydrofuran, dimethylformamide or methylene chloride, in the presence of customary condensing agents, preferably carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetra-methyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyl-uronium hexafluorophosphate (HATU), or 1-hydroxybenzotriazole (HOBt), or benzotriazol-1-yloxytris (dimethylamino)-phosphonium hexafluorophosphate (BOP), or mixtures of these, optionally in the presence of a base, preferably alkali metal carbonates, for example sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine, the combination of N-(3-dimethylaminoisopropyl)-N'-ethylcarbodiimide hydrochloride (EDC) and 1-hydroxybenzotriazole (HOBt), and the combination of benzotriazol-1-yloxy-tris(dimethylamino) phosphonium hexafluorophosphate (BOP) and triethylamine, is particularly preferred, preferably in a temperature range from room temperature to 50° C. at normal pressure.

The compounds of the general formula (X) are known or can be synthesized from the appropriate starting materials according to known processes.

For the preparation of the compounds of the formula (IX), compounds of the general formula (VIIIa)

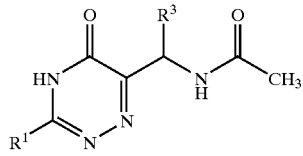

(VIIIa)

in which
$R^1$ and $R^3$ have the meaning indicated above,
are reacted with a suitable acid in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, alcohols such as methanol, ethanol, n-propanol, iso-propanol, n-butanol or tert-butanol, hydrocarbons such as benzene, xylene, toluene, hexane, cyclohexane or petroleum fractions, or other solvents such as nitromethane, ethyl acetate, acetone, dimethylformamide, dimethylacetamide, 1,2-dimethoxyethane, 2-butanone, dimethyl sulphoxide, acetonitrile or pyridine, those preferred are methanol or ethanol, in the presence of an acid, such as trifluoroacetic acid, sulphuric acid, hydrogen chloride, hydrogen bromide and acetic acid or a mixture thereof, optionally with addition of water, hydrogen chloride or hydrogen chloride/water is particularly preferred, preferably in a temperature range from room temperature to 100° C. at normal pressure.

For the preparation of the compounds of the formula (VIII), compounds of the general formula (XI),

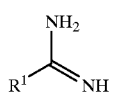
(XI)

or their salts, e.g. hydrochloride or hydrobromide salts, in which
$R^1$ has the meaning indicated above,
are reacted in the first stage with hydrazine in inert solvents which do not change under the reaction conditions, for example alcohols such as methanol, ethanol, n-propanol, isopropanol, n-butanol or tert-butanol, or other solvents such as dimethylformamide or dimethyl sulphoxide, those preferred are methanol or ethanol, in a temperature range from −10° C. to 50° C. at normal pressure (cf. for example K. M. Doyle, F. Kurzer, *Synthesis* 1974, 583), and subsequently with compounds of the formula (XII),

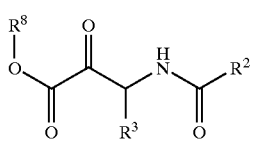
(XII)

in which
$R^2$ and $R^3$ have the meaning indicated above, and
$R^8$ represents $(C_1–C_4)$-alkyl, preferred methyl or ethyl,
in inert solvents, for example alcohols such as methanol, ethanol, n-propanol, isopropanol, n-butanol or tert-butanol, or other solvents such as dimethylformamide or dimethyl sulphoxide, those preferred are methanol or ethanol, in a temperature range from room temperature up to reflux of the solvents at normal pressure.

Compounds of the formula (VIIIa) are prepared using compounds of the formula (XI) and compounds of the formula (XII),
in which
$R^2$ represents methyl,
under the same conditions as compounds of the formula (VIII) are prepared.

For the preparation of the compounds of the formula (XI), compounds of the general formula (XIII),

 (XIII)

in which
$R^1$ has the meaning indicated above, and
$Y^2$ represents cyano or methoxycarbonyl,
are reacted in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as 1,2-dimethoxyethane, acetonitrile or pyridine, preferably toluene with trimethylaluminium in hexane and ammonium chloride, firstly at −20° C. and then at room temperature to 80° C. at normal pressure (cf. for example R. S. Garigipati, *Tetrahedron Lett.* 1990, 31, 1969–1972), or if $Y^2$ represents cyano, with ammonium bromide or chloride and gaseous ammonia at 140° C. to 150° C. in an autoclave, or with lithium bis(trimethylsilyl)amine and hydrogen chloride in diethyl ether (cf. R. T. Boeré et al., *J. Organomet. Chem.* 1987, 331, 161–167).

The compounds of the general formula (XIII) are known or can be synthesized from the appropriate starting materials according to known processes.

Instead of compounds of the formula (XI), compounds of the formula (XIV),

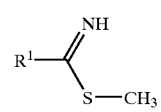
(XIV)

in which
$R^1$ has the meaning indicated above,
can also be employed, which are prepared according to K. M. Doyle, F. Kurzer, *Synthesis* 1974, 583.

The compounds of the general formula (XIV) are known or can be synthesized from the appropriate starting materials according to known processes.

For the preparation of the compounds of the formula (XII), compounds of the general formula (XV),

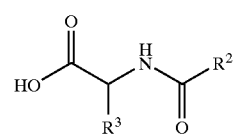
(XV)

in which
$R^2$ and $R^3$ have the meaning indicated above,
are reacted with compounds of the general formula (XVI),

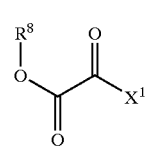
(XVI)

in which
$R^8$ has the meaning indicated above, and
$X^1$ represents halogen, preferably chlorine or bromine,
in inert solvents, these include halogenohydrocarbons such as methylene chloride, trichloromethane, tetrachloromethane, trichloroethane, tetrachloroethane, 1,2- dichloroethane or tri chloro ethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, acetone, dimethylformamide, dimethylacetamide, 1,2-dimethoxyethane, 2-butanone, dimethyl sulphoxide, acetonitrile or pyridine, preferably tetrahydrofuran or diethyl ether, optionally in the presence of a base, such as, for example, alkali metal carbonates such as caesium carbonate, sodium or potassium carbonate, or potassium tert-butoxide, or amides such as sodium amide, lithium bis-(trimethylsilyl)amide, lithium diisopropylamide, or other bases such as sodium hydride, DBU, triethylamine, pyridine, piperidine or diisopropylethylamine, preferably pyridine, sodium hydride, potassium tert-butoxide, lithium diisopropylamide, piperidine or triethylamine, optionally in the presence of a catalyst such as dimethylaminopyridine at room temperature up to reflux of the solvents at normal pressure (cf. for example Charles, *J. Chem. Soc., Perkin Trans.* 1, 1980, 1139).

The compounds of the general formula (XVI) are known or can be synthesized from the appropriate starting materials according to known processes.

For the preparation of the compounds of the formula (XV), compounds of the general formula (XVII),

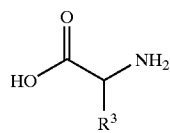

(XVII)

in which $R^3$ has the meaning indicated above, are reacted with compounds of the general formula (XVIII),

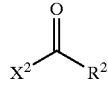

(XVIII)

in which $R^2$ has the meaning indicated above, and $X^2$ represents halogen, preferably chlorine or bromine, in inert solvents, these include halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, acetone, dimethylformamide, dimethylacetamide, 1,2-dimethoxyethane, 2-butanone, dimethyl sulphoxide, acetonitrile or pyridine, preferably methylene chloride, optionally in the presence of a base, such as for example alkali metal hydroxides such as sodium or potassium hydroxide, optionally as a mixture with water, or alkali metal carbonates such as caesium carbonate, sodium or potassium carbonate, or potassium tert-butoxide, or amides such as sodium amide, lithium bis-(trimethylsilyl) amide, lithium diisopropylamide, or other bases such as DBU, triethylamine, pyridine, piperidine or diisopropylethylamine, preferably triethylamine, sodium or potassium hydroxide as a mixture with water, optionally in the presence of trimethylsilyl chloride at −10° C. up to reflux of the solvents at normal pressure.

The compounds of the general formula (XVII) and (XVIII) are known or can be synthesized from the appropriate starting materials according to known processes.

For the syntheses of intermediates of compounds of the formula (I), the synthesis methods described in WO 99/24433 and EP-A-1 092 719 are optionally also used.

Functional groups are optionally protected during the syntheses using suitable, customary protective groups, which are subsequently removed again using customary synthesis methods (cf. T. W. Greene, P. Woods, "Protective Groups in Organic Synthesis", 2nd Ed., Wiley; New York, 1991).

The processes described above can be illustrated by way of example by the following reaction schemes:

Scheme 1:

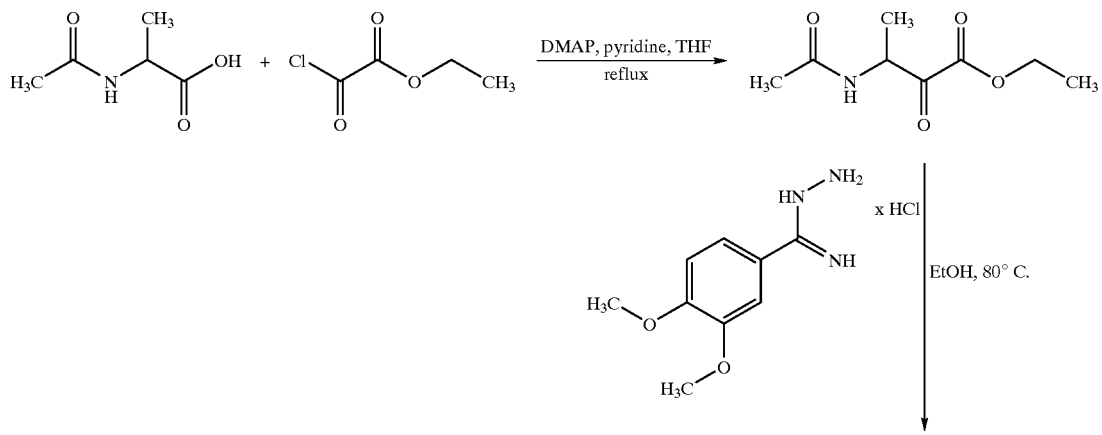

-continued
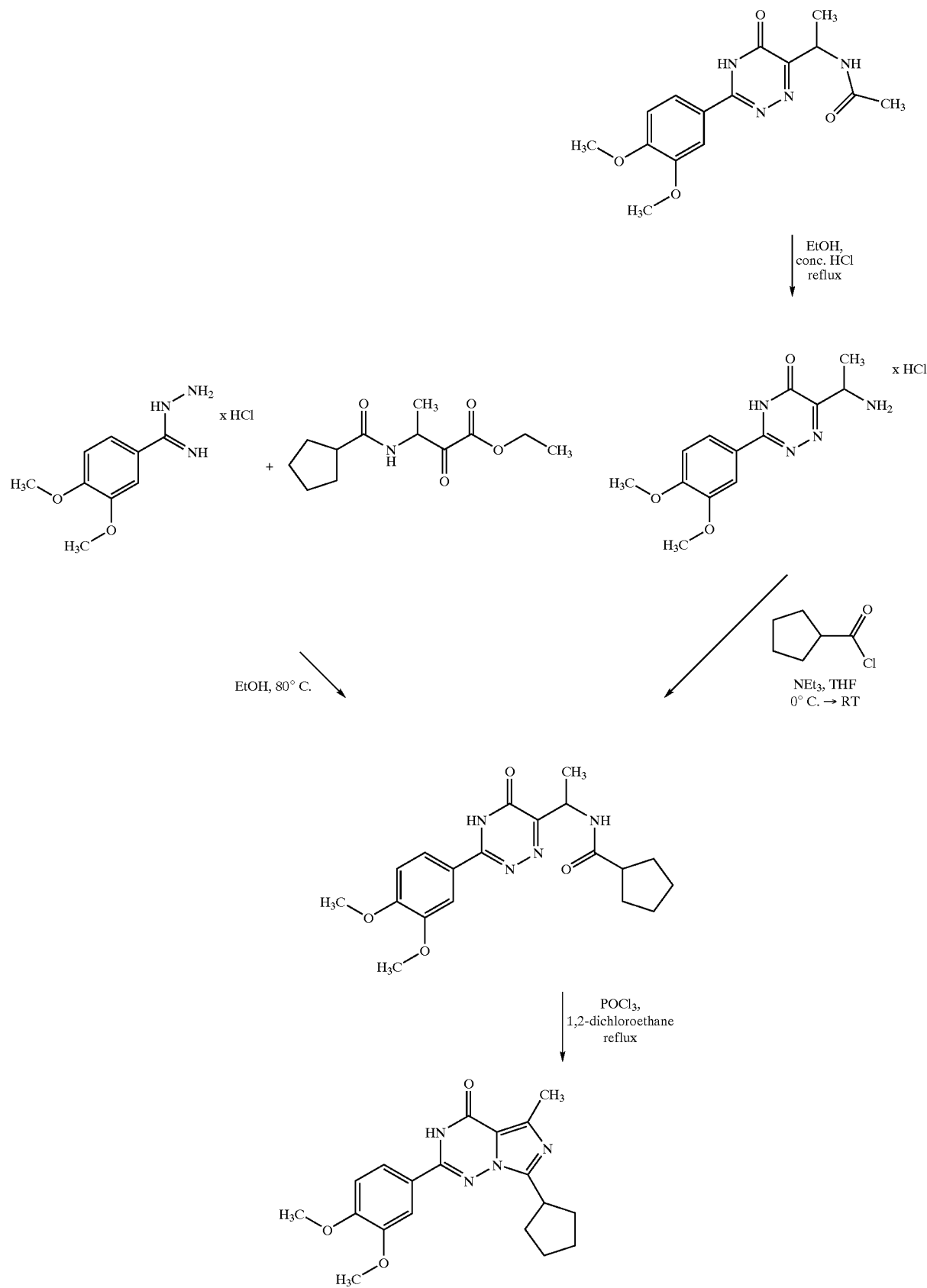

Scheme 2: Process [A]
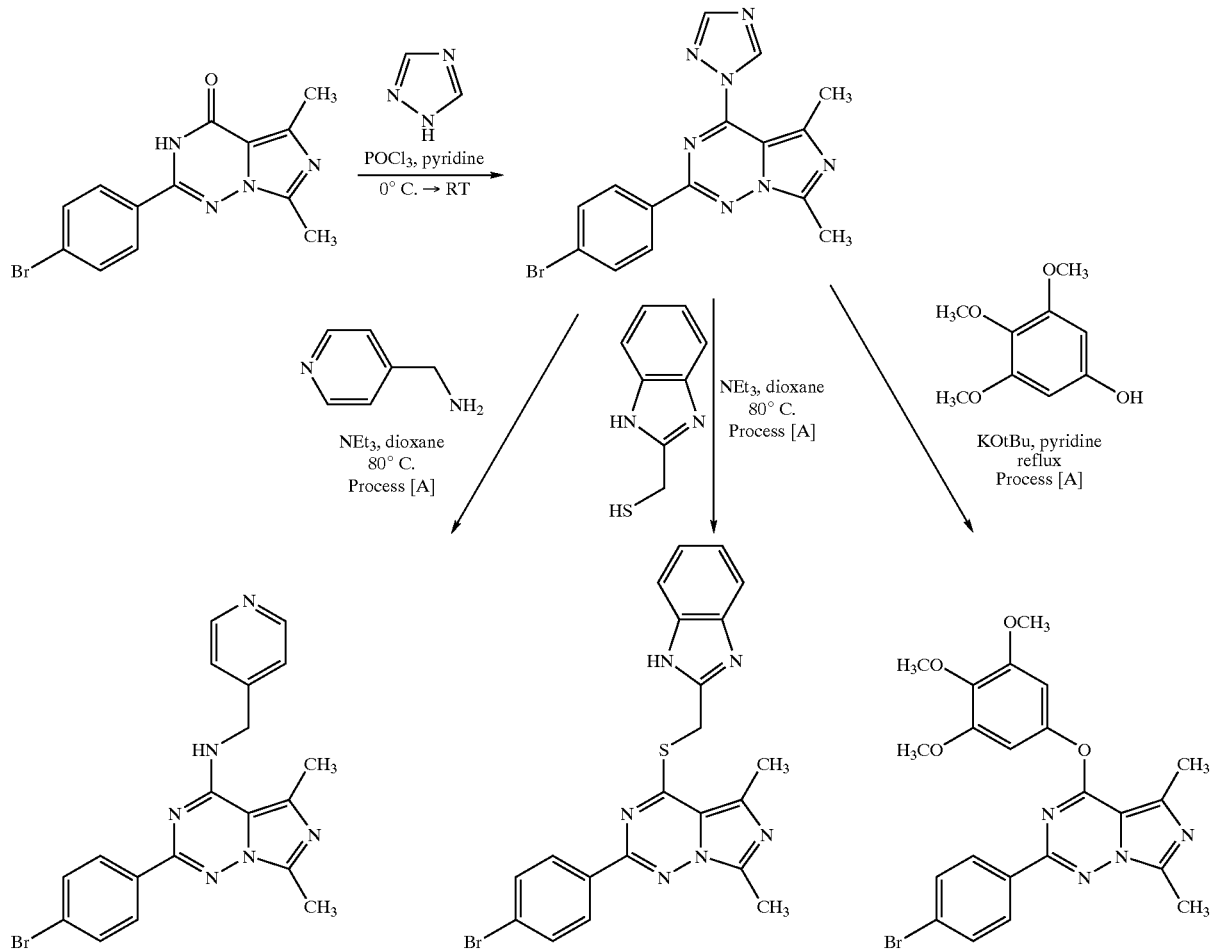
Scheme 3: Process [B]
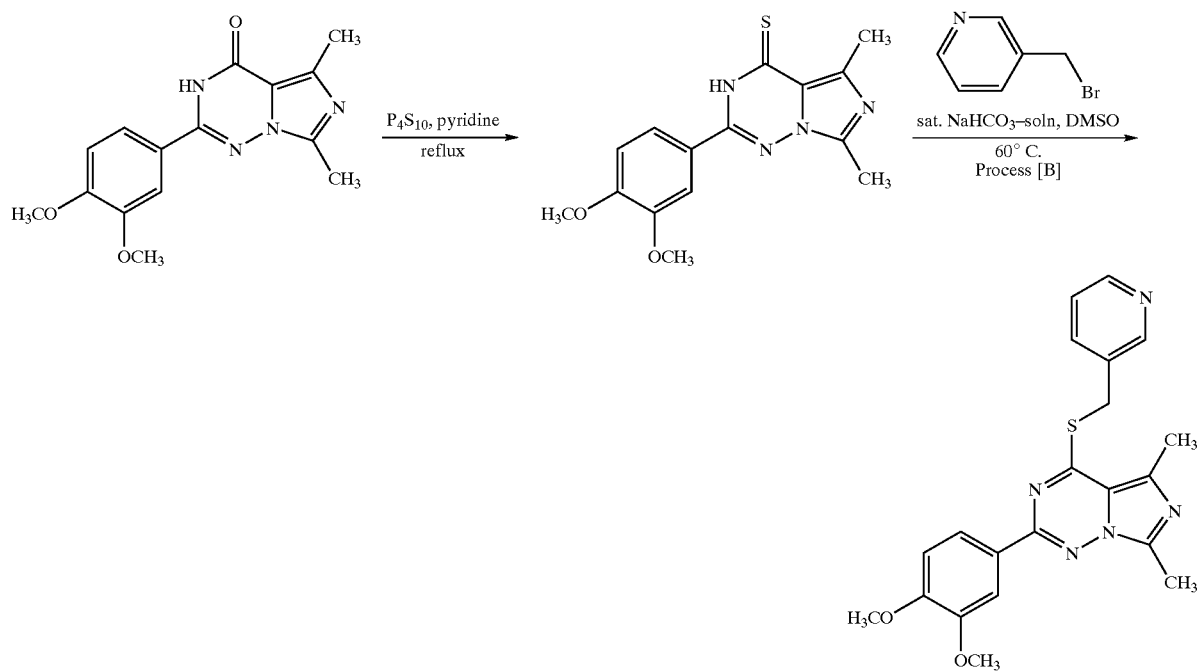

The compounds of the general formula (I) according to the invention are suitable for use as medicaments in the treatment of humans and animals.

The compounds according to the invention exhibit an unforeseeable, valuable spectrum of pharmacological action.

They are distinguished as PDE 10A inhibitors.

On account of their pharmacological properties, the compounds according to the invention can be employed on their own or in combination with other medicaments for the treatment and/or prevention of Parkinson's disease and of cancer.

Moreover, it is shown for the first time that selective PDE 10A inhibitors act in animal models of Parkinson's disease.

The in vitro action of the compounds according to the invention can be shown using the following biological assays:

In Vitro Enzyme Inhibition Tests:

Inhibition of PDE 10A

PDE10A (WO 01/29 199, FIG. 1A) is expressed recombinantly in full length in Sf9 insect cells (Invitrogen, Carlsbad, Calif.) with the aid of the Bac-to-Bac™ Baculovirus expression system of Life Technologies (Gaithersburg, Md.). 48 h after the infection, the cells are harvested and suspended in 20 ml (per 1 l of culture) of lysis buffer (50 mM tris HCl, pH 7.4, 50 mM NaCl, 1 mM $MgCl_2$, 1.5 mM EDTA, 10% glycerol plus 20 µl of Protease Inhibitor Cocktail Set III [CalBiochem, La Jolla, Calif. USA]). The cells are treated at 4° C. for 1 minute with ultrasound and subsequently centrifuged at 10000 rpm for 30 minutes at 4° C. The supernatant (PDE10A preparation) was collected and stored at −20° C.

The test substances are dissolved and serially diluted in 100% DMSO for the determination of their in vitro action on PDE 10A. Typically, dilution series of 200 µM to 1.6 µM are prepared (resulting final concentrations in the test: 4 µM to 0.032 µM). In each case, 2 µl of the diluted substance solutions are introduced into the wells of microtitre plates (Isoplate; Wallac Inc., Atlanta, Ga.). 50 µl of a dilution of the PDE10A preparation described above are subsequently added. The dilution of the PDE10A preparation is chosen such that during the later incubation less than 70% of the substrate is reacted (typical dilution: 1:10000; dilution buffer: 50 mM tris/HCl pH 7.5, 8.3 mM $MgCl_2$, 1.7 mM EDTA, 0.2% BSA). The substrate, [5',8-$^3$H] adenosine 3', 5'-cyclic phosphate (1 µCi/µl; Amersham Pharmacia Biotech., Piscataway, N.J.) is diluted 1:2000 to a concentration of 0.0005 µCi/µl with assay buffer (50 mM tris/HCl pH 7.5, 8.3 mM $MgCl_2$, 1.7 mM EDTA). The enzyme reaction is finally started by addition of 50 µl (0.025 µCi) of the diluted substrate. The test batches are incubated at room temperature for 60 min and the reaction is stopped by addition of 25 µl of a suspension containing 18 mg/ml of Yttrium Scintillation Proximity Beads (Amersham Pharmacia Biotech., Piscataway, N.J.). The microtitre plates are sealed using a film and allowed to stand at room temperature for 60 min. The plates are subsequently measured for 30 s per well in a Microbeta scintillation counter (Wallac Inc., Atlanta, Ga.). $IC_{50}$ values are determined with the aid of graphic plotting of the substance concentration against the percentage inhibition.

The PDE 10A-inhibiting action of the compounds according to the invention is confirmed by the following examples:

| Example | $IC_{50}$ [nM] |
| --- | --- |
| 16 | 210 |
| 43 | 2400 |
| 48 | 68 |
| 12 | 460 |
| 18 | 91 |
| 3 | 360 |
| 24 | 13 |
| 53 | 45 |

Inhibition of the PDEs 1–5 and 7

Recombinant PDE1C (GenBank/EMBL Accession Number: NM_005020), PDE2A (Rosman et al. *Gene* 1997 191, 89–95), PDE3B (Miki et al. *Genomics* 1996 36, 476–485), PDE4B (Bolger et al. *Mol. Cell. Biol.* 1993 13, 6558–6571), PDE5A (GenBank/EMBL Accession Number: AJ004865) and PDE7B (Hetman et al. *Proc. Natl. Acad. Sci. U.S.A.* 2000 97, 472–476) were expressed in Sf9 cells with the aid of the pFASTBAC Baculovirus expression system (GibcoBRL).

The in vitro action of test substances on recombinant PDE3B, PDE4B and PDE7B is determined according to the test protocol described above for PDE 10A. For the determination of a corresponding action on recombinant PDE1C, PDE2A and PDE5A, the protocol is adapted as follows: in the case of PDE1C, calmodulin $10^{-7}$ M and $CaCl_2$ 3 mM are additionally added to the reaction batch. PDE2A is stimulated in the test by addition of cGMP 1 µM and tested using a BSA concentration of 0.01%. For PDE5A, [8-$^3$H] cGMP (Amersham Pharmacia Biotech., Piscataway, N.J.) is employed as substrate.

The suitability of the compounds according to the invention for the treatment of Parkinson's disease can be shown in the following animal models:

6-Hydroxydopamine (6-OH-DA) Lesion on the Rat

The degeneration of the dopaminergic nigrostriatal and striatopallidal neuro-transmission is the main sign of Parkinson's disease. The clinical picture of Parkinson's disease can be simulated to a large part in an animal model in which the neurotoxin 6-OH-DA is injected intracerebrally into rats.

For the experiments described, male rats (Harlan Winkelmann, Germany; weight at the start of the experiments: 180–200 g) are used. The experimental animals are kept under controlled conditions (atmospheric humidity, temperature) and a 12 hour light-dark cycle. The animals—provided they are not in an experiment—have free access to water and food.

On the day of the operation, 30 minutes before the lesion the animals are administered pargyline (Sigma, St. Louis, Mo., USA; 50 mg/kg i.p.) and desmethylimipramine HCl (Sigma; 25 mg/kg i.p.) in order to suppress the metabolism of 6-hydroxydopamine, or in order to prevent the uptake of 6-hydroxy-dopamine into noradrenergic structures. After the initiation of anaesthesia by sodium pentobarbital (50 mg/kg i.p.), the experimental animals are fixed in a stereotactic frame. Lesion of the nigrostriatal neurotransmission is carried out by a unilateral, single injection of 8 µg of 6-OH-DA HBr (Sigma, St. Louis, Mo., USA), dissolved in 4 µl of a 0.01% strength ascorbic acid-saline solution. The solution was slowly injected at 1 µl/min. According to König and Klippel, the coordinates of the injection are: 2.4 mm anterior, 1.49 mm lateral, −2.7 mm ventral. After the injection, the injection needle was left in situ for a further 5 minutes in order to facilitate the diffusion of the neurotoxin.

After the operation, the animals are placed on a warm plate and, after regaining consciousness, taken to their cages again under control and received food and water ad libidum.

In the drug group, the animals are treated with substance one day after the operation up to the end of the experiment 28 days after the operation.

The motor failures after the lesion are quantified using the following tests as described in the respective literature:
a) Staircase Test (Coordination Test of the Forepaws):
Barnéoud et al: Effects of complete and partial lesions of the dopaminergic mesotelencephalic system on skilled forelimb use in the rat. *Neuroscience* 1995, 67, 837–848.
b) Accelerating Rotarod Test (Balancing Test):
Spooren et al.: Effects of the prototypical mGlu$_5$ receptor antagonist 2-methyl-6-(phenylethynyl)-pyridine on rotarod, locomotor activity and rotational responses in unilateral 6-OHDA-lesioned rats. *Eur. J. Pharmacol.* 2000, 406, 403–410.
c) Tractive Force Measurement of the Forepaws:
Dunnet et al.: A laterised grip strength test to evaluate unilateral nigrostriatal lesions in rats. *Neurosci. Lett.* 1998, 246, 1–4.

MPTP Monkey Model

The in vivo action of the compounds according to the invention can be shown in a monkey model of Parkinson's disease, the 'chronic MPTP model' (Bézard et al. *Brain Res.* 1997, 766, 107–112). MPTP (=1-methyl-4-phenyl-1,2,3,6-tetrahydropyridine) is a neurotoxin which in humans and animals causes the typical degeneration of dopaminergic neurons in the substantia nigra typical of Parkinson's disease. Moreover, in the human and in the monkey MPTP produces the motor symptoms typical of Parkinson's disease. These symptoms are assessed on a Parkinson scale for monkeys.

For the experiments, rhesus monkeys (Macaca fascicularis) are treated daily with MPTP (0.2 mg/kg i.v.) until they have achieved a score of 8 on the Parkinson scale. The first Parkinson symptoms occur after 5–10 days' MPTP treatment. On account of the long-term action of the neurotoxin, the clinical symptoms of the animals develop further to full Parkinsonism (score>15).

The new active compounds can be converted in a known manner into the customary formulations, such as tablets, coated tablets, pills, granules, aerosols, syrups, emulsions, suspensions and solutions, using inert, non-toxic, pharmaceutically suitable vehicles or solvents. In this collection, the therapeutically active compound should in each case be present in a concentration of approximately 0.5 to 90% by weight of the total mixture, i.e. in amounts which are adequate in order to achieve the dosage range indicated.

The formulations are produced, for example, by extending the active compounds using solvents and/or vehicles, optionally using emulsifying agents and/or dispersing agents, it being possible, for example, in the case of the use of water as a diluent for organic solvents optionally to be used as auxiliary solvents.

Administration is carried out in a customary manner, preferably orally, transdermally or parenterally, in particular perlingually or intravenously. However, it can also be carried out by inhalation via the mouth or nose, for example with the aid of a spray, or topically via the skin.

In general, it has proved advantageous to administer amounts of approximately 0.001 to 10 mg/kg, in the case of oral administration preferably approximately 0.005 to 3 mg/kg, of body weight to achieve efficacious results.

In spite of this, it may optionally be necessary to depart from the amounts mentioned, namely depending on the body weight or on the type of administration route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into a number of individual doses over the course of the day.

Abbreviations:
abs. absolute
Ac acetyl
Acac acetylacetonyl
AIBN α,α'-azobis(isobutyronitrile)
Aloc Allyloxycarbonyl
aq. aqueous
9-BBN 9-borabicyclo[3.3.1]nonane
Bn benzyl
Boc tert-butoxycarbonyl
Bom benzyloxymethyl
BOP benzotriazol-1-yloxy-tris(dimethylamino)phosphonium hexafluorophosphate
B.p. boiling point
Bu butyl
Bz benzoyl
CAN cerammonium nitrate
Cbz benzyloxycarbonyl
CDI N,N'-carbonyldiimidazole
cf. compare
CH cyclohexane
conc. concentrated
Cp cyclopentadienyl
cryst. crystalline/crystallized
CSA 10-camphorsulphonic acid
Dabco 1,4-diazabicyclo[2.2.2]octane
DAST diethylaminosulphur trifluoride
DBN 1,5-diazabicyclo[4.3.0]non-5-ene
DBU 1,8-diazabicyclo[5.4.0]undec-7-ene
DCC N,N'-dicyclohexylcarbodiimide
DCE 1,2-dichloroethane
DCI direct chemical ionisation (in MS)
DCM dichloromethane
DDQ 2,3-dichloro-5,6-dicyano-1,4-benzoquinone
d.e. diastereomeric excess
DEAD diethyl azodicarboxylate
dec. decomposition
DHP 3,4-dihydro-2H-pyran
DIAD diisopropyl azodicarboxylate
DIBAH diisobutylaluminium hydride
DIC diisopropylcarbodiimide
DIEA N,N-diisopropylethylamine
dil. dilute
dist. distilled
DMA N,N-dimethylacetamide
DMAP 4-N,N-dimethylaminopyridine
DME 1,2-dimethoxyethane
DMF N,N-dimethylformamide
DMPU N,N'-dimethylpropyleneurea
DMSO dimethyl sulphoxide
DNPH 2,4-dinitrophenylhydrazine
DPPA diphenylphosphoryl azide
EA ethyl acetate
EDC N'-(3-dimethylaminopropyl)-N-ethylcarbodiimide×HCl
e.e. enantiomeric excess
EI electron impact ionisation (in MS)
eq equivalent(s)
ESI electrospray ionisation (in MS)
Et ethyl
Fmoc fluorenylmethoxycarbonyl Fr. fraction
GC gas chromatography
HATU O-(7-azabenzotriazol-1-yl)-N,N,N',N'-tetramethyluronium hexafluorophosphate
HBTU O-(benzotriazol-1-yl)-N,N,N',N'-tetramethyluronium hexafluorophosphate
HMDS 1,1,1,3,3,3-hexamethyldisilazane
HMPA or HMPT hexamethylphosphoramide
HOBt 1-hydroxy-1H-benzotriazol×H$_2$O
HOSu N-hydroxysuccinimide
HPLC high pressure, high-performance liquid chromatography
Im imidazol-1-yl
IR infrared spectroscopy
LAH lithium aluminium hydride
LC-MS liquid chromatography-coupled mass spectroscopy
LDA lithium N,N diisopropylamide
LiHMDS lithium N,N-bistrimethylsilylamide
liq. liquid
Lit. literature
m meta
mCPBA meta-chloroperbenzoic acid
Me methyl
MEK methyl ethyl ketone
MEM methoxyethoxymethyl
MOM methoxymethyl
M.p. melting point
MPLC medium pressure liquid chromatography
Ms methanesulphonyl (mesyl)
MS mass spectroscopy
MTBE methyl tert-butyl ether
MW molecular weight
NBS N-bromosuccinimide
NCS N-chlorosuccinimide
NIS N-iodosuccinimide
NMM N-methylmorpholine
NMO N-methylmorpholine N-oxide
NMR nuclear magnetic resonance spectroscopy
o ortho
p para
p.A. pro analysi
PCC pyridinium chlorochromate
PDC pyridinium dichromate
Pfp pentafluorophenyl
Ph phenyl
Piv pivaloyl
PMB p-methoxybenzyl
PNB p-nitrobenzyl
PPA polyphosphoric acid
ppt. precipitate
PPTS pyridinium p-toluenesulphonate
Pr propyl
PS polystyrene (resin)
py pyridine
PyBOP benzotriazol-1-yloxy-tris(pyrrolidino)phosphonium hexafluorophosphate
RF reflux
R$_f$ retention index (in TLC)
RP reverse phase (in HPLC)
RT room temperature
R$_t$ retention time (in HPLC)
sat. saturated
SEM 2-(trimethylsilyl)ethoxymethyl
soln solution
subl. sublimed
TBAF tetrabutylammonium fluoride
TBAI tetrabutylammonium iodide
TBDMS tert-butyldimethylsilyl
TBDPS tert-butyldiphenylsilyl
TBTU O-(benzotriazol-1-yl)-N,N,N',N'-tetramethyluronium tetrafluoroborate
TEA triethylamine
techn. technical
Teoc 2-(trimethylsilyl)ethoxycarbonyl
TES triethylsilyl
Tf trifluoromethanesulphonyl
TFA trifluoroacetic acid
TFAA trifluoroacetic anhydride
TfOH trifluoromethanesulphonic acid
THF tetrahydrofuran
THP tetrahydropyranyl
TIPS triisopropylsilyl
titr. titrated
TLC thin-layer chromatography
TMEDA N,N,N',N'-tetramethylethylenediamine
TMOF Trimethyl orthoformate
TMS trimethylsilyl
TPP triphenylphosphine
TPPO triphenylphosphine oxide
Trt trityl
Ts p-toluenesulphonyl (tosyl)
TsOH p-toluenesulphonic acid
v/v volume to volume ratio (of a solution)
vol. volume
W/W weight to weight ratio (of a solution)
Z benzyloxycarbonyl
Starting Compounds

EXAMPLE 1A 3,4-Dimethoxybenzenecarboximidamide hydrochloride

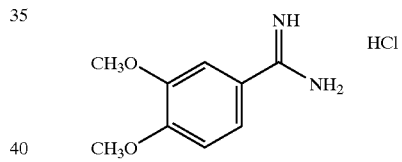

21.4 g (400 mmol) of ammonium chloride are suspended in 200 ml of anhydrous toluene under an argon atmosphere in a three-necked flask having a thermometer, condenser, dropping funnel and mechanical stirrer and cooled to 0° C. 400 mmol of trimethylaluminium (200 ml of 2 M solution in hexane) are added dropwise, and the batch is stirred at room temperature until evolution of gas is no longer observed (about 1.5 h). A solution of 33.6 g (200 mmol) of 3,4-dimethoxybenzonitrile in 100 ml of dry toluene is added dropwise and the reaction mixture is stirred at 80° C. for 18 h.

After cooling, the mixture is treated dropwise at −10° C. with 60 ml of methanol and subsequently stirred vigorously at RT for 90 min. The batch is filtered with suction and the residue is washed with methanol (5×200 ml). The filtrate is concentrated, the residue is washed with methanol/diethyl ether mixture and diethyl ether and the solid obtained (yield: 28.2 g) is dried. The washing phases are concentrated, taken up in ethanol and decolourized using active carbon. The active carbon is filtered off and the filtrate is concentrated. The residue obtained is treated with diethyl ether and filtered off with suction. A further 11.2 g of product are obtained.

Total yield 92% of theory $^1$H-NMR (200 MHz, DMSO-d$_6$): δ=3.85 (s, 3H), 3.86 (s, 3H), 7.17 (d, 1H), 7.45 (d, 1H), 7.47–7.53 (m, 1H).

EXAMPLE 2A

4-Methoxybenzenecarboximidamide hydrochloride

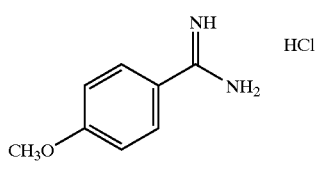

Preparation analogously to Example 1A from 27.0 g (200 mmol) of anisonitrile.

Yield: 23.8 g (64% of theory)

$^1$H-NMR (200 MHz, DMSO-$d_6$): δ=3.86 (s, 3H), 7.51 (d, 2H), 7.85 (d, 2H), 9.09 (s, br. 4H).

EXAMPLE 3A

3–Chloro-4-methoxybenzenecarboximidamide hydrochloride

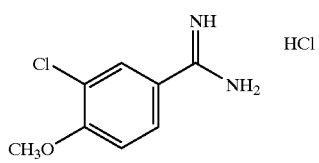

The preparation is carried out analogously to that described for Example 1A by reaction of 4.01 g (20 mmol) of methyl 3-chloro-4-methoxybenzoate with 4.81 g (90 mmol) of ammonium chloride and 90 mmol of trimethylaluminium (45 ml of 2 M solution in hexane) in toluene.

Yield: 4.36 g (91% of theory)

$^1$H-NMR (200 MHz, DMSO-$d_6$): δ=3.97 (s, 3H), 7.38 (d, 1H), 7.85–7.91 (m, 1H), 8.02 (d, 1H), 9.19 (s, bar 3H).

EXAMPLE 4A

4-Bromobenzenecarboximidamide hydrobromide

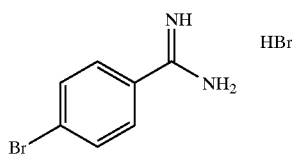

In an autoclave, 4-bromobenzonitrile (36.4 g, 200 mmol), ammonium bromide (39.2 g, 400 mmol) and ammonia gas (34.0 g, 2 mol) are heated to 140–150° C. under autogenous pressure for 9 h. The contents of the autoclave are concentrated and extracted by stirring with ethanol. The residue is filtered off and extracted again by stirring with ethanol. The extracts are combined and concentrated to about 100 ml. The precipitated solid is filtered off with suction, washed with ethanol and dried.

Yield: 21.4 g (38% of theory)

$^1$H-NMR (400 MHz, DMSO-$d_6$): δ=7.75 (d, 2H), 7.87 (d, 2H), 9.10 (s, 3H).

EXAMPLE 5A 3,5-Dimethoxybenzenecarboximidamide hydrochloride

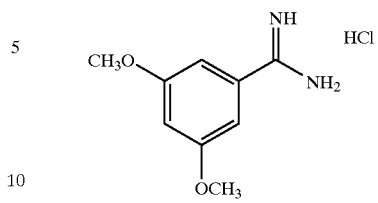

The preparation is carried out as described for Example 1A by reaction of 29.4 g (180 mmol) of 3,5-dimethoxybenzonitrile with 19.1 g (360 mmol) of ammonium chloride and 360 mmol of trimethylaluminium (179 ml of 2 M solution in hexane) in toluene.

Yield 23.7 g (62% of theory)

MS (DCI/NH$_3$): 181 [M+H]$^+$;

$^1$H-NMR (400 MHz, DMSO-$d_6$): δ=3.82 (s, 6H), 6.83 (t, 1H), 7.00 (s, 2H), 9.02–9.53 (b, 3H).

EXAMPLE 6A

Ethyl 3-(acetylamino)-2-oxobutanoate

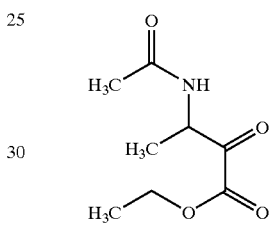

N-Acetyl-alanine (4.92 g, 37.5 mmol), 9.10 ml of pyridine and 150 mg of DMAP are dissolved in 200 ml of THF and the solution is brought to the boil. At boiling heat, 8.6 ml (10.5 g, 75 mmol) of ethyl oxalyl chloride are added dropwise, and, after addition is complete, the mixture is stirred at boiling heat for a further 3 h. After cooling, the reaction mixture is added to 600 ml of ice water, extracted with ethyl acetate (4×150 ml), and the combined organic phases are washed with 200 ml of sat. NaCl solution, dried over sodium sulphate and concentrated. The material obtained is reacted further without delay dissolved in ethanol.

EXAMPLE 7A

N-(Cyclopentylcarbonyl)alanine

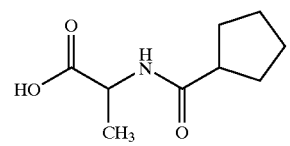

Alanine (16.8 g, 189 mmol) and 57.8 ml (415 mmol) of triethylamine are dissolved in 200 ml of dichloromethane and 52.7 ml (415 mmol) of trimethylsilyl chloride are added dropwise. After addition is complete, the mixture is stirred for 1 h at room temperature and for 1 h at 40° C. After this, the batch is cooled to −10° C. and cyclopentanecarbonyl chloride (25.0 g, 189 mmol) is added dropwise and the mixture is stirred at this temperature for 2 h. The reaction mixture is treated with 100 ml of water with cooling, stirred for 10 min and and filtered with suction. The residue is washed with water and diethyl ether and dried at 60° C.

Yield: 25.8 g (74% of theory)

$^1$H-NMR (400 MHz, methanol-d$_4$): δ=1.37 (d, 3H), 1.56 (m, 2H), 1.71 (m, 4H), 1.85 (m, 2H), 2.66 (quint., 1H), 4.35 (q, 1H).

EXAMPLE 8A

2-[(Cyclopentylcarbonyl)amino]butanoic acid

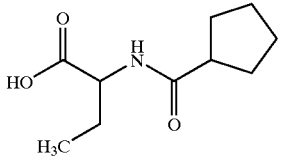

Preparation analogously to Example 7A from 50 g (485 mmol) of 2-aminobutyric acid.

Yield: 72 g (75% of theory)

MS (ESI): 200 [M+H]$^+$;

$^1$H-NMR (300 MHz, DMSO-d$_6$): δ=0.89 (t, 3H), 1.47–1.72 (m, 10H), 2.64 (quint., 1H), 4.10 (m, 1H), 7.93 (d, 1H), 12.45 (s, 1H).

EXAMPLE 9A

Ethyl 3-[(cyclopentylcarbonyl)amino]-2-oxobutanoate

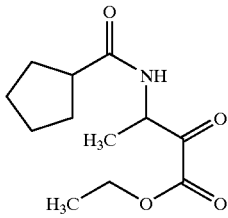

Preparation analogously to Example 6A from N-(cyclopentylcarbonyl)alanine. The crude product obtained is directly reacted further.

EXAMPLE 10A

Ethyl 3-[(cyclopentylcarbonyl)amino]-2-oxopentanoate

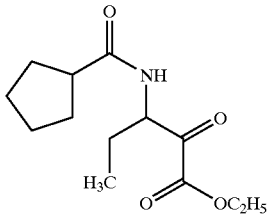

Preparation analogously to Example 6A. The crude product is directly reacted further.

EXAMPLE 11A

N-{1-[3-(3,4-Dimethoxyphenyl)-5-oxo-4,5-dihydro-1,2,4-triazin-6-yl]ethyl}-acetamide

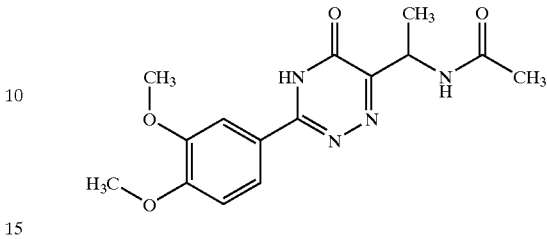

Example 1A (5.42 g, 25 mmol) is introduced into 100 ml of ethanol. 1.34 ml of hydrazine hydrate (1.34 g, 27.5 mmol) are added and the batch is stirred at 45° C. for 3 h. After this time, Example 6A is added in 50 ml of ethanol and the reaction mixture is stirred at a bath temperature of 80° C. for 6 h, then at room temperature for 12 h. The batch is concentrated and the residue is purified by flash chromatography (eluent gradient dichloromethane/methanol 40:1 to 20:1).

Yield: 2.85 g (35% of theory), amorphous solid.

M.p.: 218° C.

$^1$H-NMR (300 MHz, DMSO-d$_6$): δ=1.35 (d, 3H), 1.84 (s, 3H), 3.84 (s, 3H), 3.85 (s, 3H), 5.00 (quint, 1H), 7.16 (d, 1H), 7.59–7.77 (m, 2H), 8.24 (d, 1H), 13.93 (s, 1H).

EXAMPLE 12A 6-(1-Aminoethyl)-3-(3,4-dimethoxyphenyl)-1,2,4-triazin-5(4H)-one hydrochloride

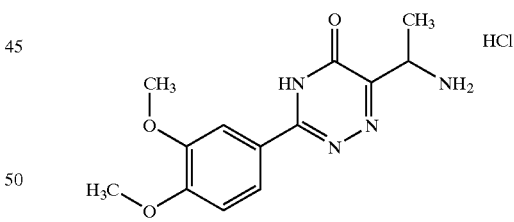

8.00 g (25.1 mmol) of Example 11A are introduced into 400 ml of ethanol, treated with 400 ml of conc. hydrochloric acid in portions with stirring and the batch is stirred under reflux for 20 h. After cooling, the clear, yellow solution is concentrated to dryness, the residue is treated with about 100 ml of toluene and the solution is concentrated on a rotary evaporator. This process is repeated a further 4 times. The amorphous, yellow product is then dried in a high vacuum for 20 h.

$^1$H-NMR (300 MHz, DMSO-d$_6$): δ=1.51 (d, 3H), 3.87 (s, 6H), 4.51 (m, 1H), 7.18 (d, 1H), 7.75 (d, 1H), 7.82 (dd, 1H), 8.52 (br. s, 3H).

EXAMPLE 13A

N-{1-[3-(3,4-Dimethoxyphenyl)-5-oxo-4,5-dihydro-1,2,4-triazin-6-yl]ethyl}-cyclopentanecarboxamide

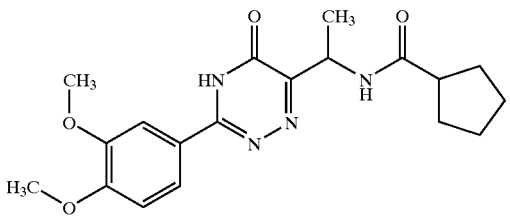

Example 12A (9.00 g, 25.9 mmol) and 9.03 ml (64.7 mmol) of triethylamine are introduced into 120 ml of THF under argon. A solution of 3.43 g (25.9 mmol) of cyclopentanecarbonyl chloride in 10 ml of THF is added dropwise to the suspension at 0° C. The suspension is stirred at 0° C. for 30 min and at RT for 1.5 h. The reaction mixture is extracted with 200 ml of water and with dichloromethane (5×100 ml). The combined org. phases are dried (sodium sulphate), filtered and concentrated. The crude product is purified by flash chromatography [silica gel 60 (70–230 mesh), eluent dichloromethane/methanol 9:1]. After concentrating and drying in a high vacuum, 7.00 g of product (71% of theory) are obtained.

M.p.: 218° C.

$^1$H-NMR (200 MHz, DMSO-$d_6$): δ=1.33 (d, 3H), 1.41–1.84 (m, 8H), 2.55–2.74 (m, 1H), 3.84 (s, 3H), 3.85 (s, 3H), 5.02 (quint, 1H), 7.15 (d, 1H), 7.61–7.78 (m, 2H), 8.09 (d, 2H), 13.84 (s, br 1H).

EXAMPLE 14A

N-{1-[3-(4-Methoxyphenyl)-5-oxo-4,5-dihydro-1,2,4-triazin-6-yl]ethyl}-cyclopentanecarboxamide

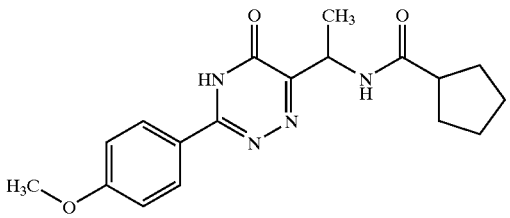

Example 2A (0.93 g, 5.00 mmol) and 0.27 ml (5.50 mmol) of hydrazine hydrate are dissolved in 25 ml of ethanol and the solution is stirred at 40° C. for 2.5 h. After this time, Example 9A (total amount) in 15 ml of ethanol is added, the mixture is stirred at a bath temperature of 80° C. for 2 h and then allowed to stand at room temperature overnight. The precipitated solid is filtered off with suction, washed with slightly cold ethanol and dried.

Yield: 440 mg (26% of theory)

$^1$H-NMR (300 MHz, DMSO-$d_6$): δ=1.33 (d, 3H), 1.40–1.84 (m, 8H), 2.58–2.73 (m, 1H), 3.85 (s, 3H), 5.02 (quint, 1H), 7.12 (d, 2H), 8.05 (d, 2H).

EXAMPLE 15A

N-{1-[3-(4-Methoxyphenyl)-5-oxo-4,5-dihydro-1,2,4-triazin-6-yl]propyl}-cyclopentanecarboxamide

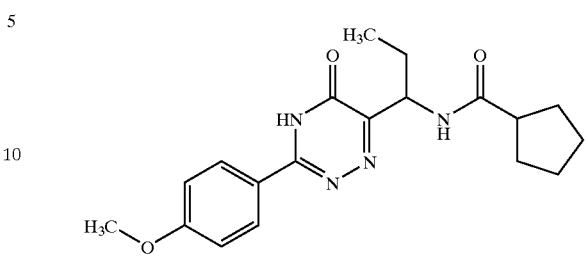

Preparation analogously to Example 14A from the appropriate starting compounds. Purification by flash chromatography (eluent dichloromethane/methanol 93:7)

$^1$H-NMR (200 MHz, CDCl$_3$): δ=0.91 (t, 3H), 1.51–2.10 (m, 10H), 2.67 (quint, 1H), 3.88 (s, 3H), 5.77–5.94 (m, 1H), 6.99 (d, 2H), 7.71 (d, 1H), 8.32 (d, 2H), 13.76 (s, 1H).

EXAMPLE 16A

N-{1-[3-(3-Chloro-4-methoxyphenyl)-5-oxo-4,5-dihydro-1,2,4-triazin-6-yl]ethyl}-acetamide

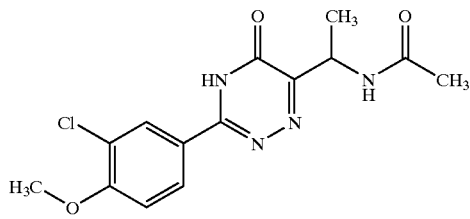

Preparation analogously to Example 11A from 4.20 g (19.0 mmol) of Example 3A.

Yield: 3.30 g of beige solid (52% of theory)

M.p.: 247° C.

$^1$H-NMR (300 MHz, DMSO-$d_6$): δ=1.33 (d, 3H), 1.84 (s, 3H), 3.96 (s, 3H), 5.01 (quint, 1H), 7.37 (d, 1H), 8.07 (dd, 1H), 8.14 (d, 1H), 8.24 (d, 1H), 13.96 (br s, 1H).

EXAMPLE 17A 6-(1-Aminoethyl)-3-(3-chloro-4-methoxyphenyl)-1,2,4-triazin-5(4H)-one hydrochloride

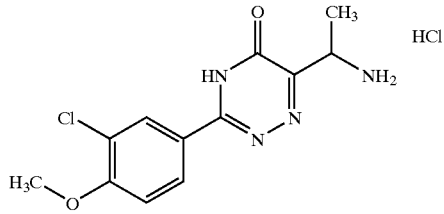

Preparation analogously to Example 12A from 3.00 g (9.30 mmol) of Example 16A. The product obtained is reacted without further purification.

$^1$H-NMR (300 MHz, DMSO-$d_6$): δ=1.50 (d, 3H), 3.97 (s, 3H), 4.53 (m, 1H), 7.39 (d, 1H), 8.15 (dd, 1H), 8.23 (d, 1H), 8.44 (br. s, 3H).

EXAMPLE 18A
N-{1-[3-(3–Chloro-4-methoxyphenyl)-5-oxo-4,5-dihydro-1,2,4-triazin-6-yl]ethyl}-3-methylbutanamide

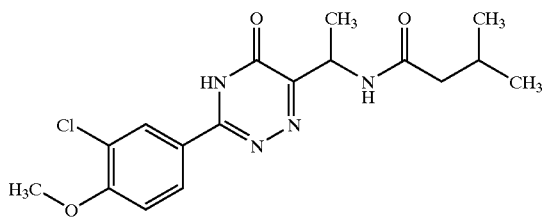

Example 17A (700 mg, 2.50 mmol) and triethylamine (1.04 ml, 7.48 mmol) are introduced into 15 ml of dry THF. At 0° C., 451 mg (3.74 mmol) of 3-methylbutanoyl chloride are added dropwise and the turbid reaction mixture is stirred at room temperature for 16 h. The batch is concentrated and the residue is purified by flash chromatography on silica gel (eluent gradient dichloromethane, dichloromethane/methanol 20:1).

M.p.: 236° C.

$^1$H-NMR (300 MHz, DMSO-$d_6$): δ=0.86 (d, 6H), 1.32 (d, 3H), 1.87–2.02 (m, 3H), 3.95 (s, 3H), 5.04 (quint, 1H), 7.36 (d, 1H), 8.03–8.19 (m, 2H), 8.13 (s, 1H), 13.96 (s, br 1H).

EXAMPLE 19A
N-{1-[3-(3–Chloro-4-methoxyphenyl)-5-oxo-4,5-dihydro-1,2,4-triazin-6-yl]ethyl}-2-methylbutanamide

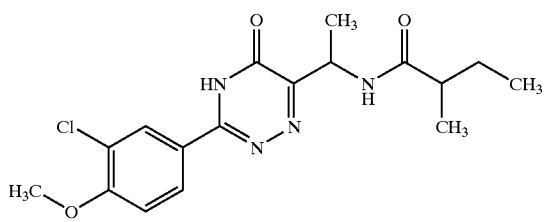

Preparation analogously to Example 18A from 700 mg (2.50 mmol) of Example 17A and 451 mg (3.74 mmol) of 2-methylbutanoyl chloride.

M.p.: 223° C.

$^1$H-NMR (200 MHz, DMSO-$d_6$): δ=0.80 (t, 3H), 0.96 (d, 3H), 1.33 (d, 3H), 1.41–1.55 (m, 1H), 2.03–2.33 (m, 2H), 2.55 (s, masked, 3H), 3.96 (s, 3H), 4.94–5.12 (m, 1H), 7.36 (d, 1H), 7.96–8.19 (m, 3H), 13.46 (s, br 1H).

EXAMPLE 20A
N-{1-[3-(3–Chloro-4-methoxyphenyl)-5-oxo-4,5-dihydro-1,2,4-triazin-6-yl]ethyl}-2-ethylbutanamide

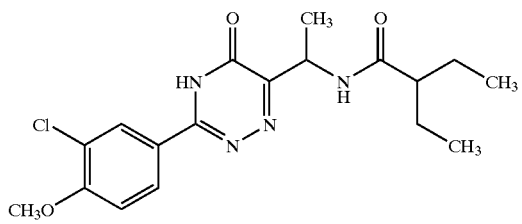

Preparation analogously to Example 18A from 700 mg (2.50 mmol) of Example 17A and 504 mg (3.74 mmol) of 2-ethylbutanoyl chloride.

$^1$H-NMR (300 MHz, DMSO-$d_6$): δ=0.80 (t, 6H), 1.22–1.51 (m, 4H), 1.33 (d, 3H), 1.99–2.11 (m, 1H), 2.55 (s, masked, 3H), 3.95 (s, 3H), 5.01–5.15 (m, 1H), 7.35 (d, 1H), 8.03–8.20 (m, 3H), 13.92 (s, br 1H).

EXAMPLE 21A
N-{1-[3-(4-Bromophenyl)-5-oxo-4,5-dihydro-1,2,4-triazin-6-yl]ethyl}acetamide

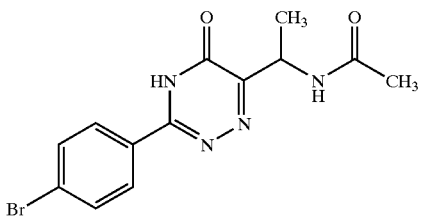

Example 4A (11.8 g) is introduced into 150 ml of ethanol. 3.50 ml of hydrazine hydrate (3.60 g, 27.5 mmol) are added and the batch is stirred for 1 h. After this time, Example 6A (16.8 g) in 76 ml of ethanol is added dropwise and the reaction mixture is stirred at a bath temperature of 80° C. for 3 h, then stirred at room temperature overnight. The batch is concentrated and the residue is purified by flash chromatography (eluent dichloromethane/methanol 95:5).

Yield: 4.58 g (15% of theory), amorphous solid

MS (ESI): 337 [M+H]$^+$;

$^1$H-NMR (200 MHz, CDCl$_3$): δ=1.54 (d, 3H), 2.07 (s, 3H), 4.31–4.48 (m, 1H), 5.26–5.41 (m, 1H), 7.43–7.57 (b, 1H), 7.66 (d, 2H), 8.12 (d, 2H).

EXAMPLE 22A
N-{1-[3-(4-Methylphenyl)-5-oxo-4,5-dihydro-1,2,4-triazin-6-yl]ethyl}acetamide

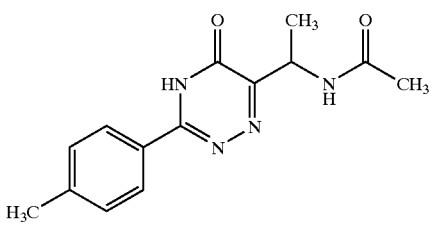

Preparation analogously to Example 21 A starting from 4-methylbenzamidine hydrochloride.

MS (ESI): 273 [M+H]$^+$;

$^1$H-NMR (300 MHz, DMSO-$d_6$): δ=1.33 (d, 3H), 1.84 (s, 3H), 2.40 (s, 3H), 5.02 (quin., 1H), 7.39 (d, 2H), 7.94 (d, 2H), 8.20 (d, 1H), 13.74–14.05 (b, 1H).

EXAMPLE 23A
N-{1-[3-(3,5-Dimethoxyphenyl)-5-oxo-4,5-dihydro-1,2,4-triazin-6-yl]ethyl}acetamide

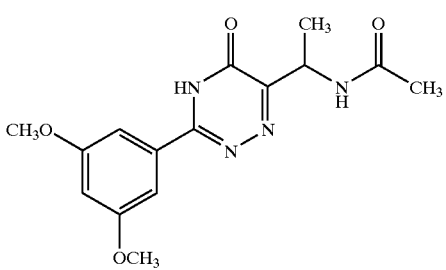

Preparation analogously to Example 21 A starting from Example 5A.

MS (ESI): 319 [M+H]+;

1H-NMR (400 MHz, DMSO-d6): δ=1.33 (d, 3H), 1.86 (s, 3H), 3.81 (s, 6H), 5.02 (m, 1H), 6.77 (t, 1H), 7.21 (s, 2H), 8.24 (d, 1H), 13.95–14.10 (b, 1H).

EXAMPLE 24A 2-(3,4-Dimethoxyphenyl)-5,7-dimethylimidazo[5,1-f][1,2,4]triazin-4(3H)-one

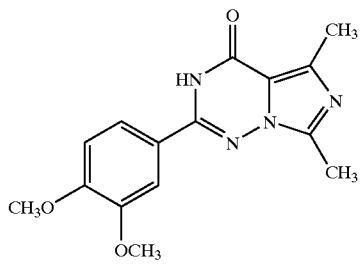

Example 11A (2.60 g, 8.13 mmol) is introduced into 100 ml of 1,2-dichloroethane and the solution is treated with 0.19 ml (2.04 mmol) of phosphoryl chloride. The batch is stirred at boiling heat for 24 h. After cooling, the precipitate is filtered off with suction, and the residue is washed with water (2×50 ml) and diethyl ether (50 ml) and dried.

Yield: 1.90 g (77% of theory)

1H-NMR (300 MHz, DMSO-d6): δ=2.55 (s, 3H), 2.64 (s, 3H), 3.84 (s, 3H), 3.86 (s, 3H), 7.13 (d, 1H), 7.58–7.62 (m, 1H), 7.64–7.71 (m, 1H).

EXAMPLE 25A

7-Cyclopentyl-2-(4-methoxyphenyl)-5-methylimidazo[5,1-f][1,2,4]triazin-4(3H)-one

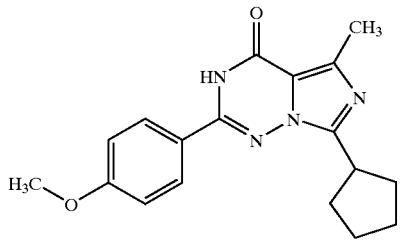

Example 14A (342 mg, 1.00 mmol) is introduced into 1,2-dichloroethane and the solution is treated with phosphoryl chloride (0.02 ml, 0.25 mmol). The batch is stirred at boiling heat for 5 h. After cooling, the reaction mixture is added to 50 ml of ice water and extracted by shaking with ethyl acetate (5×50 ml). The combined org. phases are dried (sodium sulphate), concentrated and purified by flash chromatography (eluent dichloromethane/methanol 40:1).

Yield: 180 mg (56% of theory)

1H-NMR (300 MHz, DMSO-d6): δ=1.55–2.12 (m, 8H), 3.56 (quint, 1H), 3.83 (s, 3H), 7.08 (d, 2H), 7.96 (d, 2H), 11.69 (s, 1H).

EXAMPLE 26A

7-Cyclopentyl-2-(3,4-dimethoxyphenyl)-5-methylimidazo[5,1-f][1,2,4]triazin-4(3H)-one

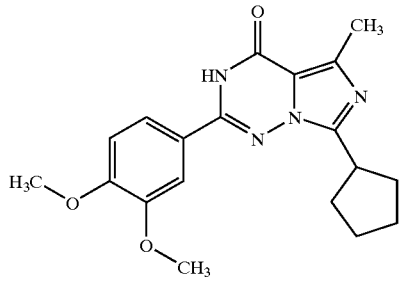

2.90 g (7.79 mmol) of Example 13A and 0.33 ml (3.50 mmol) of phosphoryl chloride are dissolved in 200 ml of 1,2-dichloroethane and the batch is stirred under reflux for 16 h. After cooling, the reaction mixture is added to 500 ml of ice water and extracted with dichloromethane. The combined organic phases are dried (sodium sulphate) and concentrated in vacuo. The residue is purified by flash chromatography (eluent dichloromethane/methanol 20:1).

Yield: 2.41 g (87% of theory)

1H-NMR (400 MHz, DMSO-d6): δ=1.66–2.21 (m, 8H), 2.59 (s, 3H), 3.55 (s, 3H), 3.58 (s, 3H), 3.72 (quint, 1H), 7.14 (d, 2H), 7.59 (s, 1H), 7.67 (d, 1H), 12.28 (s, 1H).

EXAMPLE 27A 2-(3,4-Dimethoxyphenyl)-5,7-dimethylimidazo[5,1-f][1,2,4]triazine-4(3H)-thione

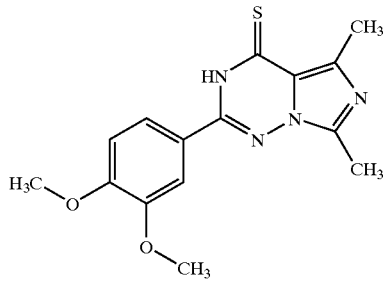

Phosphorus pentasulphide (666 mg, 3.00 mmol) and Example 24A (300 mg, 1.00 mmol) are dissolved in 20 ml of pyridine under argon and stirred under reflux for 24 h. After cooling, the reaction mixture is added to 50 ml of water and extracted with dichloromethane (3×100 ml). The combined organic phases are dried (sodium sulphate) and concentrated. The crude product is purified by flash chromatography (eluent dichloromethane/methanol 40:1 to 20:1). 198 mg (63% of theory) of product are obtained.

M.p.: 217° C.

1H-NMR (200 MHz, DMSO-d6): δ=2.53 (s, 3H), 2.68 (s, 3H), 3.84 (s, 3H), 3.87 (s, 3H), 7.11 (d, 1H), 7.52–7.72 (m, 2H), 12.73 (s, 1H).

EXAMPLE 28A

7-Cyclopentyl-2-(3,4-dimethoxyphenyl)-5-methylimidazo[5,1-f][1,2,4]triazine-4(3H)-thione

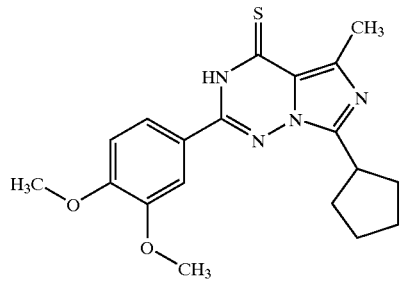

Preparation analogously to Example 27A from 150 mg (0.42 mmol) of Example 41A.

Yield: 134 mg (85% of theory)

M.p.: 209° C.

$^1$H-NMR (400 MHz, CDCl$_3$): δ=1.68–2.21 (m, 8H), 2.82 (s, 3H), 3.63 (quint, 1H), 3.97 (s, 3H), 3.99 (s, 3H), 6.98 (d, 1H), 7.37–7.41 (m, 2H), 9.15 (s, 1H)

EXAMPLE 29A

7-Cyclopentyl-2-[4-methoxy-3-(4-morpholinylsulphonyl)phenyl]-5-methylimidazo[5,1-f][1,2,4]triazin-4(3H)-one

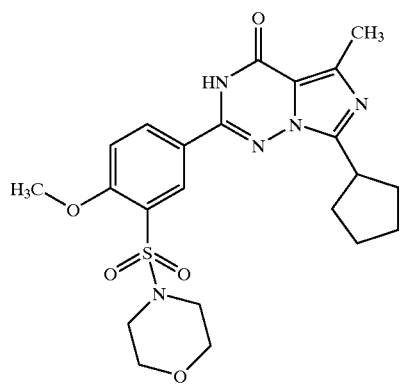

A solution of 130 mg (0.40 mmol) of Example 25A in 2 ml of dichloromethane is added dropwise under argon at 0° C. to 0.54 ml (8.02 mmol) of chlorosulphonic acid. The solution is stirred at RT for 1.5 h and then added dropwise to 20 g of ice. The mixture is extracted with dichloromethane (3×10 ml) and the combined organic phases are dried (sodium sulphate). Morpholine (0.07 ml, 0.80 mmol) is added to the solution and the batch is stirred at RT overnight. The reaction mixture is concentrated and the residue is purified by flash chromatography (eluent dichloromethane/methanol 80:1).

Yield: 103 mg (54% of theory)

$^1$H-NMR (300 MHz, CDCl$_3$): δ=1.65–2.23 (m, 8H), 2.65 (s, 3H), 3.23–3.36 (m, 4H), 3.64 (quint, 1H), 3.68–3.80 (m, 4H), 4.03 (s, 3H), 7.17 (d, 1H), 8.16–8.20 (m, 1H), 8.45 (d, 1H), 9.37 (s, 1H).

EXAMPLE 30A

7-Cyclopentyl-5-ethyl-2-(4-methoxyphenyl)imidazo[5,1-f][1,2,4]triazin-4(3H)-one

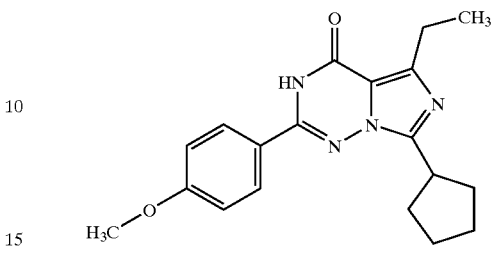

Preparation analogously to Example 26A.

$^1$H-NMR (300 MHz, DMSO-d$_6$): δ=1.22 (t, 3H), 1.56–2.14 (m, 8H), 2.88 (q, 2H), 3.58 (quint, 1H), 3.84 (s, 3H), 7.09 (d, 2H), 7.96 (d, 2H), 11.68 (s, 1H).

EXAMPLE 31A 5-(7-Cyclopentyl-5-ethyl-4-oxo-3,4-dihydroimidazo[5,1-f][1,2,4]triazin-2-yl)-2-methoxybenzenesulphonyl chloride

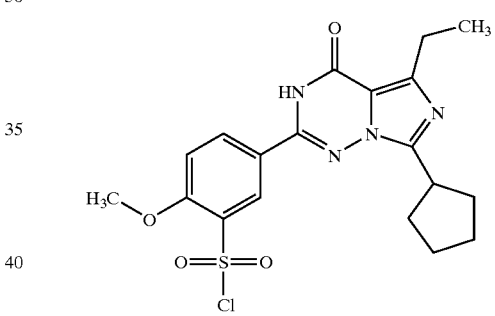

Example 30A (1.02 g, 3.00 mmol) is introduced in portions under argon into 20 ml of chlorosulphonic acid (ice-bath cooling) and stirred at RT for 2 h. The clear, yellowish solution is slowly introduced into about 500 ml of ice water in small portions and extracted with a mixture of ethyl acetate/THF 2:1 (2×200 ml each). The combined org. phases are dried (sodium sulphate), filtered and concentrated. 1.2 g (92% of theory) of crystalline product are obtained.

M.p.: 204° C.

$^1$H-NMR (200 MHz, DMSO-d$_6$): δ=1.30 (t, 3H), 1.57–2.29 (m, 8H), 3.04 (q, 2H), 3.74 (quint, 1H), 3.85 (s, 3H), 7.16 (d, 2H), 7.92–7.98 (m, 1H), 8.37 (d, 1H), 12.64 (s, 1H).

EXAMPLE 32A

7-Cyclopentyl-5-ethyl-2-[4-methoxy-3-(4-morpholinylsulphonyl)phenyl]-imidazo[5,1-f][1,2,4]triazin-4(3H)-one

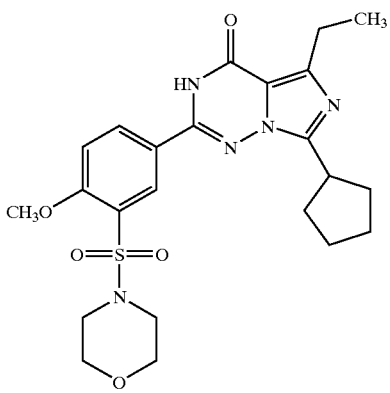

Example 31A (103 mg, 0.24 mmol) is dissolved in THF under argon and treated dropwise at RT with 0.08 ml (0.94 mmol) of morpholine. The mixture is stirred at RT for 15 h, diluted with 10 ml of ethyl acetate and washed with 2 N hydrochloric acid (about 10 ml). The organic phase is separated off, dried (sodium sulphate), filtered and concentrated to dryness. 130 mg of crystalline crude product are obtained.

The crude material is dissolved in ethyl acetate, added via a frit containing silica gel 60 (70–230 mesh), the filtrate is concentrated, and the crystalline residue is triturated with diethyl ether and filtered off with suction. The colourless solid is dried in a high vacuum.

Yield: 105 mg (91% of theory)

M.p.: 204° C.

$^1$H-NMR (300 MHz, CDCl$_3$): δ=1.34 (t, 3H), 1.51–2.23 (m, 8H), 3.05 (q, 2H), 3.24–3.36 (m, 4H), 3.65 (quint, 1H), 3.69–3.80 (m, 4H), 4.04 (s, 3H), 7.18 (d, 1H), 8.21–8.25 (m, 1H), 8.49 (d, 1H), 9.91 (s, 1H).

EXAMPLE 33A 2-(3–Chloro-4-methoxyphenyl)-5,7-dimethylimidazo[5,1-f][1,2,4]triazin-4(3H)-one

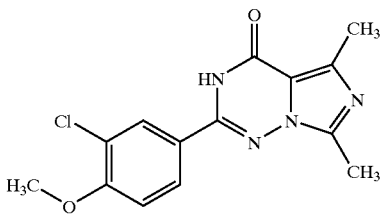

0.92 g (2.85 mmol) of Example 16A is suspended in 50 ml of dichloromethane and treated with 0.15 ml (1.57 mmol) of phosphoryl chloride. The mixture is stirred for 2 hours with boiling and concentrated. The evaporation residue is eluted through silica gel using dichloromethane/methanol 95:5. 283 mg (33% of theory) of slightly beige-coloured crystals are obtained.

MS (DCI/NH$_3$): 305 [M+H]$^+$;

$^1$H-NMR (300 MHz, DMSO-d$_6$): δ=2.45 (s, 6H), 3.94 (s, 3H), 7.31 (d, 1H), 8.00 (dd, 1H), 8.09 (d, 1H), 11.73 (s, 1H).

EXAMPLE 34A 2-(3-Chloro-4-methoxyphenyl)-7-isobutyl-5-methylimidazo[5,1-f][1,2,4]triazin-4(3H)-one

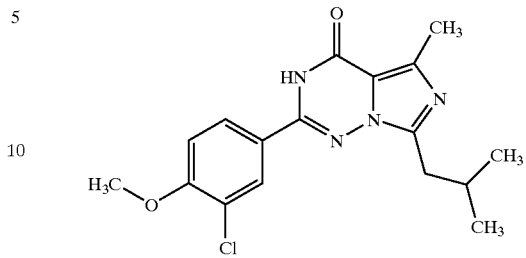

Preparation analogously to Example 26A from 250 mg (0.69 mmol) of Example 18A.

Yield: 190 mg (76% of theory)

$^1$H-NMR (200 MHz, DMSO-d$_6$): δ=0.94 (d, 6H), 2.07–2.26 (m, 1H), 3.55 (s, masked, 3H), 2.84 (d, 2H), 3.94 (s, 3H), 7.32 (d, 1H), 7.96–8.07 (m, 3H), 11.86 (s, br 1H).

EXAMPLE 35A 7-sec-Butyl-2-(3-chloro-4-methoxyphenyl)-5-methylimidazo[5,1-f][1,2,4]triazin-4(3H)-one

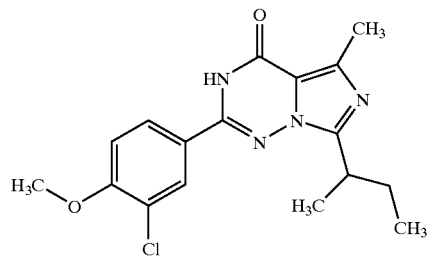

Preparation analogously to Example 26A from 295 mg (0.81 mmol) of Example 19A.

Yield: 240 mg (73% of theory)

$^1$H-NMR (200 MHz, DMSO-d$_6$): δ=0.83 (t, 3H), 1.33 (d, 3H), 1.61–1.93 (m, 2H), 2.54 (s, 3H), 3.31–3.54 (m, 1H), 3.95 (s, 3H), 7.33 (d, 1H), 7.97–8.02 (m, 2H), 8.09 (d, 1H), 12.06 (s, br 1H).

EXAMPLE 36A 2-(3-Chloro-4-methoxyphenyl)-7-(1-ethylpropyl)-5-methylimidazo[5,1-f][1,2,4]triazin-4(3H)-one

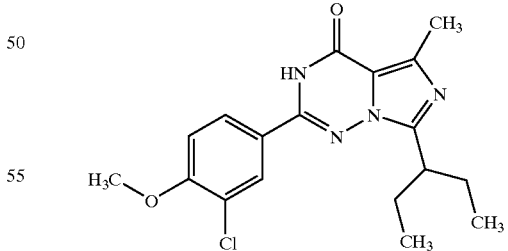

Preparation analogously to Example 26A from 317 mg (0.84 mmol) of Example 20A.

Yield: 240 mg (76% of theory)

M.p.: 228° C.

$^1$H-NMR (200 MHz, DMSO-d$_6$): δ=0.77 (t, 6H), 1.65–1.88 (m, 4H), 2.55 (s, masked, 3H), 3.11–3.32 (m, 1H), 3.95 (s, 3H), 7.33 (d, 1H), 7.95–8.01 (m, 1H), 8.08 (d, 1H), 11.92 (s, br 1H).

EXAMPLE 37A 2-(3,4-Dimethoxyphenyl)-5,7-dimethyl-4-(1H-1,2,4-triazol-1-yl)imidazo[5,1-f][1,2,4]triazine

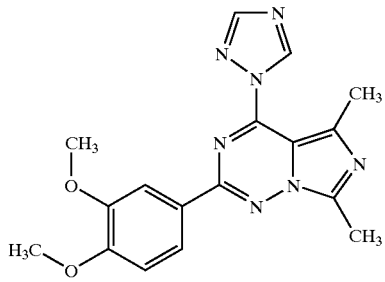

0.53 ml (879 mg, 5.67 mmol) of phosphoryl chloride are added dropwise under argon to a solution of 568 mg (1.89 mmol) of Example 24A in 80 ml of dry pyridine at 0° C. and the batch is stirred for 20 min. A solution of 3.33 g (47 mmol) of 1,2,4-triazole in 80 ml of dry pyridine is then added at 0° C. and the batch is stirred at RT for 16 h after addition is complete. The dark-red reaction mixture is concentrated, the residue is treated with 150 ml of ice water, and the mixture is extracted with dichloromethane (3×100 ml). The combined organic phases are dried (sodium sulphate) and the solvent is removed in vacuo. The residue is purified by flash chromatography (eluent dichloromethane/methanol 40:1). 238 mg (36% of theory) of product are obtained.

MS (ESI): 352 [M+H]$^+$ $^1$H-NMR (400 MHz, CDCl$_3$): δ=2.81 (s, 3H), 2.87 (s, 3H), 3.98 (s, 3H), 4.02 (s, 3H), 6.99 (d, 1H), 7.88 (d, 1H), 8.00 (q, 1H), 8.26 (s, 1H), 9.36 (s, 1H).

M.p.: 220° C.

EXAMPLE 38A

7-Cyclopentyl-2-(4-methoxyphenyl)-5-methyl-4-(1H-1,2,4-triazol-1-yl)imidazo[5,1-f][1,2,4]triazine

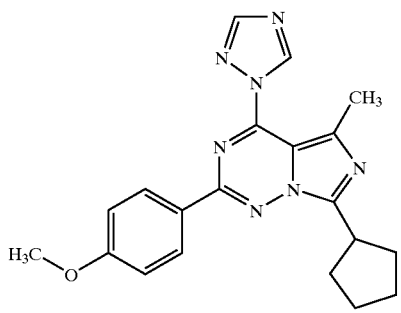

0.11 ml (124 mg, 1.15 mmol) of phosphoryl chloride is added dropwise to a solution of 124 mg (0.38 mmol) of Example 25A in 20 ml of dry pyridine at 0° C. and the batch is stirred for 20 min. A solution of 674 mg (9.56 mmol) of 1,2,4-triazole in 20 ml of dry pyridine is then added at 0° C. and the batch is stirred for 6 h at 50° C. after addition is complete. The solvent is removed in vacuo and the residue is treated with 50 ml of ice water. The mixture is extracted with dichloromethane (3×50 ml), the combined organic phases are dried (sodium sulphate), and the solvent is removed in vacuo. The residue is purified by flash chromatography (eluent dichloromethane/methanol 20:1).

Yield: 85 mg (59% of theory)
M.p.: 170° C.;
MS (ESI): 376 [M+H]$^+$;

$^1$H-NMR (400 MHz, DMSO-d$_6$): δ=1.67–2.20 (m, 8H), 2.71 (s, 3H), 3.80 (quint, 1H), 3.86 (s, 3H), 7.10 (d, 2H), 8.35 (d, 2H), 8.54 (s, 1H), 9.79 (s, 1H).

EXAMPLE 39A

Ethyl 2-[5-methyl-7-propyl-4-(1H-1,2,4-triazol-1-yl)imidazo[5,1-f][1,2,4]triazin-2-yl]phenyl ether

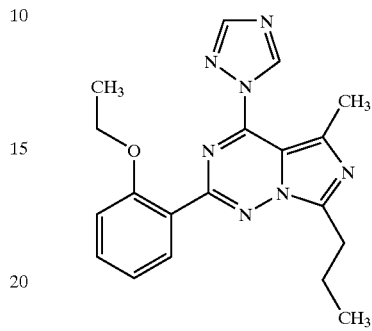

Preparation analogously to Example 37A from 2-(2-ethoxyphenyl)-5-methyl-7-propylimidazo[5,1-f][1,2,4]triazin-4(3H)-one (4.69 g, 15.0 mmol; preparation according to WO 99/24433).

Yield: 4.06 g (75% of theory) of yellow solid.
M.p.: 128–129° C.;
MS (ESI): 364 [M+H]$^+$;

$^1$H-NMR (400 MHz, CDCl$_3$): δ=1.05 (t, 3H), 1.43 (t, 3H), 1.93 (sex., 2H), 2.40 (s, 3H), 3.16 (t, 2H), 4.18 (quart., 2H), 7.08 (quart., 2H), 7.47 (m, 1H), 7.83 (dd, 1H), 8.23 (s, 1H), 9.28 (s, 1H).

EXAMPLE 40A 2-(3-Chloro-4-methoxyphenyl)-5,7-dimethyl-4-(1H-1,2,4-triazol-1-yl)imidazo[5,1-f][1,2,4]triazine

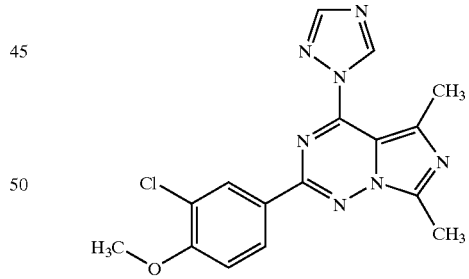

Preparation analogously to Example 37A from 98 mg (0.32 mmol) of Example 51A. Purification is carried out by column chromatography (eluent dichloromethane/methanol 95:5).

Yield: 57 mg (50% of theory) of solid.
M.p.: 258–259° C.;
MS (ESI): 356 [M+H]$^+$;

$^1$H-NMR (200 MHz, CDCl$_3$): δ=2.81 (s, 3H), 2.88 (s, 3H), 4.00 (s, 3H), 7.03 (d, 1H), 8.26 (m, 2H), 8.41 (d, 1H), 9.37 (s, 1H).

EXAMPLE 41A

7-Cyclopentyl-2-(3,4-dimethoxyphenyl)-5-methyl-4-(1H-1,2,4-triazol-1-yl)imidazo[5,1-f][1,2,4]triazine

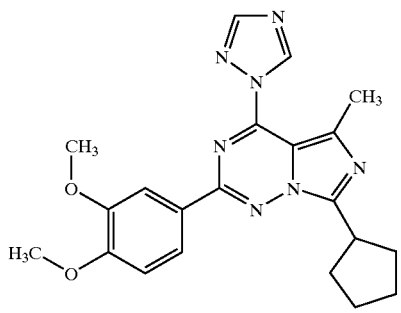

Preparation analogously to Example 37A from 3.96 g (11.2 mmol) of Example 26A.

Yield: 3.22 g (71% of theory)

M.p.: 194° C.;

MS (DCI): 406 [M+H]$^+$;

$^1$H-NMR (300 MHz, DMSO-d$_6$): δ=1.69–2.21 (m, 8H), 2.71 (s, 3H), 3.82 (quint, 1H), 3.86 (s, 3H), 3.90 (s, 3H), 7.13 (d, lH), 7.89 (d, 1H), 8.02 (q, 1H), 8.54 (s, 1H), 9.82 (s, 1H).

EXAMPLE 42A

7-Cyclopentyl-2-[4-methoxy-3-(4-morpholinylsulphonyl)phenyl]-5-methyl-4-(1H-1,2,4-triazol-1-yl)imidazo[5,1-f][1,2,4]triazine

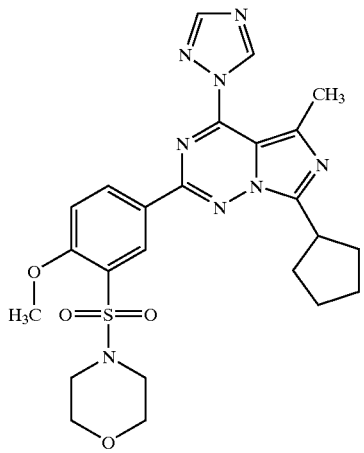

Preparation analogously to Example 37A from 97 mg (0.20 mmol) of Example 29A.

MS (ESI): 525 [M+H]$^+$;

$^1$H-NMR (200 MHz, CDCl$_3$): δ=1.70–2.33 (m, 8H), 2.88 (s, 3H), 3.24–3.37 (m, 4H), 3.70–3.80 (m, 4H), 3.85 (quint, 1H), 4.04 (s, 3H), 7.17 (d, 1H), 8.27 (s, 1H), 8.51–8.57 (m, 1H), 8.88 (d, 1H), 9.36 (s, 1H).

EXAMPLE 43A

7-Cyclopentyl-5-ethyl-2-[4-methoxy-3-(4-morpholinylsulphonyl)phenyl]-4-(1H-1,2,4-triazol-1-yl)imidazo[5,1-f][1,2,4]triazine

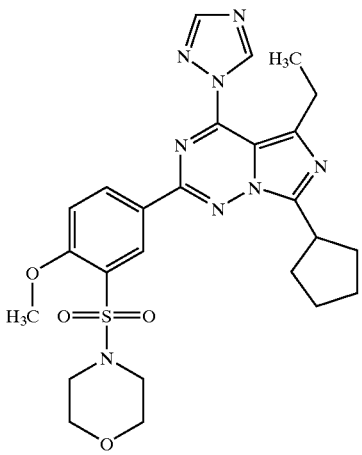

Preparation analogously to Example 37A from 700 mg (1.44 mmol) of Example 35A.

Yield: 772 mg (97% of theory), red-brown solid

MS (ESI): 539 [M+H]$^+$ $^1$H-NMR (300 MHz, CDCl$_3$): δ=1.24 (t, 3H), 1.73–2.27 (m, 8H), 3.24–3.36 (m, 6H), 3.71–3.78 (m, 4H), 3.85 (quint, 1H), 4.04 (s, 3H), 7.17 (d, 1H), 8.27 (s, 1H), 8.52–8.55 (m, 1H), 8.87 (d, 1H), 9.35 (s, 1H).

EXAMPLE 44A

4-[7-Cyclopentyl-5-ethyl-4-(1H-1,2,4-triazol-1-yl)imidazo[5,1-f][1,2,4]triazin-2-yl]phenyl methyl ether

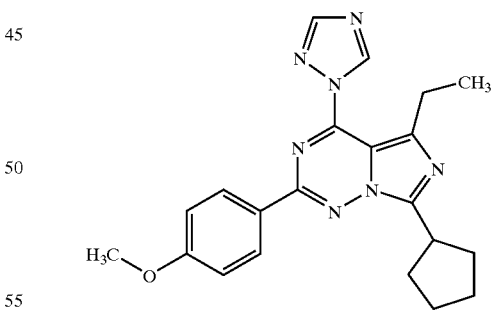

Preparation analogously to Example 37A from 605 mg (1.79 mmol) of Example 30A.

Yield: 636 mg (91% of theory)

MS (ESI): 390 [M+H]$^+$;

$^1$H-NMR (300 MHz, DMSO-d$_6$): δ=1.16 (t, 3H), 1.65–2.24 (m, 8H), 3.15 (q, 2H), 3.80 (quint, 1H), 3.86 (s, 3H), 7.11 (d, 2H), 8.35 (s, 2H), 8.55 (s, 1H), 9.79 (s, 1H).

EXAMPLE 45A 2-(3-Chloro-4-methoxyphenyl)-7-isobutyl-5-methyl-4-(1H-1,2,4-triazol-1-yl)imidazo-[5,1-f][1,2,4]triazine

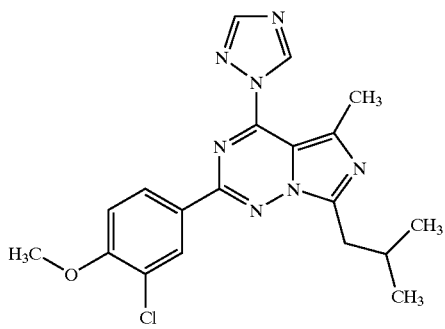

Preparation analogously to Example 37A from 175 mg (0.50 mmol) of Example 34A.

Yield: 54 mg (25% of theory)

M.p.: 193° C.;

MS (ESI): 398 [M+H]$^+$;

$^1$H-NMR (400 MHz, DMSO-d$_6$): δ=0.99 (d, 6H), 2.24–2.35 (m, 1H), 2.74 (s, 3H), 3.04 (d, 2H), 3.97 (s, 3H), 7.33 (d, 1H), 8.37 (q, 1H), 8.42 (d, 1H), 8.55 (s, 1H), 9.90 (s, 1H).

EXAMPLE 46A 7-sec-Butyl-2-(3-chloro-4-methoxyphenyl)-5-methyl-4-(1H-1,2,4-triazol-1-yl)-imidazo[5,1-f][1,2,4]triazine

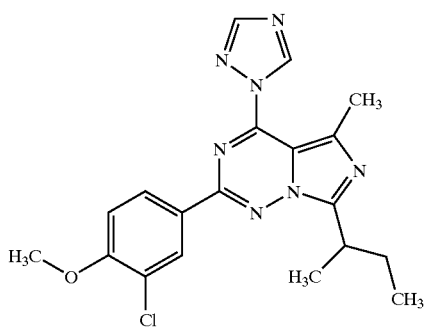

Preparation analogously to Example 37A from 220 mg (0.63 mmol) of Example 35A.

Yield: 118 mg (45% of theory)

M.p.: 227° C.;

MS (ESI): 347 [M+H]$^+$;

$^1$H-NMR (200 MHz, DMSO-d$_6$): δ=0.86 (t, 3H), 1.38 (d, 3H), 1.66–2.05 (m, 2H), 2.74 (s, 3H), 3.50–3.72 (m, 1H), 3.97 (s, 3H), 7.33 (d, 1H), 8.33–8.45 (m, 2H), 8.55 (s, 1H), 9.90 (s, 1H).

EXAMPLE 47A 2-(3Chloro-4-methoxyphenyl)-7-(1-ethylpropyl)-5-methyl-4-(1H-1,2,4-triazol-1-yl)-imidazo[5,1-f][1,2,4]triazine

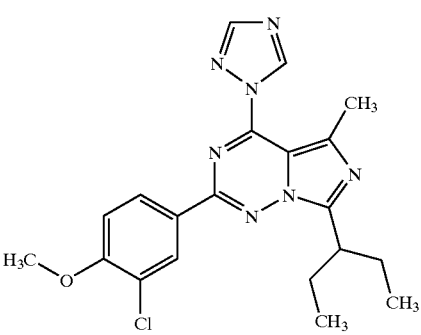

Preparation analogously to Example 37A from 229 mg (0.63 mmol) of Example 36A.

Yield: 150 mg (53% of theory)

M.p.: 197° C.;

MS (ESI): 412 [M+H]$^+$;

$^1$H-NMR (200 MHz, DMSO-d$_6$): δ=0.79 (t, 6H), 1.70–1.99 (m, 4H), 2.74 (s, 1H), 3.39–3.58 (m, 1H), 3.97 (s, 3H), 7.33 (d, 1H), 8.30–8.48 (m, 2H), 8.55 (s, 1H), 9.90 (s, 1H).

EXAMPLE 48A 2-(3,5-Dimethoxyphenyl)-5,7-dimethyl-4-(1H-1,2,4-triazol-1-yl)imidazo[5,1-f]-[1,2,4]triazine

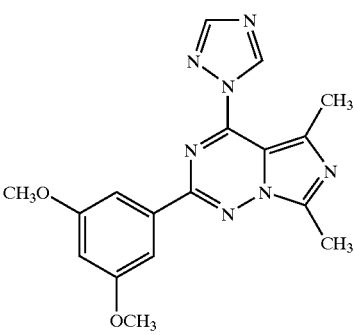

Preparation analogously to Example 37A.

M.p.: 203–205° C.;

MS (ESI): 305 [M+H]$^+$;

$^1$H-NMR (300 MHz, DMSO-d$_6$): δ=2.76 (d, 6H), 3.87 (s, 6H), 6.71 (t, 1H), 7.52 (d, 2H), 8.53 (s, 1H), 9.82 (s, 1H).

EXAMPLE 49A 5,7-Dimethyl-2-(4-methylphenyl)-4-(1H-1,2,4-triazol-1-yl)imidazo[5,1-f]-[1,2,4]triazine

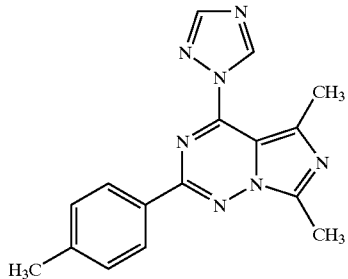

Preparation analogously to Example 37A.
M.p.: 190–191° C.;
MS (ESI): 305 (M)⁺;
¹H-NMR (200 MHz, DMSO-$d_6$): δ=2.41 (s, 3H), 2.72 (d, 6H), 7.36 (d, 2H), 8.30 (d, 2H), 8.53 (s, 1H), 9.83 (s, 1H).

EXAMPLE 50A 2-(4-Bromophenyl)-5,7-dimethyl-4-(1H-1,2,4-triazol-1-yl)imidazo[5,1-f][1,2,4]triazine

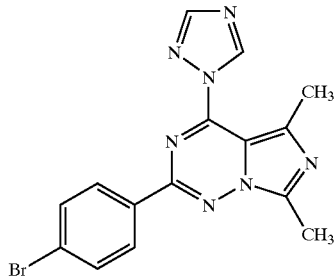

Preparation analogously to Example 37A.
MS (DCI/NH$_3$): 370 [M+H]⁺;
¹H-NMR (300 MHz, DMSO-$d_6$): δ=2.69 (s, 3H), 2.72 (s, 3H), 7.72 (m, 2H), 8.32 (m, 2H), 8.52 (s, 1H), 9.83 (s, 1H).

EXAMPLE 51A 2-(3-Chloro-4-methoxyphenyl)-5,7-dimethylimidazo[5,1-f][1,2,4]triazin-4(3H)-one

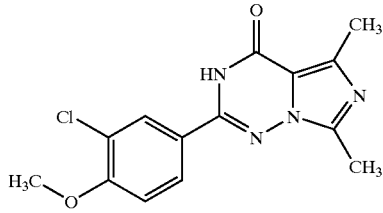

11.0 g (34.1 mmol) of open-chain N-acetyl compound are suspended in 598 ml of dichloroethane, then 7.84 g (51.2 mmol, 1.5 eq.) of phosphoryl chloride are added and the mixture is boiled under reflux for 2 hours. After TLC checking, 0.5 equivalent of phosphoryl chloride is added thereto again and the mixture is boiled further. Work-up is carried out by concentration of the batch on a rotary evaporator and addition of some methanol. The precipitated beige solid is filtered off with suction, washed with a little methanol and dried (4.52 g). 200 mg of the crystals are chromatographed on 30 g of silica gel 60 using methylene chloride/methanol (97:3) and afford 52 mg of product.

MS (DCI/NH$_3$): m/z=305 [M+H]⁺;

¹H-NMR (300 MHz, DMSO-$d_6$): δ=2.45 (s, 6H), 3.94 (s, 3H), 7.31 (d, 1H), 8.00 (dd, 1H), 8.09 (d, 1H), 11.73 (s, 1H).

EXAMPLE 52A 5,7-Dimethyl-2-(4-methylphenyl)imidazo[5,1-f][1,2,4]triazin-4(3H)-one

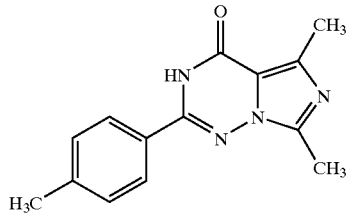

5 g (18.4 mmol) of open-chain N-acetyl compound are dissolved in 150 ml of dichloroethane and boiled under reflux for 2 hours with 4.22 g (27.5 mmol, 1.5 eq.) of phosphoryl chloride. Work-up is carried out by concentrating the batch on a rotary evaporator. The residue is chromatographed on 25 g of silica gel 60 using methylene chloride/methanol (95:5) and, after drying in a high vacuum, 4 g of product (83% of theory) are obtained.

MS (ESI): m/z=255 [M+H]⁺;

¹H-NMR (200 MHz, DMSO-$d_6$): δ=2.41 (s, 3H), 2.48 (s, 3H), 2.72 (s, 3H), 7.40 (d, 2H), 7.80 (d, 2H), 12.50 (s, 1H).

EXAMPLE 53A 2-(3,5-Dimethoxyphenyl)-5,7-dimethylimidazo[5,1-f][1,2,4]triazin-4(3H)-one

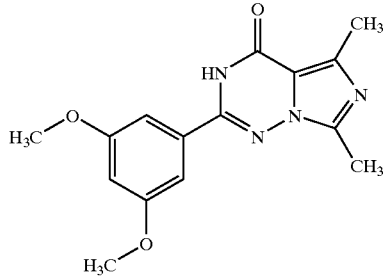

6.33 g (19.9 mmol) of open-chain N-acetyl compound are dissolved in 234 ml of dichloroethane and boiled under reflux for 2 hours with 4.58 g (29.8 mmol, 1.5 eq.) of phosphoryl chloride. After cooling, the deposited precipitate is washed with dichloroethane and suspended in methanol, acetone, ethyl acetate and isolated again. After drying in a high vacuum, 5.83 g of product (92% of theory) result.

MS (ESI): m/z=301 [M+H]⁺;

¹H-NMR (300 MHz, DMSO-$d_6$): δ=2.61 (s, 3H), 2.71 (s, 3H), 3.81 (s, 6H), 6.77 (t, 1H), 7.20 (d, 2H), 12.35–12.52 (b, 1H).

PREPARATION EXAMPLES

Example 1
2-(3,4-Dimethoxyphenyl)-5,7-dimethyl-N-(3,4,5-trimethoxyphenyl)imidazo[5,1-f]-[1,2,4]triazin-4-amine

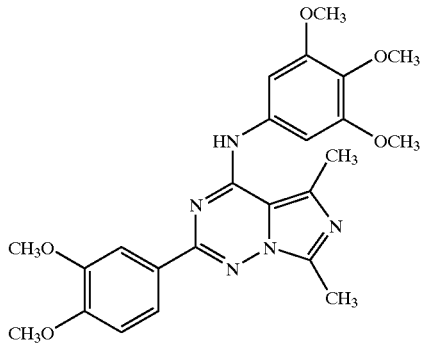

30 mg (0.09 mmol) of Example 37A are introduced into 2 ml of pyridine and treated with a solution of 180 mg (0.96 mmol) of 3,4,5-trimethoxyaniline in 4 ml of pyridine. The reaction mixture is stirred under reflux overnight. After cooling, the solvent is removed on a rotary evaporator and the crude product is purified by HPLC (eluent: acetonitrile-water mixture).

Yield: 20 mg (46% of theory)
M.p.: 226° C.;
$^1$H-NMR (300 MHz, DMSO-$d_6$): δ=2.59 (s, 3H), 2.68 (s, 3H), 3.68 (s, 3H), 3.78 (s, 3H), 3.81 (s, 9H), 7.07 (d, 1H), 7.21 (s, 2H), 7.76 (d, 1H), 7.84 (q, 1H), 8.79 (s, 1H).

Example 2
2-(3,4-Dimethoxyphenyl)-5,7-dimethyl-4-[(2-methyl-3-furyl)sulphanyl]imidazo[5,1-f]-[1,2,4]triazine

180.5 mg (1.42 mmol) of 2-methyl-3-furanthiol (about 90% strength) and 0.32 ml (352 mg, 1.57 mmol) of 15-crown-5 are added to a suspension of 58 mg (1.45 mmol) of sodium hydride (60% strength in paraffin) in 5 ml of dry THF and the batch is stirred for 15 min. A solution of 100 mg (0.28 mmol) of Example 37A in 10 ml of dry THF and 3 ml of dry dichloromethane is added and the reaction mixture is stirred at 70° C. for 27 h. After cooling, the solvent is removed on a rotary evaporator and the crude material is purified by HPLC.

Yield: 28 mg (25% of theory)
M.p.: 156° C.;
$^1$H-NMR (200 MHz, DMSO-$d_6$): δ=2.33 (s, 3H), 2.62 (s, 3H), 2.68 (s, 3H), 3.75 (s, 3H), 3.81 (s, 1H), 6.73 (d, 1H), 7.04 (d, 1H), 7.60 (d, 1H), 7.71 (q, 1H), 7.84 (s, 1H).

Example 3
N-(3,5-Dimethoxybenzyl)-2-(3,4-dimethoxyphenyl)-5,7-dimethylimidazo[5,1-f]-[1,2,4]triazin-4-amine

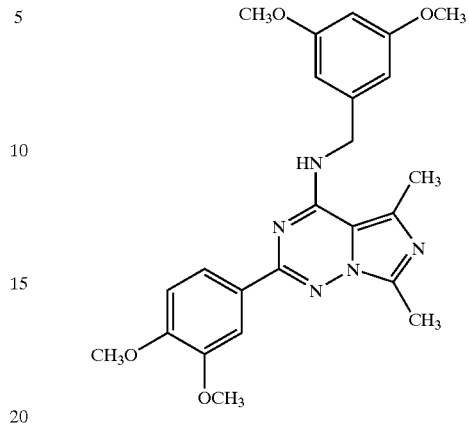

Prepared analogously to Example 1 from Example 37A (80 mg, 0.23 mmol) and 3,5-dimethoxybenzylamine (396 mg, 2.32 mmol). Purification is carried out by flash chromatography (eluent dichloromethane/methanol 80:1).

Yield: 86 mg (84% of theory)
M.p.: 174° C.;
$^1$H-NMR (300 MHz, CDCl$_3$): δ=2.61 (s, 3H), 2.68 (s, 3H), 3.77 (s, 6H), 3.94 (s, 3H), 3.97 (s, 3H), 4.90 (d, 2H), 5.68 (t, 2H), 6.40 (t, 1H), 6.57–6.63 (m, 3H), 6.93 (d, 2H), 7.86–7.91 (m, 1H), 7.94–8.03 (m, 1H).

Example 4
2-(3,4-Dimethoxyphenyl)-5,7-dimethyl-4-[(3-pyridinylmethyl)sulphanyl]imidazo-[5,1-f][1,2,4]triazine

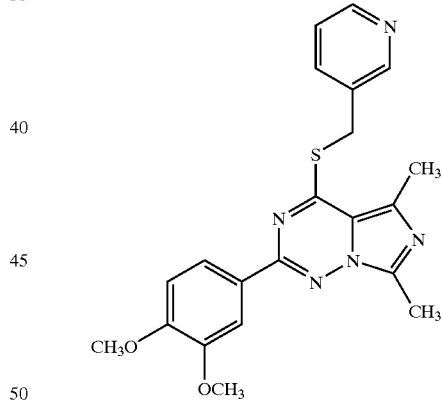

A solution of Example 27A (50 mg, 0.16 mmol) in 5 ml of DMSO is added to 5 ml of a saturated sodium hydrogencarbonate solution. 80 mg (0.32 mmol) of 3-picolyl bromide hydrobromide are then added and the reaction mixture is stirred at 60° C. overnight. After cooling, the batch is poured onto 50 ml of dichloromethane and washed with water (3×50 ml). The organic phase is dried (sodium sulphate) and the solvent is removed in vacuo. The crude material obtained is purified by flash chromatography (eluent dichloromethane/methanol 20:1).

M.p.: 161° C.;
MS (ESI): 409 [M+H]$^+$;
$^1$H-NMR (200 MHz, CDCl$_3$): δ=2.68 (s, 3H), 2.72 (s, 3H), 3.95 (s, 3H), 3.96 (s, 3H), 4.71 (s, 2H), 6.96 (d, 1H), 7.17–7.31 (m, 1H), 7.75–7.90 (m, 3H), 7.95–8.04 (m, 1H), 8.53 (d, 1H), 8.74 (s, 1H).

Example 5
7-Cyclopentyl-2-(4-methoxyphenyl)-5-methyl-N-(3,4,5-trimethoxyphenyl)imidazo-[5,1-f][1,2,4]triazin-4-amine

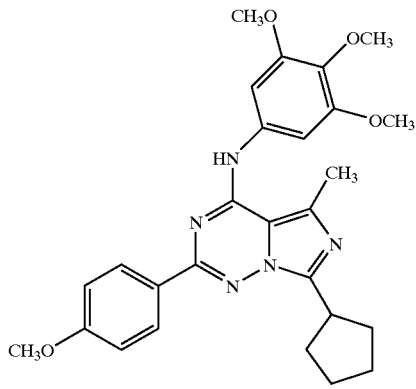

Preparation analogously to Example 1 from 60 mg (0.16 mmol) of Example 38A and 308 mg (1.63 mmol) of 3,4,5-trimethoxyaniline. Purification is carried out by flash chromatography (eluent dichloromethane/methanol 80:1) and recrystallisation from pentane/dichloromethane.

Yield: 46 mg (59% of theory)
M.p.: 180° C.;
$^1$H-NMR (200 MHz, CDCl$_3$): δ=1.65–2.31 (m, 8H), 2.79 (s, 3H), 3.75 (quint, 1H), 3.88 (s, 6H), 3.94 (s, 6H), 6.95 (d, 2H), 7.04 (s, 1H), 7.13 (s, 2H), 8.29 (d, 2H).

Example 6
7-Cyclopentyl-2-(3,4-dimethoxyphenyl)-5-methyl-N-(3,4,5-trimethoxyphenyl)-imidazo[5,1-f][1,2,4]triazin-4-amine

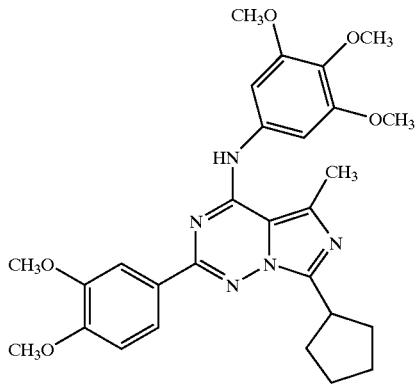

Example 41A (400 mg, 0.99 mmol) and 3,4,5-dimethoxyaniline (373 mg, 1.97 mmol) are dissolved in 5 ml of diglyme and the batch is stirred at 170° C. for 16 h. After cooling, the dark-brown solution is treated with 50 ml each of water and dichloromethane and the organic phase is separated off. This was washed with water (4×30 ml) and 2N hydrochloric acid (50 ml), dried (sodium sulphate), and concentrated. The crude product is flash-chromatographed (eluent dichloro-methane/methanol 25:1). The product is obtained as a viscous oil, which is triturated with diethyl ether, concentrated again, and dried in a high vacuum. 197 mg (38% of theory) of colourless crystals are obtained.

M.p.: 164° C.;
$^1$H-NMR (200 MHz, CDCl$_3$): δ=1.66–2.92 (m, 8H), 3.64–3.86 (m, 1H), 3.88 (s, 3H), 3.93 (s, 6H), 3.95 (s, 3H), 3.96 (s, 3H), 6.90 (d, 1H), 7.06 (d, 1H), 7.09 (s, 1H), 7.84–7.89 (m, 1H), 7.92–8.01 (m, 1H).

Example 7
N-(2-Bromophenyl)-2-(3,4-dimethoxyphenyl)-5,7-dimethylimidazo[5,1-f]-[1,2,4]triazin-4-amine

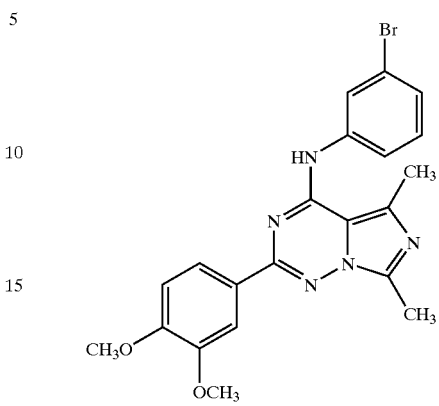

Preparation analogously to Example 1 from 54 mg (0.15 mmol) of Example 38A and 275 mg (1.57 mmol) of 2-bromoaniline. Purification is carried out by flash chromatography (eluent dichloromethane/methanol 80:1).

Yield: 28 mg (40% of theory)
M.p.: 187° C.;
MS (EI): 455 [M+H]$^+$;
$^1$H-NMR (300 MHz, CDCl$_3$): δ=2.72 (s, 3H), 2.87 (s, 3H), 3.96 (s, 3H), 4.00 (s, 3H), 6.98 (d, 1H), 7.02–7.10 (m, 1H), 7.37–7.46 (m, 1H), 7.62–7.68 (m, 1H), 7.85 (s, 1H), 7.89–7.99 (m, 2H), 8.89–8.99 (m, 1H).

Example 8
N-(2-Bromophenyl)-7-cyclopentyl-2-(3,4-dimethoxyphenyl)-5-methylimidazo[5,1-f]-[1,2,4]triazin-4-amine

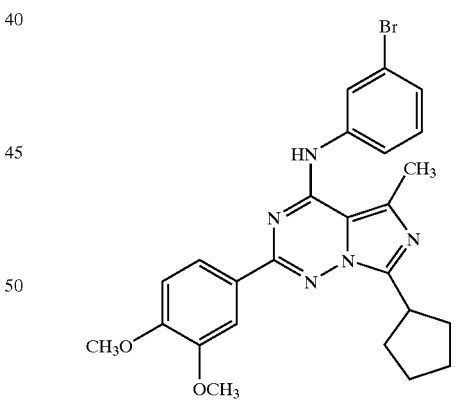

80 mg (0.20 mmol) of Example 41A and 68 mg (0.39 mmol) of 2-bromoaniline are dissolved in 10 ml of THF and the batch is stirred at 70° C. for 4 h. After cooling, the solvent is removed and the residue is purified by flash chromatography (eluent dichloromethane/methanol 80:1). 79 mg (79% of theory) of product are obtained.

M.p.: 159° C.;
$^1$H-NMR (400 MHz, CDCl$_3$): δ=1.70–2.26 (m, 8H), 2.88 (s, 3H), 3.76 (quint, 1H), 3.96 (s, 3H), 4.00 (s, 3H), 6.97 (d, 1H), 7.01–7.08 (m, 1H), 7.38–7.46 (m, 1H), 7.62–7.67 (m, 1H), 7.85 (s, 1H), 7.89–7.97 (m, 2H), 8.90–8.97 (m, 1H)

Example 9
7-Cyclopentyl-2-(3,4-dimethoxyphenyl)-5-methyl-4-[(2-methyl-3-furyl)sulphanyl]-imidazo[5,1-f][1,2,4]triazine

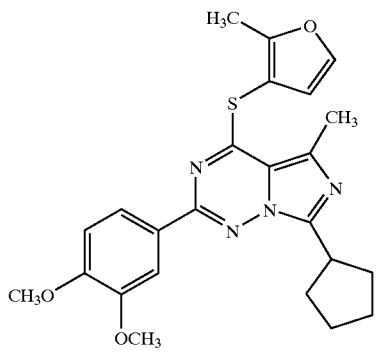

50 mg (0.39 mmol) of 2-methyl-3-furanthiol (about 90% strength) are added to a suspension of 16 mg (0.39 mmol) of sodium hydride (60% strength in paraffin) in 3 ml of dry THF and the batch is stirred for 15 min. A solution of 80 mg (0.20 mmol) of Example 41A in 7 ml of dry THF is added and the reaction mixture is stirred at 70° C. for 4 h. After cooling, the solvent is removed on a rotary evaporator and the crude material is purified by flash chromatography (eluent dichloromethane/methanol 80:1).

Yield: 74 mg (83% of theory)

M.p.: 139° C.;

$^1$H-NMR (400 MHz, CDCl$_3$): δ=1.69–2.23 (m, 8H), 2.37 (s, 3H), 2.81 (s, 3H), 3.75 (quint, 1H), 3.88 (s, 3H), 3.93 (s, 3H), 6.54 (d, 1H), 6.89 (d, 1H), 6.46 (d, 1H), 7.67 (d, 1H), 7.77–7.81 (m, 1H).

Example 10
2-(3,4-Dimethoxyphenyl)-N-(4-methoxyphenyl)-5,7-dimethylimidazo[5,1-f]-[1,2,4]triazin-4-amine

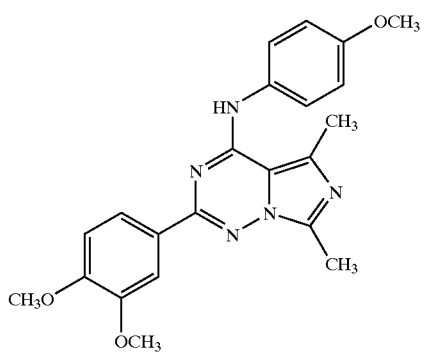

Example 37A (117 mg, 0.33 mol) and 4-methoxyaniline (62 mg, 0.50 mmol) are stirred at 170° C. overnight in 10 ml of diglyme. After cooling, the batch is treated with 50 ml of water, and the deposited precipitate is filtered off with suction. The solid obtained is taken up in 20 ml of dichloromethane, the organic phase is washed with 20 ml of water, dried (sodium sulphate) and concentrated. The dark residue obtained is suspended in ether and filtered off with suction. A colourless solid is obtained, which is dried in a high vacuum.

Yield: 82 mg (61% of theory)

M.p.: 151° C.;

$^1$H-NMR (200 MHz, CDCl$_3$): δ=2.70 (s, 3H), 2.75 (s, 3H), 3.85 (s, 3H), 3.94 (s, 3H), 3.97 (s, 3H), 6.82–7.10 (m, 4H), 7.61–7.75 (m, 2H), 7.85–7.99 (m, 2H).

Example 11
7-Cyclopentyl-2-(3,4-dimethoxyphenyl)-N-[2-(3,4-dimethoxyphenyl)ethyl]-5-methylimidazo[5,1-f][1,2,4]triazin-4-amine

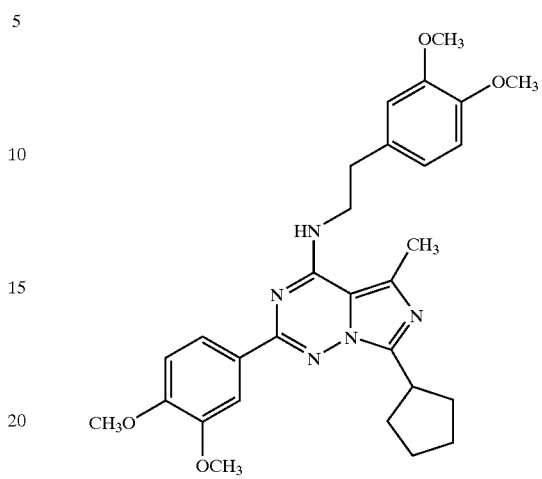

Example 41A (82 mg, 0.20 mmol) and 2-(3,4-dimethoxyphenyl)ethylamine (73 mg, 0.40 mmol) are stirred at boiling heat for 18 h in 10 ml of dioxane. After cooling, the solvent is removed in vacuo and the crude product is purified by flash chromatography (eluent gradient cyclohexane-cyclohexane/ethyl acetate 2:1). Yield: 76 mg (73% of theory)

MS (ESI): 518 [M+H]$^+$;

$^1$H-NMR (200 MHz, CDCl$_3$): δ=0.79–0.93 (m, 2H), 1.62–2.25 (m, 8H), 2.46 (s, 3H), 3.00 (t, 2H), 3.71 (quint, 1H), 3.86 (s, 3H), 3.88 (s, 3H), 3.95 (s, 3H), 3.99 (s, 3H), 5.39 (t, 1H), 6.72–6.89 (m, 3H), 6.95 (d, 1H), 7.91 (d, 1H), 7.96–8.01 (m, 1H).

Example 12
7-Cyclopentyl-2-(3,4-dimethoxyphenyl)-5-methyl-4-[(3-pyridinylmethyl)sulphanyl]-imidazo[5,1-f][1,2,4]triazine

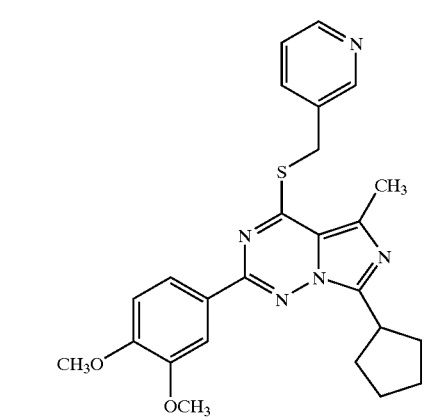

Preparation analogously to Example 4 from 55 mg (0.15 mmol) of Example 28A and 75 mg (0.30 mmol) of 3-picolyl bromide hydrobromide. Purification is carried out by flash chromatography (eluent dichloromethane/methanol 40:1).

Yield: 55 mg (80% of theory)

M.p.: 143° C.;

$^1$H-NMR (400 MHz, CDCl$_3$): δ=1.69–2.23 (m, 8H), 2.69 (s, 3H), 3.73 (quint, 1H), 3.94 (s, 3H), 3.95 (s, 3H), 4.70 (s, 2H), 6.96 (d, 1H), 7.20–7.30 (m, 1H), 7.78–7.83 (m, 1H), 7.84–7.87 (m, 1H), 7.94–8.00 (m, 1H), 8.52 (d, 1H), 8.74 (s, 1H).

Example 13
N-(3–Chloro-4-methoxyphenyl)-2-(3,4-dimethoxyphenyl)-5,7-dimethylimidazo [5,1-f][1,2,4]triazin-4-amine

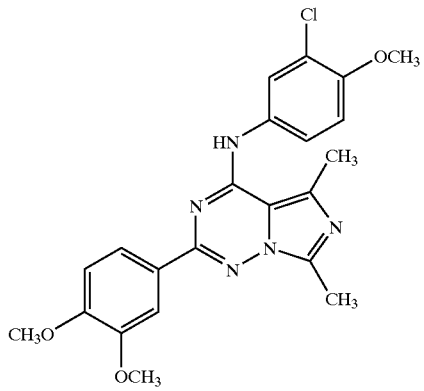

65 mg (0.18 mmol) of Example 37A and 162 mg (0.92 mmol) of 3-chloroanisidine are reacted analogously to Example 14. The reaction time is 48 h. The crude material is purified by HPLC (eluent acetonitrile-water mixture). In addition to the desired product (30 mg, 37% of theory), a further 17% of Example 37A are recovered.

M.p.: 195° C.;
MS (ESI): 440 [M+H]$^+$
$^1$H-NMR (300 MHz, CDCl$_3$): δ=2.71 (s, 3H), 2.76 (s, 3H), 3.94 (s, 3H), 3.95 (s, 3H), 4.00 (s, 3H), 6.89–7.03 (m, 2H), 7.17–7.32 (m, 1H), 7.36–7.45 (m, 1H), 7.85–7.97 (m, 2H), 8.14 (d, 1H).

Example 14
2-(3,4-Dimethoxyphenyl)-N-(4-methoxy-3,5-dimethylphenyl)-5,7-dimethylimidazo-[5,1-f][1,2,4]triazin-4-amine

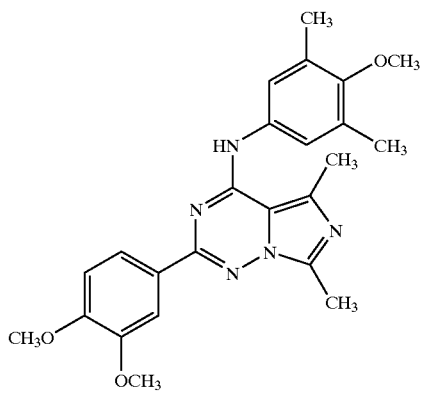

67 mg (0.19 mmol) of Example 37A and 144 mg (0.95 mmol) of 4-methoxy-3,5-dimethylaniline are heated under reflux overnight in 10 ml of pyridine. After cooling, the reaction solution is diluted with 50 ml of dichloromethane and washed with 1 N hydrochloric acid (3×50 ml), saturated sodium hydrogencarbonate solution (2×50 ml), and water (50 ml). After drying over sodium sulphate, the solvent is removed in vacuo. Purification is carried out by flash chromatography (eluent dichloromethane/methanol 100:1).

Yield: 32 mg (38% of theory), in addition 25% of Example 37A are recovered.

M.p.: 173° C.;
MS (ESI): 434 [M+H]$^+$;
$^1$H-NMR (400 MHz, CDCl$_3$): δ=2.35 (s, 3H), 2.70 (s, 3H), 2.75 (s, 3H), 3.75 (s, 3H), 3.95 (s, 3H), 3.99 (s, 3H), 6.95 (d, 1H), 6.99 (s, 1H), 7.48 (s, 2H), 7.88–7.91 (m, 1H), 7.94–7.98 (m, 1H).

Example 15
7-Cyclopentyl-2-(3,4-dimethoxyphenyl)-N-(4-methoxy-3,5-dimethylphenyl)-5-methylimidazo[5,1-f][1,2,4]triazin-4-amine

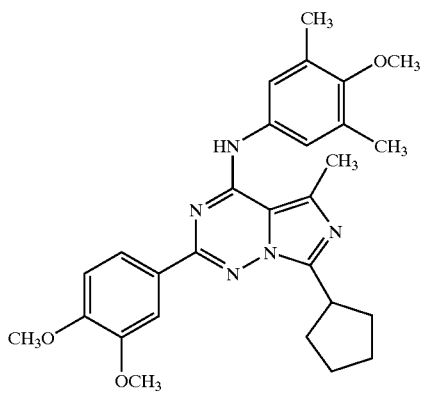

Analogously to Example 14, 80 mg (0.20 mmol) of Example 41A and 149 mg (0.99 mmol) of 4-methoxy-3,5-dimethylaniline are reacted. After flash-chromatographic purification (eluent dichloromethane/methanol 80:1), 15% of Example 4 1A are recovered and 57 mg (59% of theory) of product are obtained.

M.p.: 180° C.;
MS (ESI): 488 [M+H]$^+$;
$^1$H-NMR (300 MHz, CDCl$_3$): δ=1.67–2.26 (m, 8H), 2.35 (s, 6H), 2.76 (s, 3H), 3.75 (s, 3H), 3.75 (quint, 1H), 3.95 (s, 3H), 3.98 (s, 3H), 6.95 (d, 1H), 6.98 (s, 1H), 7.47 (s, 2H), 7.86–7.97 (m, 2H).

Example 16
N-(3–Chloro-4-methoxyphenyl)-7-cyclopentyl-2-(3,4-dimethoxyphenyl)-5-methyl-imidazo[5,1-f][1,2,4]triazin-4-amine

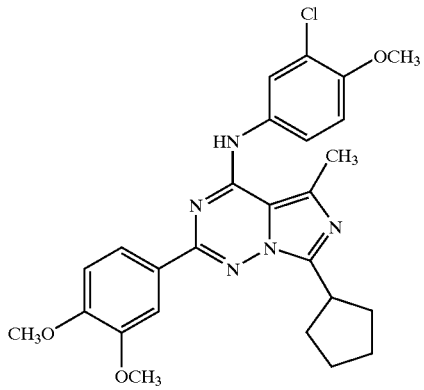

Example 41A (78 mg, 0.19 mmol) is introduced into 15 ml of DMSO, 3-chloro-p-anisidine (168 mg, 0.96 mmol) and potassium fluoride (23 mg, 0.38 mmol) are added and the reaction mixture is heated under reflux overnight. After cooling, the batch is poured onto 100 ml of dichloromethane and washed with saturated sodium chloride solution (3×50 ml). The combined org. phases are dried (sodium sulphate) and concentrated. The crude product is purified by HPLC.

27 mg (28% of theory) of a solid are obtained.

M.p.: 107° C.;

MS (ESI): 494 [M+H]$^+$;

$^1$H-NMR (300 MHz, CDCl$_3$): δ=1.69–2.25 (m, 8H), 2.77 (s, 3H), 3.75 (quint, 1H), 3.94 (s, 3H), 3.95 (s, 3H), 4.00 (s, 3H), 6.92–7.02 (m, 2H), 7.38–7.45 (m, 1H), 7.86–7.95 (m, 2H), 8.15 (d, 1H).

Example 17
7-Cyclopentyl-2-(3,4-dimethoxyphenyl)-5-methyl-N-(3,4,5-trimethoxybenzyl)-imidazo[5,1-f][1,2,4]triazin-4-amine

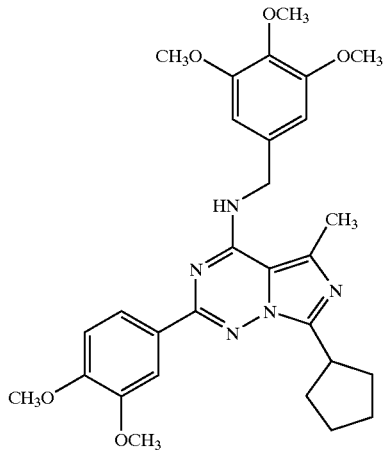

Preparation is carried out analogously to Example 11 from 81 mg (0.20 mmol) of Example 41A and 197 mg (0.40 mmol) of 3,4,5-trimethoxybenzylamine. The crude product is purified by flash chromatography (eluent gradient dichloromethane-dichloromethane/methanol 30:1). The solid obtained is suspended in a little diethyl ether/pentane mixture and filtered off with suction.

Yield: 75 mg (68% of theory)

M.p.: 188° C.;

MS (ESI): 534 [M+H]$^+$;

$^1$H-NMR (300 MHz, CDCl$_3$): δ=1.59–2.12 (m, 8H), 2.60 (s, 3H), 3.60 (s, 3H), 3.63 (quint, 1H), 3.70 (s, 6H), 3.79 (s, 3H), 3.81 (s, 3H), 4.76 (d, 2H), 6.82 (s, 2H), 7.03 (d, 1H), 7.70–7.90 (m, 2H), 7.98 (t, 1H).

Example 18
N-[7-Cyclopentyl-2-(3,4-dimethoxyphenyl)-5-methylimidazo[5,1-f][1,2,4]triazin-4-yl]-N-(2,4-dimethoxyphenyl)amine

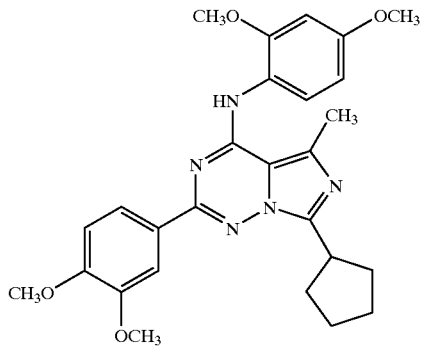

81 mg (0.20 mmol) of Example 41A and 37 mg (0.24 mmol) of 2,4-dimethoxyaniline are stirred at 100° C. for 16 h in 5 ml of THF. After cooling, the mixture is concentrated and purified by flash chromatography (eluent gradient cyclohexane-cyclohexane/ethyl acetate 1:1), then by HPLC.

Yield: 29 mg (30% of theory)

M.p.: 244° C.;

MS (ESI): 490 [M+H]$^+$;

$^1$H-NMR (200 MHz, CDCl$_3$): δ=1.55–2.24 (m, 8H), 3.08 (s, 3H), 3.81–4.09 (m, 1H), 3.88 (s, 3H), 3.98 (s, 6H), 4.00 (s, 3H), 6.58–6.67 (m, 2H), 7.01 (d, 1H), 7.82–8.06 (m, 3H), 8.64 (d, 1H).

Example 19
7-Cyclopentyl-2-(3,4-dimethoxyphenyl)-5-methyl-4-(3,4,5-trimethoxyphenoxy)-imidazo[5,1-f][1,2,4]triazine

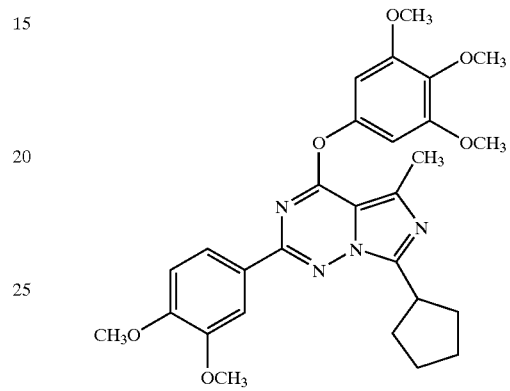

Synthesis is carried out analogously to Example 22 from 80 mg (0.20 mmol) of Example 41A and 73 mg (0.39 mmol) of 3,4,5-trimethoxyphenol.

Yield: 47 mg (46% of theory)

M.p.: 144° C.;

$^1$H-NMR (200 MHz, CDCl$_3$): δ=1.65–2.30 (m, 8H), 2.73 (s, 3H), 3.77 (quint, 1H), 3.87 (s, 9H), 3.88 (s, 3H), 3.92 (s, 3H), 6.60 (s, 2H), 6.87 (d, 1H), 7.64–7.81 (m, 2H).

Example 20
7-Cyclopentyl-2-(3,4-dimethoxyphenyl)-N-(4-methoxyphenyl)-5-methylimidazo-[5,1-f][1,2,4]triazin-4-amine

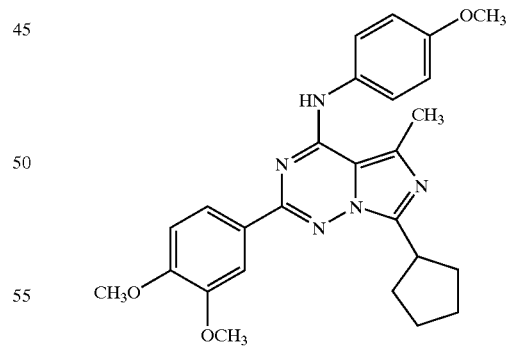

Synthesis is carried out analogously to Example 10 from 150 mg (0.37 mmol) of Example 41A and 68 mg (0.55 mmol) of 4-methoxyaniline.

Yield: 78 mg (46% of theory) of colourless solid

M.p.: 185° C.;

MS (ESI): 460 [M+H]$^+$ $^1$H-NMR (300 MHz, CDCl$_3$): δ=1.69–2.25 (m, 8H), 2.76 (s, 3H), 3.74 (quint, 1H), 3.85 (s, 3H), 3.94 (s, 3H), 3.96 (s, 3H), 6.88–7.07 (m, 3H), 7.78 (d, 2H), 7.83–7.94 (m, 2H).

Example 21
7-Cyclopentyl-N,2-bis(3,4-dimethoxyphenyl)-5-methylimidazo[5,1-f][1,2,4]triazin-4-amine

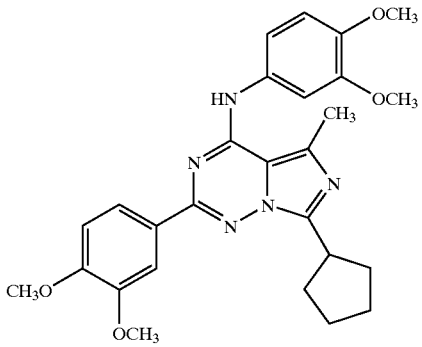

A solution of 100 mg (0.25 mmol) of Example 41A and 57 mg (0.37 mmol) of 4-aminoveratrole in 10 ml of dioxane is heated under reflux for 30 h. After cooling, the solvent is removed in vacuo and the residue is prepurified by flash chromatography (eluent dichloromethane/methanol 30:1). Preparative TLC affords 23 mg (19% of theory) of product.
M.p.: 102° C.;
$^1$H-NMR (200 MHz, CDCl$_3$): δ=1.67–2.29 (m, 8H), 2.77 (s, 3H), 3.75 (quint, 1H), 3.92 (s, 3H), 3.94 (s, 3H), 3.95 (s, 3H), 3.96 (s, 3H), 5.30 (s, 1H), 6.91 (d, 1H), 7.03 (s, 1H), 7.11–7.17 (m, 1H), 7.58 (d, 1H), 7.86–7.95 (m, 2H).

Example 22
2-(3,4-Dimethoxyphenyl)-5,7-dimethyl-4-(3,4,5-trimethoxyphenoxy)imidazo[5,1-f]-[1,2,4]triazine

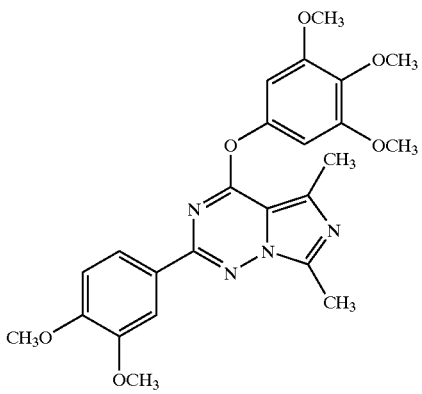

A solution of 208 mg (1.85 mmol) of potassium tert-butoxide, 682 mg (3.70 mmol) of 3,4,5-trimethoxyphenol and 650 mg (1.85 mmol) of Example 37A in 120 ml of pyridine is stirred at boiling heat for 16 h. After cooling, the solvent is removed and the residue is taken up in 200 ml of dichloromethane. The solution is washed with 2 N hydrochloric acid (3×50 ml) and saturated sodium chloride solution (50 ml), dried over sodium sulphate and the solvent is removed in vacuo. The mixture is first purified by flash chromatography (eluent gradient dichloromethane-dichloromethane/methanol 20:1), then by HPLC, and dried in a high vacuum.
Yield: 525 mg (61% of theory)
M.p.: 184° C.;
MS (DCI): 467 [M+H]$^+$;
$^1$H-NMR (200 MHz, DMSO-d$_6$): δ=2.61 (s, 3H), 2.66 (s, 3H), 3.69 (s, 3H), 3.71 (s, 3H), 3.78 (s, 9H), 6.84 (s, 2H), 7.06 (d, 1H), 7.59–7.68 (m, 2H).

Example 23
7-Cyclopentyl-2-(3,4-dimethoxyphenyl)-N-(3-methoxyphenyl)-5-methylimidazo-[5,1-f][1,2,4]triazin-4-amine

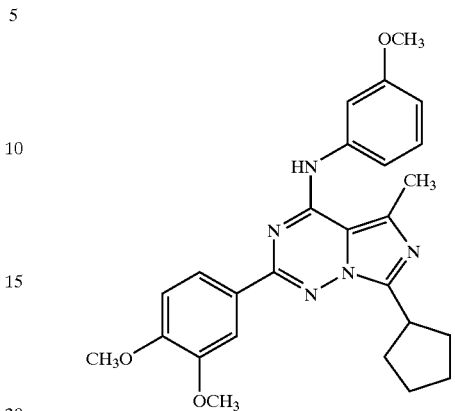

Preparation is carried out analogously to Example 10 from 150 mg (0.37 mmol) of Example 41A and 68 mg (0.55 mmol) of 3-methoxyaniline.
Yield: 140 mg (82% of theory)
M.p.: 126° C.;
MS (ESI): 460 [M+H]$^+$;
$^1$H-NMR (200 MHz, CDCl$_3$): δ=1.67–2.31 (m, 8H), 2.78 (s, 3H), 3.75 (quint, 1H), 3.86 (s, 3H), 3.95 (s, 3H), 4.00 (s, 3H), 6.69–6.78 (m, 1H), 6.95 (d, 1H), 7.04–7.39 (m, 3H), 7.69–7.77 (m, 1H), 7.88–8.01 (m, 2H).

Example 24
7-Cyclopentyl-2-[4-methoxy-3-(4-morpholinylsulphonyl)phenyl]-5-methyl-N-(3,4,5-trimethoxyphenyl)imidazo[5,1-f][1,2,4]triazin-4-amine

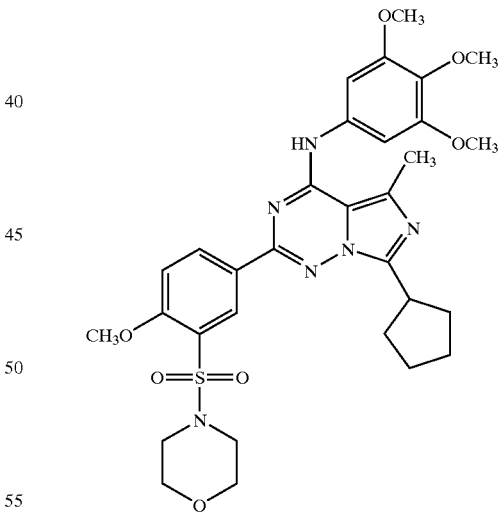

Synthesis is carried out analogously to Example 14 from 68 mg (0.13 mmol) of Example 42A and 119 mg (0.65mmol) of 3,4,5-trimethoxyaniline. Purification is carried out by flash chromatography (eluent dichloromethane/methanol 80:1).
Yield: 66 mg (80% of theory)
M.p.: 203° C.;
$^1$H-NMR (200 MHz, CDCl$_3$): δ=1.67–2.29 (m, 8H), 2.80 (s, 3H), 3.21–3.33 (m, 4H), 3.67–3.77 (m, 5H), 3.88 (s, 3H), 3.94 (s, 3H), 4.00 (s, 3H), 7.04–7.09 (m, 4H), 8.44–8.53 (m, 1H), 8.78 (d, 1H).

Example 25
7-Cyclopentyl-5-ethyl-2-[4-methoxy-3-(4-morpholinylsulphonyl)phenyl]-4-(3,4,5-trimethoxyphenoxy)imidazo[5,1-f][1,2,4]triazine

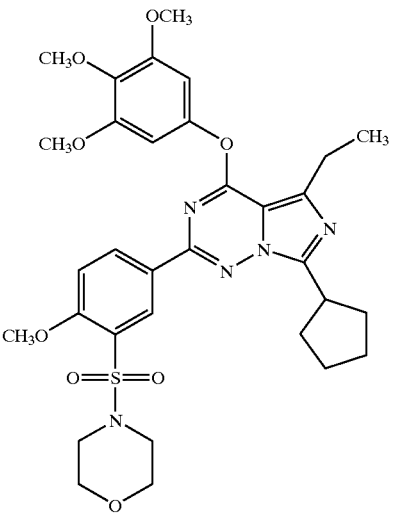

18 mg (0.16 mmol) of potassium tert-butoxide and 58 mg (0.32 mmol) of 3,4,5-trimethoxyphenol are dissolved in 2 ml of THF and the mixture is stirred for 15 min. A solution of 85 mg (0.16 mmol) of Example 43A is then added and the batch heated to reflux with stirring for 20 h. The dark brown reaction mixture is stirred into 20 ml of ice water after cooling. It is extracted with ethyl acetate (20 ml), the org. phase is dried (sodium sulphate), and the solvent is removed in vacuo. The residue is purified by flash chromatography (eluent dichloromethane/methanol 25:1). The material obtained is suspended in diethyl ether, filtered off with suction, and dried in a high vacuum.

Yield: 45 mg (43% of theory) of colourless solid.
M.p.: 119° C.;
MS (ESI): 654 [M+H]$^+$;
$^1$H-NMR (200 MHz, DMSO-d$_6$): δ=1.09 (t, 3H), 1.63–2.26 (m, 8H), 2.93–3.09 (m, 4H), 3.38 (q, 2H), 3.51–3.64 (m, 4H), 3.64–3.70 (m, 1H), 3.66 (s, 3H), 3.78 (s, 6H), 3.94 (s, 3H), 6.82 (s, 2H), 7.41 (d, 1H), 8.23–8.29 (m, 2H), 8.41 (d, 1H).

Example 26
N-[7Cyclopentyl-5-ethyl-2-(4-methoxyphenyl)imidazo[5,1-f][1,2,4]triazin-4-yl]-N-(3,4,5-trimethoxyphenyl)amine

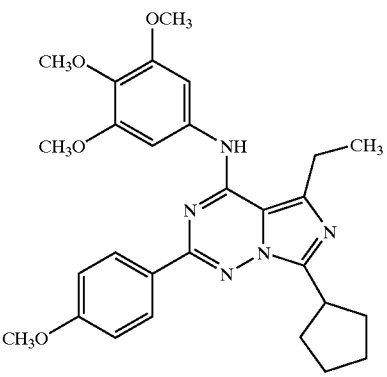

Preparation analogously to Example 14 from Example 44A (81 mg, 0.21 mmol) and 3,4,5-trimethoxyaniline (388 mg, 2.12 mmol). Purification is carried out by flash chromatography (eluent gradient 30–50% ethyl acetate in cyclohexane). Yield: 60 mg (57% of theory)
M.p.: 160° C.;
MS (ESI): 504 [M+H]$^+$
$^1$H-NMR (300 MHz, DMSO-d$_6$), δ=1.28 (t, 3H), 1.61–2.16 (m, 8H), 3.11 (q, 2H), 3.67 (quint, 1H), 3.69 (s, 3H), 3.81 (s, 3H), 3.82 (s, 6H), 7.05 (d, 2H), 7.26 (s, 2H), 8.17 (s, 2H), 8.64 (s, 1H).

Example 27
2-(3,5-Dimethoxyphenyl)-5,7-dimethyl-4-(3,4,5-trimethoxyphenoxy)imidazo[5,1-f]-[1,2,4]triazine

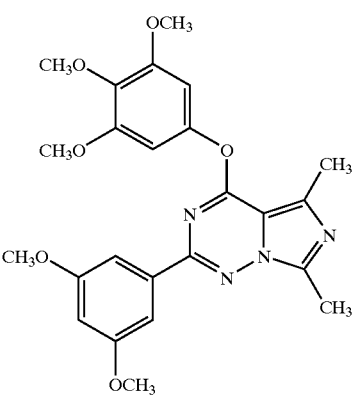

Preparation analogously to Example 22 from Example 48A (50 mg, 0.14 mmol) and 3,4,5-trimethoxyphenol (52 mg, 0.28 mmol).
Yield: 15 mg (22% of theory)
M.p.: 220° C.;
MS (ESI): 467 [M+H]$^+$
$^1$H-NMR (300 MHz, DMSO-d$_6$): δ=2.62 (s, 3H), 2.67 (s, 3H), 3.68 (s, 3H), 3.73 (s, 6H), 3.78 (s, 3H), 6.64 (t, 1H), 6.85 (s, 2H), 7.27 (d, 2H).

Example 28
2-(4-Bromophenyl)-5,7-dimethyl-4-(3,4,5-trimethoxyphenoxy)imidazo[5,1-f]-[1,2,4]triazine

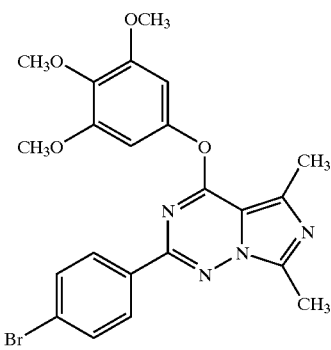

Preparation analogously to Example 22 from Example 50A (50 mg, 0.14 mmol) and 3,4,5-trimethoxyphenol (50 mg, 0.29 mmol).
Yield: 12 mg (17% of theory)
M.p.: 199° C.;
MS (ESI): 485 [M+H]$^+$
$^1$H-NMR (300 MHz, DMSO-d$_6$), δ=2.62 (s, 3H), 2.67 (s, 3H), 3.71 (s, 3H), 3.78 (s, 6H), 6.85 (s, 2H), 7.72 (d, 2H), 8.08 (d, 2H).

Example 29

2-(3–Chloro-4-methoxyphenyl)-5,7-dimethyl-4-(3,4,5-trimethoxyphenoxy)imidazo-[5,1-f][1,2,4]triazine

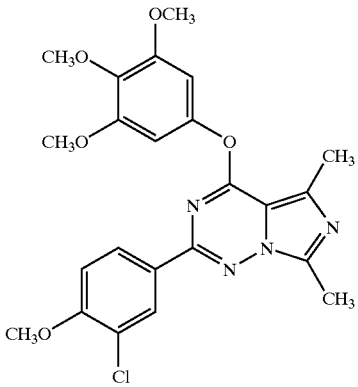

Preparation analogously to Example 22 from Example 40A (36 mg, 0.10 mmol) and 3,4,5-trimethoxyphenol (37 mg, 0.20 mmol).

Yield: 20 mg (42% of theory)

M.p.: 213° C.;

MS (ESI): 471 [M+H]$^+$ $^1$H-NMR (300 MHz, DMSO-d$_6$): δ=2.62 (s, 3H), 2.66 (s, 3H), 3.71 (s, 3H), 3.79 (s, 6H), 3.90 (s, 3H), 6.87 (s, 2H), 7.29 (d, 1H), 7.96–8.00 (m, 1H), 8.06 (d, 1H).

Example 30

2-(3–Chloro-4-methoxyphenyl)-7-isobutyl-5-methyl-4-(3,4,5-trimethoxyphenoxy)-imidazo[5,1-f][1,2,4]triazine

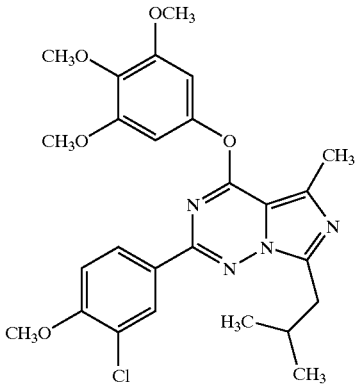

Preparation analogously to Example 22 from Example 45A (52 mg, 0.13 mmol) and 3,4,5-trimethoxyphenol (48 mg, 0.26 mmol).

Yield: 24 mg (36% of theory)

M.p.: 160° C.;

MS (ESI): 513 [M+H]$^+$ $^1$H-NMR (200 MHz, DMSO-d$_6$): δ=0.97 (d, 6H), 2.17–2.35 (m, 1H), 2.63 (s, 3H), 2.97 (d, 2H), 3.71 (s, 3H), 3.79 (s, 6H), 3.90 (s, 3H), 6.87 (s, 2H), 7.33 (d, 1H), 7.90–8.06 (m, 2H).

Example 31

7-sec-Butyl-2-(3-chloro-4-methoxyphenyl)-5-methyl-4-(3,4,5-trimethoxyphenoxy)-imidazo[5,1-f][1,2,4]triazine

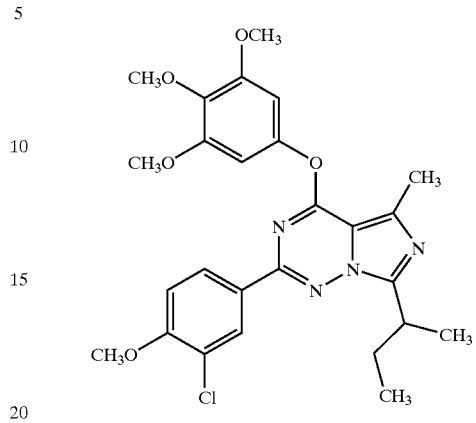

Preparation analogously to Example 22 from Example 46A (105 mg, 0.26 mmol) and 3,4,5-trimethoxyphenol (97 mg, 0.26 mmol).

Yield: 15 mg (11% of theory)

M.p.: 156° C.;

$^1$H-NMR (200 MHz, DMSO-d$_6$): δ=0.83 (t, 3H), 1.36 (d, 3H), 1.67–2.01 (m, 2H), 2.63 (s, 3H), 3.40–3.56 (m, 1H), 3.71 (s, 3H), 3.79 (s, 6H), 3.90 (s, 3H), 6.87 (s, 2H), 7.33 (d, 1H), 7.92–8.05 (m, 2H).

Example 32

2-(3Chloro-4-methoxyphenyl)-7-(1-ethylpropyl)-5-methyl-4-(3,4,5-trimethoxyphenoxy)imidazo[5,1-f][1,2,4]triazine

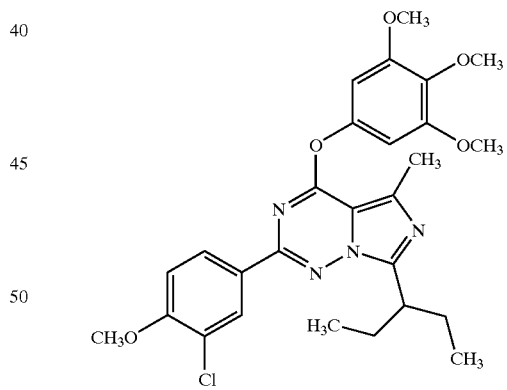

Preparation analogously to Example 22 from Example 47A (136 mg, 0.33 mmol) and 3,4,5-trimethoxyphenol (122 mg, 0.66 mmol).

Yield: 43 mg (24% of theory)

M.p.: 166° C.;

MS (ESI): 527 [M+H]$^+$ $^1$H-NMR (200 MHz, DMSO-d$_6$): δ=0.77 (t, 6H), 1.71–1.94 (m, 4H), 2.65 (s, 3H), 3.27–3.47 (m, 1H), 3.71 (s, 3H), 3.79 (s, 6H), 3.90 (s, 3H), 6.88 (s, 2H), 7.33 (d, 1H), 7.92–8.05 (m, 2H).

Example 33

2-(3-Chloro-4-methoxyphenyl)-N-(3,4-dimethoxyphenyl)-5,7-dimethylimidazo-[5,1-f][1,2,4]triazin-4-amine

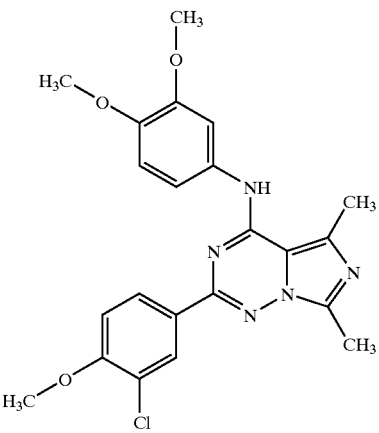

A solution of 40 mg (0.11 mmol) of Example 33A and 100 mg (0.65 mmol) of 3,4-dimethoxyaniline in 2 ml of dioxane is stirred at 100° C. for 20 hours. It is concentrated, dissolved in ethyl acetate, washed twice with water, dried and concentrated. It is purified on a silica gel column using dichloromethane/ethyl acetate [lacuna] to 2:1. Crystals are obtained, which are filtered off with suction using a mixture of diethyl ether/heptane.

Yield: 29.5 mg (59.65% of theory).
M.p.: 220–222° C.;
MS (ESI): 440 [M+H]$^+$;
$^1$H-NMR (200 MHz, DMSO-d$_6$): δ=2.57 (s, 3H), 2.68 (s, 3H), 3.81 (d, 6H), 3.91 (s, 3H), 7.02 (d, 1H), 7.18–7.29 (m, 2H), 7.57 (d, 1H), 8.08–8.20 (m, 2H), 8.83 (s, 1H).

Example 34

2-(3-Chloro-4-methoxyphenyl)-N-(3,4,5-trimethoxyphenyl)-5,7-dimethylimidazo-[5,1-f][1,2,4]triazin-4-amine

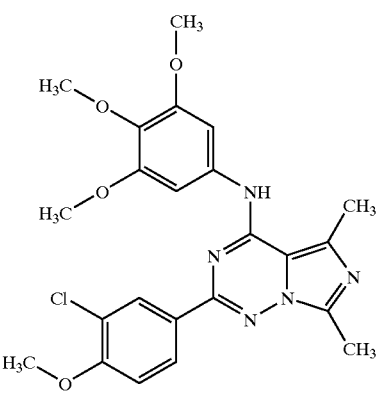

A mixture of 30 mg (0.08 mmol) of the compound of Example 33A with 100 mg (0.55 mmol) of 3,4,5-trimethoxyaniline is stirred in the form of a melt for 16 hours at a bath temperature of 120° C. It is taken up in ethyl acetate, washed with water, dried and concentrated. After purification on a silica gel column using dichloromethane/ethyl acetate [lacuna] to 2:1 and filtering off with suction using ether/heptane, 28.6 mg (43.31% of theory) of almost colourless crystals are obtained.

M.p.: 194–195° C.;
MS (ESI): 470 [M+H]$^+$;
$^1$H-NMR (300 MHz, DMSO-d$_6$): δ=2.59 (s, 3H), 2.68 (s, 3H), 3.71 (s, 3H), 3.86 (s, 6H), 3.92 (s, 3H), 7.26 (d, 3H), 8.12–8.22 (m, 2H), 8.72 (s, 1H).

Example 35

2-(4-Bromophenyl)-N-[2-(4-ethoxy-3-methoxyphenyl)ethyl]-5,7-dimethylimidazo-[5,1-f][1,2,4]triazin-4-amine

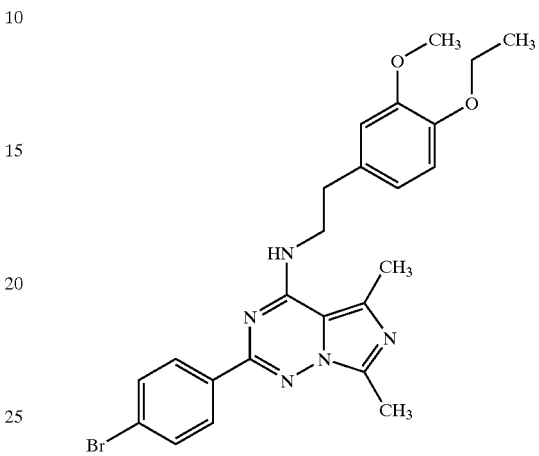

A solution of 50 mg (0.14 mmol) of Example 50A and 50 mg (0.26 mmol) of 4-ethoxy-3-methoxyphenethylamine in 3 ml of dioxane is stirred overnight at room temperature. It is concentrated, dissolved in ethyl acetate, washed with water, dried and concentrated. The crystalline evaporation residue is filtered off with suction using diethyl ether/heptane. 45.9 mg of colourless crystals are obtained.

M.p.: 188–190° C.;
MS (ESI): 496 [M+H]$^+$;
$^1$H-NMR (200 MHz, DMSO-d$_6$): δ=1.31 (t, 3H), 2.51 (s, 6H), 2.93 (b, 2H), 3.72 (s, 3H), 3.82 (b, 2H), 3.94 (quart., 2H), 6.72–6.89 (m, 3H), 7.57–7.72 (m, 3H), 8.21 (d, 2H).

Example 36

N-(4-{[2-(2-Ethoxyphenyl)-5-methyl-7-propylimidazo[5,1-f][1,2,4]triazin-4-yl]-sulphanyl}phenyl)acetamide

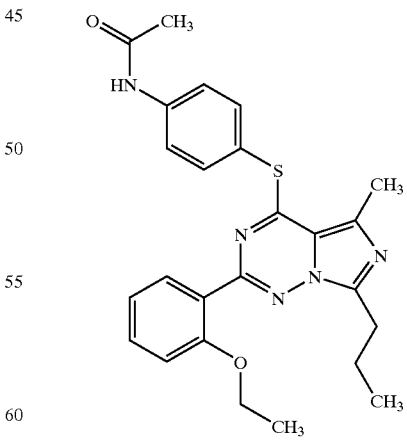

123 mg (0.66 mmol) of 4-acetamidothiophenol in 5 ml of THF are added dropwise to a suspension of 26 mg (0.66 mmol) of 40% sodium hydride in 5 ml of THF under argon. After 5 minutes, a solution of 200 mg (0.55 mmol) of Example 39A in 5 ml of THF is added dropwise to this suspension. The yellow suspension is stirred at room temperature for 60 minutes, treated with ice water and extracted twice with ethyl acetate. The organic phases are washed with water, dried and concentrated. The evaporation residue is crystallized using diethyl ether/heptane. 243.2 mg of crystals are obtained.

M.p.: 226–228° C.;
MS (ESI): 462 [M+H]$^+$;
$^1$H-NMR (300 MHz, CDCl$_3$): δ=1.00 (t, 3H), 1.36 (t, 3H), 1.82–1.96 (sex., 2H), 2.14 (s, 3H), 2.80 (s, 3H), 3.06 (t, 2H), 4.03 (quart., 2H), 6.88 (quart., 2H), 7.28 (m, 1H), 7.41 (s, 1H), 7.53 (m, 5H).

Example 37

2-(2-Ethoxyphenyl)-5-methyl-N-phenyl-7-propylimidazo[5,1-f][1,2,4]triazin-4-amine

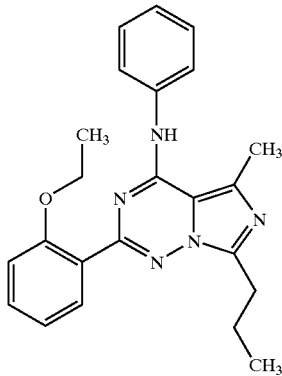

Synthesis analogously to Example 33 from the appropriate starting compounds.
MS (ESI): 388 [M+H]$^+$;
$^1$H-NMR (200 MHz, CDCl$_3$): δ=*1.03 (m, 6H), **1.41 (t, 3H), 1.78–1.97 (m, 2H), *2.68 (s, 3H), **2.79 (s, 3H), 2.92–3.09 (quart., 2H), *3.88 (quart., 2H), **4.16 (quart., 2H), 6.85–7.13 (m, 4H), 7.38 (m, 3H), 7.73 (m, 2H), 9.67 (s, 1H).
Tautomeric mixture A* and B** ratio 1:1

Example 38

N-[2-(2-Ethoxyphenyl)-5-methyl-7-propylimidazo[5,1-f][1,2,4]triazin-4-yl]-N-(2-fluorobenzyl)amine

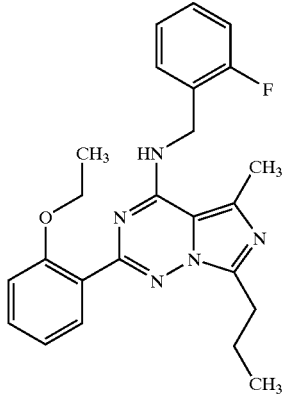

Preparation analogously to Example 35 from the appropriate starting compounds, reaction time 40 min.
MS (ESI): 420 [M+H]$^+$;
$^1$H-NMR (200 MHz, CDCl$_3$): δ=0.97 (t, 3H), 1.38 (t, 3H), 1.77–1.96 (sex., 2H), 2.52 (s, 3H), 3.02 (t, 2H), 4.06–4.18 (quart., 2H), 4.93 (d, 2H), 5.74 (t, 1H), 6.99 (m, 4H), 7.29–7.50 (m, 3H), 7.77 (dd, 1H).

Example 39

N-(3-Bromophenyl)-2-(2-ethoxyphenyl)-5-methyl-7-propylimidazo[5,1-f]-[1,2,4]triazin-4-amine

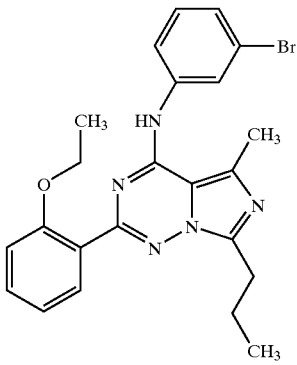

Synthesis analogously to Example 33 from the appropriate starting compounds, reaction time 2 days.
M.p.: 96° C.;
MS (DCI): 466 [M+H]$^+$;
$^1$H-NMR (300 MHz, CDCl$_3$): δ=*0.95 (m, 6H), **1.41 (t, 3H), 1.87 (m, 2H), *2.62 (s, 3H), **2.79 (s, 3H), 2.93–3.09 (m, 2H), *3.93 (quart., 2H), **4.18 (quart., 2H), 6.87–7.12 (m, 3H), 7.20 (d, 2H), 7.42 (m, 1H), 7.60–7.79 (m, 1H), 8.13–8.30 (m, 1H), 9.68 (s, 1H).
Tautomeric mixture A* and B** ratio 2.2:1

Example 40

N-Benzyl-2-(2-ethoxyphenyl)-N,5-dimethyl-7-propylimidazo[5,1-f][1,2,4]triazin-4-amine

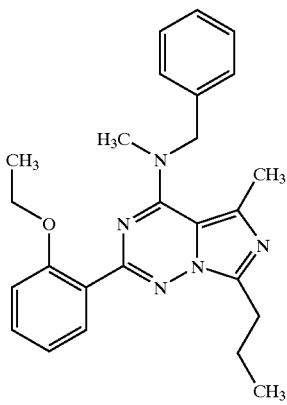

Synthesis analogously to Example 33 from the appropriate starting compounds.
MS (ESI): 416 [M+H]$^+$;
$^1$H-NMR (200 MHz, CDCl$_3$): δ=1.01 (t, 3H), 1.39 (t, 3H), 1.80–1.98 (sex., 2H), 2.58 (s, 3H), 3.06 (t, 2H), 3.19 (s, 3H), 4.07–4.18 (quart., 2H), 4.96 (s, 2H), 6.96 (m, 2H), 7.29–7.42 (m, 6H), 7.79 (dd, 1H).

Example 41

2-(2-Ethoxyphenyl)-N-[2-(2-fluorophenyl)ethyl]-5-methyl-7-propylimidazo[5,1-f]-[1,2,4]triazin-4-amine

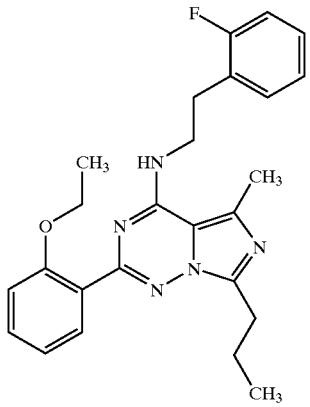

Preparation analogously to Example 35 from the appropriate starting compounds.

MS (ESI): 434 [M+H]+;

1H-NMR (200 MHz, CDCl3): δ=0.98 (t, 3H), 1.39 (t, 3H), 1.78–1.96 (sex., 2H), 2.51 (s, 3H), 2.96–3.13 (m, 4H), 3.89–3.98 (quart., 2H), 4.07–4.17 (quart., 2H), 5.42 (t, 1H), 6.98–7.12 (m, 4H), 7.21 (d, 2H), 7.48 (m, 1H), 7.78 (dd, 1H).

Example 42

N-[2-(2-Ethoxyphenyl)-5-methyl-7-propylimidazo[5,1-f][1,2,4]triazin-4-yl]-N-(3-fluorophenyl)amine

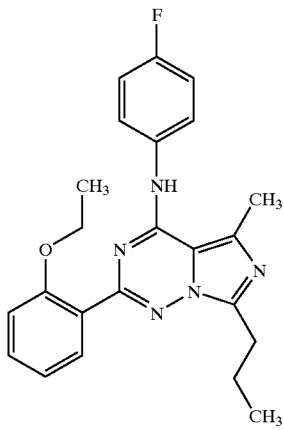

Synthesis analogously to Example 33 from the appropriate starting compounds.

MS (ESI): 406 [M+H]+;

1H-NMR (200 MHz, CDCl3): δ=*1.05 (m, 6H), **1.42 (t, 3H), 1.78–1.96 (m, 2H), *2.65 (s, 3H), **2.78 (s, 3H), 2.94–3.09 (m, 2H), *3.93 (quart., 2H), **4.18 (quart., 2H), 6.71–6.96 (m, 3H), 7.00–7.18 (m, 2H), 7.31–7.78 (m, 2H), 8.07–8.17 (m, 1H), 9.67 (s, 1H).

Tautomeric mixture A* and B** ratio 1.5:1

Example 43

3-{[2-(2-Ethoxyphenyl)-5-methyl-7-propylimidazo[5,1-f][1,2,4]triazin-4-yl]-amino}phenol

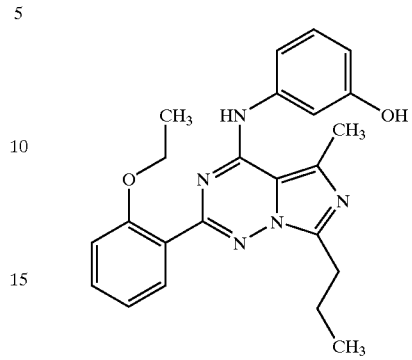

Synthesis analogously to Example 33 from the appropriate starting compounds.

MS (ESI): 404 [M+H]+;

1H-NMR (200 MHz, DMSO-d6): δ=0.93 (t, 3H), 1.28 (t, 3H), 1.68–1.86 (sex., 2H), 2.68 (s, 3H), 2.90 (t, 2H), 4.03–4.13 (quart., 2H), 6.56 (d, 1H), 7.00 (t, 1H), 7.12 (m, 2H), 7.26 (m, 2H), 7.42 (m, 1H), 7.58 (dd, 1H), 8.65 (s, 1H), 9.41 (s, 1H).

Example 44

2-(2-Ethoxyphenyl)-5-methyl-7-propyl-N-(3,4,5-trimethoxyphenyl)imidazo[5,1-f]-[1,2,4]triazin-4-amine

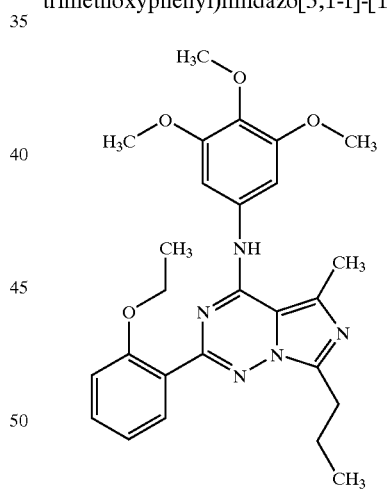

Synthesis analogously to Example 33 from the appropriate starting compounds.

M.p.: 112–114° C.;

MS (ESI): 478 [M+H]+;

1H-NMR (400 MHz, CDCl3): δ=*1.03 (m, 6H), **1.48 (t, 3H), 1.88 (m, 2H), *2.67 (s, 3H), **2.80 (s, 3H), *2.95 (t, 2H), **3.07 (t, 2H), 3.83 (d, 9H), *3.94 (quart., 2H), **4.11 (quart., 2H), 6.28 (s, 1H), 6.90–7.18 (m, 3H), 7.43 (m, 1H), *7.86 (m, 1H), **8.20 (m, 1H), 9.88 (s, 1H).

Tautomeric mixture A* and B** ratio 2:1

Example 45

2-(2-Ethoxyphenyl)-5-methyl-N-[(5-methyl-2-furyl)methyl]-7-propylimidazo[5,1-f]-[1,2,4]triazin-4-amine

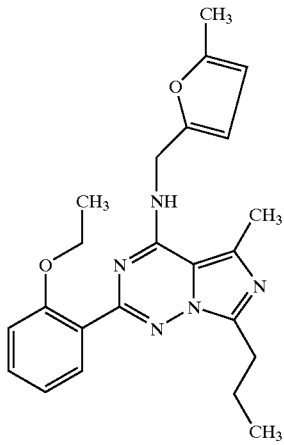

Preparation analogously to Example 35 from the appropriate starting compounds.

MS (ESI): 406 [M+H]+;

$^1$H-NMR (300 MHz, CDCl$_3$): δ=0.99 (t, 3H), 1.39 (t, 3H), 1.81–1.93 (sex., 2H), 2.29 (s, 3H), 2.63 (s, 3H), 3.01 (t, 2H), 4.12 (quart., 2H), 4.80 (d, 2H), 5.58 (t, 1H), 5.93 (d, 1H), 6.20 (d, 1H), 7.02 (m, 2H), 7.38 (m, 1H), 7.80 (dd, 1H).

Example 46

N-(2,4-Dimethoxybenzyl)-2-(2-ethoxyphenyl)-5-methyl-7-propylimidazo[5,1-f]-[1,2,4]triazin-4-amine

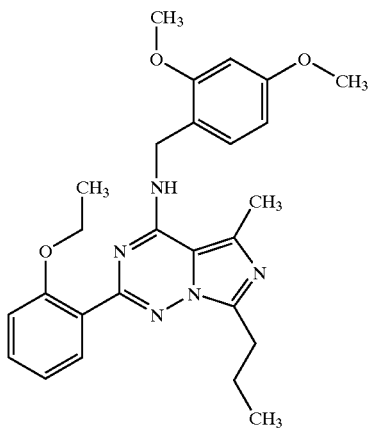

Preparation analogously to Example 35 from the appropriate starting compounds.

M.p.: 98–99° C.;

MS (ESI): 462 [M+H]+;

$^1$H-NMR (200 MHz, CDCl$_3$): δ=0.99 (t, 3H), 1.39 (t, 3H), 1.75–1.93 (sex., 2H), 2.60 (s, 3H), 2.98 (t, 2H), 3.79 (s, 3H), 3.91 (s, 3H), 4.13 (quart., 2H), 4.79 (d, 2H), 6.13 (t, 1H), 6.40–6.51 (m, 2H), 6.97–7.08 (m, 2H), 7.23–7.42 (m, 2H), 7.81 (dd, 1H).

Example 47

N-(2,3-Dimethoxybenzyl)-2-(2-ethoxyphenyl)-5-methyl-7-propylimidazo[5,1-f]-[1,2,4]triazin-4-amine

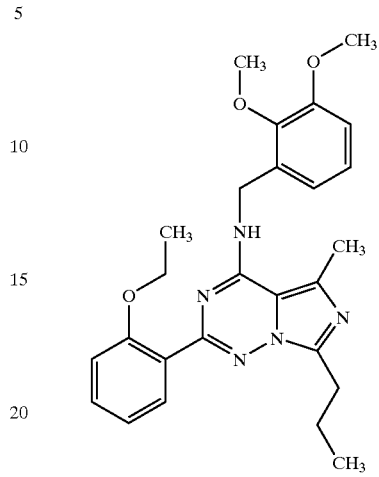

Preparation analogously to Example 35 from the appropriate starting compounds.

MS (ESI): 462 [M+H]+;

$^1$H-NMR (400 MHz, CDCl$_3$): δ=1.00 (t, 3H), 1.39 (t, 3H), 1.81–1.91 (sex., 2H), 2.52 (s, 3H), 3.00 (t, 2H), 3.87 (s, 3H), 3.93 (s, 3H), 4.12 (quart., 2H), 4.88 (d, 2H), 6.12 (t, 1H), 6.90 (dd, 1H), 6.96–7.05 (m, 4H), 7.38 (m, 1H), 7.78 (dd, 1H).

Example 48

N-[2-(4-Bromophenyl)-5,7-dimethylimidazo[5,1-f][1,2,4]triazin-4-yl]-N-(3,4,5-trimethoxyphenyl)amine

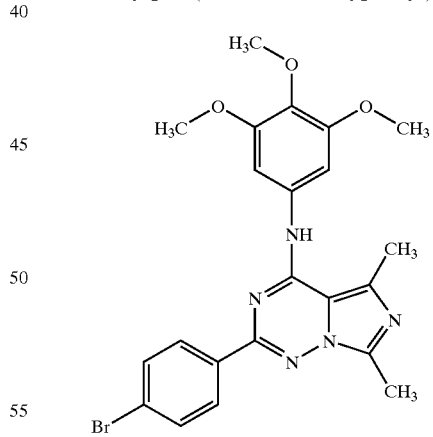

Synthesis analogously to Example 33 from the appropriate starting compounds, reaction time 3 days at 100° C.

M.p.: 219–220° C.;

MS (ESI): 484 [M+H]+;

$^1$H-NMR (200 MHz, DMSO-d$_6$): δ=2.60 (s, 3H), 2.70 (s, 3H), 3.20 (s, 3H), 3.82 (s, 6H), 7.25 (s, 2H), 7.72 (d, 2H), 8.17 (d, 2H), 8.81 (s, 1H).

Example 49

N-[2-(2-Ethoxyphenyl)-5-methyl-7-propylimidazo[5,1-f][1,2,4]triazin-4-yl]-N-(3-methoxyphenyl)amine

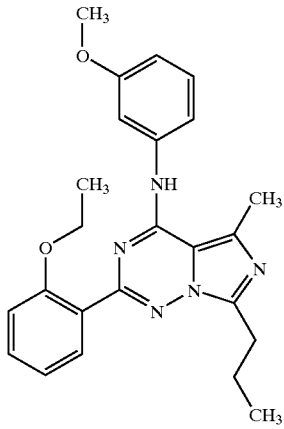

Synthesis analogously to Example 33 from the appropriate starting compounds.

MS (ESI): 418 [M+H]+;

1H-NMR (400 MHz, CDCl3): δ=*1.02 (m, 6H), **1.41 (t, 3H), 1.87 (m, 2H), *2.68 (s, 3H), **2.79 (s, 3H), *2.95 (t, 2H), **3.07 (t, 2H), 3.80 (s, 3H), *3.93 (quart., 2H), **4.14 (quart., 2H), 6.58–6.71 (m, 2H), 6.88–7.12 (m, 3H), 7.20–7.42 (m, 2H), 7.78–8.18 (m, 1H), 9.71 (s, 1H).

Tautomeric mixture A* and B** ratio 1.5:1

Example 50

N-[2-(4-Bromophenyl)-5,7-dimethylimidazo[5,1-f][1,2,4]triazin-4-yl]-N-(3,4,5-trimethoxybenzyl)amine

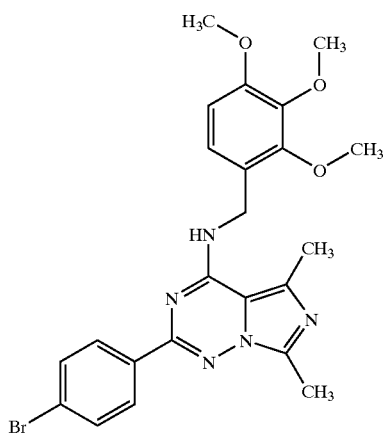

Synthesis analogously to Example 33 from the appropriate starting compounds.

M.p.: 182–184° C.;

MS (ESI): 498 [M+H]+;

1H-NMR (400 MHz, CDCl3): δ=2.53 (s, 3H), 2.68 (s, 3H), 3.84 (d, 9H), 4.88 (d, 2H), 5.70 (t, 1H), 6.68 (s, 2H), 7.58 (d, 2H), 8.25 (d, 2H).

Example 51

2-(4-Bromophenyl)-N-(3,4-dimethoxybenzyl)-5,7-dimethylimidazo[5,1-f]-[1,2,4]triazin-4-amine

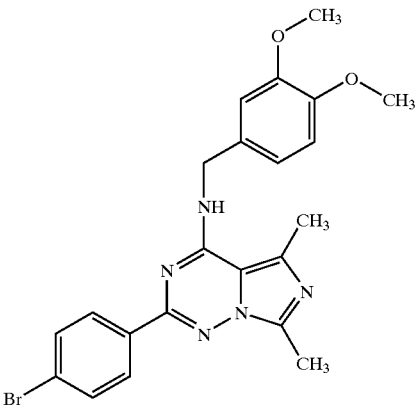

Preparation analogously to Example 35 from the appropriate starting compounds.

M.p.: 119–122° C.;

MS (ESI): 468 [M+H]+;

1H-NMR (200 MHz, DMSO-d6): δ=2.58 (s, 3H), 2.60 (s, 3H), 3.68 (s, 6H), 4.77 (d, 2H), 6.88–7.01 (m, 2H), 7.16 (d, 1H), 7.68 (d, 2H), 8.10–8.23 (m, 3H).

Example 52

N-(1,3-Benzodioxol-5-ylmethyl)-2-(4-bromophenyl)-5,7-dimethylimidazo[5,1-f]-[1,2,4]triazin-4-amine

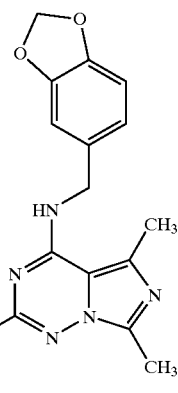

Preparation analogously to Example 35 from the appropriate starting compounds.

M.p.: 188–190° C.;

MS (ESI): 457 [M+H]+;

1H-NMR (200 MHz DMSO-d6): δ=2.53 (s, 3H), 2.59 (s, 3H), 4.76 (d, 2H), 5.95 (s, 2H), 6.83–6.96 (m, 2H), 7.03 (d, 1H), 7.68 (d, 2H) 8.08–8.21 (m, 3H).

Example 53

N-[5,7-Dimethyl-2-(4-methylphenyl)imidazo[5,1-f][1,2,4]triazin-4-yl]-N-(3,4,5-trimethoxyphenyl)amine

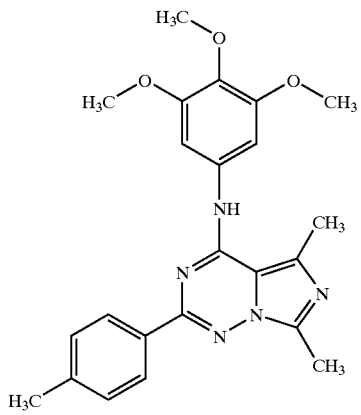

Preparation analogously to Example 34 from the appropriate starting substances.

M.p.: 212–214° C.;

MS (ESI): 420 [M+H]$^+$;

$^1$H-NMR (300 MHz, DMSO-d$_6$): δ=2.38 (s, 3H), 2.59 (s, 3H), 2.69 (s, 3H) 3.68 (s, 3H), 3.85 (s, 6H), 7.28 (d, 4H), 8.13 (d, 2H), 8.69 (s, 1H).

Example 54

2-(3,5-Dimethoxyphenyl)-5,7-dimethyl-N-(3,4,5-trimethoxyphenyl)imidazo[5,1-f]-[1,2,4]triazin-4-amine

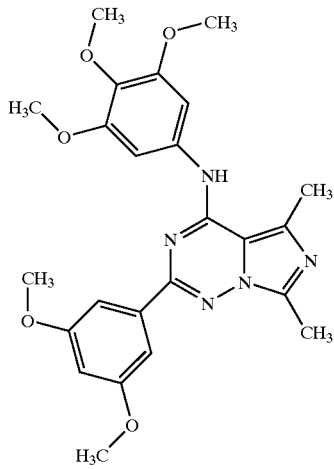

Preparation analogously to Example 34 from the appropriate starting substances, reaction time 24 h.

M.p.: 176–179° C.;

MS (ESI): 466 [M+H]$^+$;

$^1$H-NMR (300 MHz, DMSO-d$_6$): δ=2.61 (s, 3H), 2.68 (s, 3H), 3.68 (s, 3H) 3.78 (s, 6H), 3.82 (s, 6H), 6.65 (t, 1H), 7.22 (s, 2H), 7.39 (d, 2H), 8.79 (s, 1H).

Example 54A

4-Nitrobenzenecarboximidamide hydrochloride

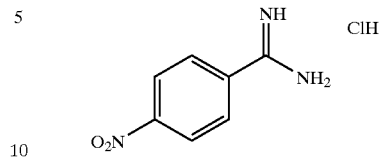

Preparation is carried out as described for Example 1A by reaction of 15.0 g (101 mmol) of 4-nitrobenzonitrile with 16.3 g (304 mmol) of ammonium chloride and 304 mmol of trimethylaluminium (150 ml of 2 M solution in hexane) in toluene.

Yield: 17.6 g (86% of theory)

10 MS (DCI, ammonia): m/z=166.1 [M−Cl$^-$]$^+$

Example 55A 2,4-Dimethoxybenzenecarboximidamide hydrochloride

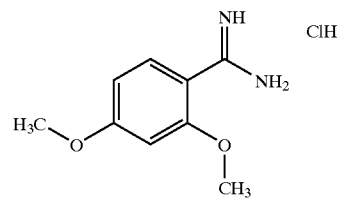

Preparation is carried out as described for Example 1A by reaction of 16.3 g (100 mmol) of 2,4-dimethoxybenzonitrile with 10.7 g (200 mmol) of ammonium-chloride and 200 mmol of trimethylaluminium (100 ml of 2 M solution in hexane) in toluene.

Yield: 6.8 g (31% of theory)

MS (DCI, ammonia): m/z=181 [M−Cl$^-$]$^+$

Example 56A 4-(Benzyloxy)benzenecarboximidamide hydrochloride

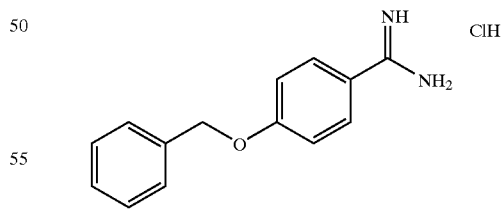

Preparation is carried out as described for Example 1A by reaction of 9.40 g (44.9 mmol) of 4-(benzyloxy)benzonitrile with 4.81 g (89.9 mmol) of ammonium chloride and 89.9 mmol of trimethylaluminium (45 ml of 2 M solution in hexane) in toluene.

Yield: 83.3 g (70% of theory)

MS (DCI, ammonia): m/z=227.2 [M−Cl$^-$]$^+$

Example 57A

N-{1-[3-(4-Nitrophenyl)-5-oxo-4,5-dihydro-1,2,4-triazin-6-yl]ethyl}acetamide

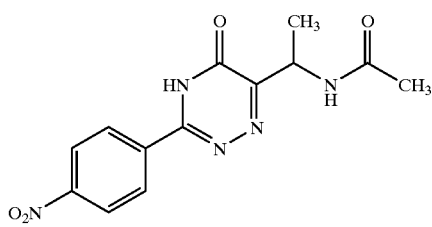

Preparation analogously to Example 11A from 24.5 g (122 mmol) of 4-nitrobenzene-carboximidamide hydrochloride.

Yield: 14.8 g (40% of theory)

$^1$H-NMR (400 MHz, CD$_3$OD): δ=1.49 (d, 3H), 1.99 (s, 3H), 5.23 (m, 1H), 8.26 (d, 1H), 8.41 (d, 1H).

Example 58A

N-{1-[3-(4-Methoxyphenyl)-5-oxo-4,5-dihydro-1,2,4-triazin-6-yl]ethyl}acetamide

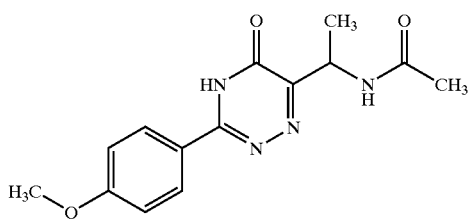

Preparation analogously to Example 11A from 12.8 g (68.8 mmol) of 4-methoxy-benzenecarboximidamide hydrochloride.

Yield: 5.03 g (24% of theory)

LC/MS (method 1): R$_t$=2.04 min

MS (ES+): m/z=289 [M+H]$^+$

Example 59A 6-(1-Aminoethyl)-3-(4-nitrophenyl)-1,2,4-triazin-5(4H)-one

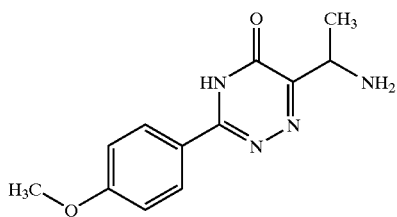

Preparation analogously to Example 12A from 1.62 g (5.63 mmol) of Example 58A. Purification by flash chromatography (eluent dichloromethane/methanol 20/1 to 5/1, with addition of aqueous ammonium hydroxide solution).

Yield: 745 mg (54% of theory)

$^1$H-NMR (400 MHz, CD$_3$OD): δ=1.62 (d, 3H), 3.86 (s, 3H), 4.60 (q, 1H), 7.03 (d, 1H), 8.11 (d, 1H).

Example 60A

N-{1-[3-(2,4-Dimethoxyphenyl)-5-oxo-4,5-dihydro-1,2,4-triazin-6-yl]ethyl}-acetamide

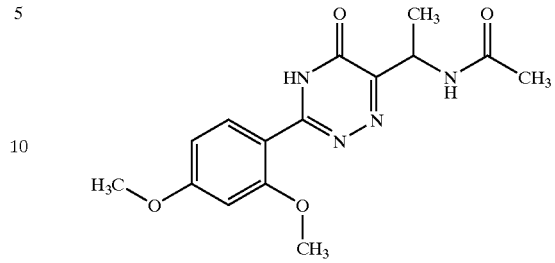

Preparation analogously to Example 11A from 1.90 g (8.77 mmol) of 2,4-dimethoxy-benzenecarboximidamide hydrochloride.

Yield: 910 mg (32% of theory)

$^1$H-NMR (400 MHz, CD$_3$OD): δ=1.46 (d, 3H), 1.97 (s, 3H), 3.89 (s, 3H), 4.00 (s, 3H), 5.18 (m, 1H), 6.70–6.75 (m, 2H), 8.10 (d, 1H).

Example 61A

N-(1-{3-[4-(Benzyloxy)phenyl]-5-oxo-4,5-dihydro-1,2,4-triazin-6-yl}ethyl)-acetamide

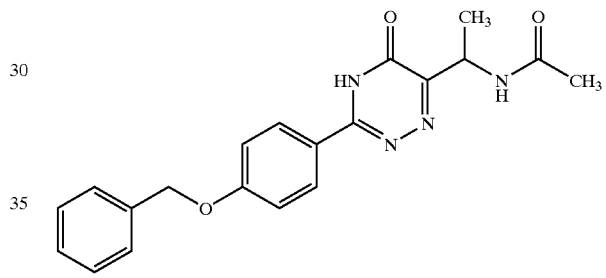

Preparation analogously to Example 11A from 8.26 g (31.4 mmol) of 4-(benzyloxy)-benzenecarboximidamide hydrochloride.

Yield: 2.26 g (20% of theory)

$^1$H-NMR (400 MHz, CD$_3$OD): δ=1.47 (d, 3H), 1.98 (s, 3H), 5.14–5.22 (m, 3H, s at 5.20), 7.18 (d, 2H), 7.32 (t, 1H), 7.38 (t, 2H), 7.45 (d, 2H), 8.00 (d, 2H).

Example 62A 6-(1-Aminoethyl)-3-(4-methylphenyl)-1,2,4-triazin-5(4H)-one

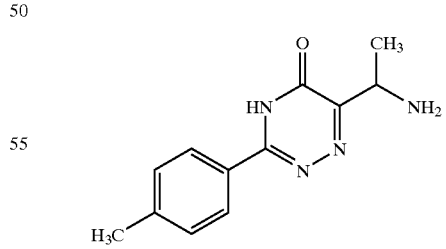

Preparation analogously to Example 12A from 20.9 g (76.8 mmol) of Example 22A. Purification by flash chromatography (eluent dichloromethane/methanol 20/1 to 5/1, with addition of aqueous ammonium hydroxide solution).

Yield: 13.5 g (75% of theory)

$^1$H-NMR (300 MHz, DMSO-d$_6$): δ=1.50 (d, 3H), 2.35 (s, 3H), 4.43 (q, 1H), 7.25 (d, 2H), 8.12 (d, 2H).

Example 63A

7-Isopropyl-5-methyl-2-(4-methylphenyl)imidazo[5,1-f][1,2,4]triazin-4(3H)-one

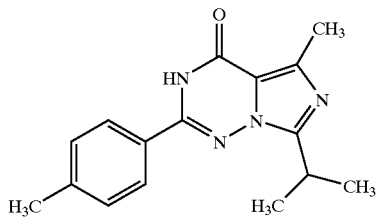

500 mg (2.17 mmol) of Example 62A are dissolved in DMF with 330 mg (3.26 mmol) of triethylamine. After the dropwise addition of 250 mg (2.39 mmol) of 2-methylpropanoyl chloride, the batch is stirred at RT for about 18 h. The addition of a further portion of acid chloride is possibly necessary to achieve complete conversion. The solvent is then completely stripped off in vacuo, and the residue is suspended in dichloroethane and treated with 766 mg (4.99 mmol) of phosphorus oxychloride. It is stirred under reflux at 90° C. for about 2 h. Following this, the batch is neutralized in an ice bath using a little saturated sodium hydrogencarbonate solution, then concentrated and flash chromatographed using the eluent dichloromethane/methanol 100/1, 50/1.

Yield: 256 mg (55% of theory)

$^1$H-NMR (300 MHz, CDCl$_3$): δ=1.44 (d, 6H), 2.45 (s, 3H), 2.66 (s, 3H), 3.61 (m, 1H), 7.34 (d, 2H), 7.79 (d, 2H), 8.74 (s, br 1H).

Example 64A 7-sec-Butyl-5-methyl-2-(4-methylphenyl)imidazo[5,1-f][1,2,4]triazin-4(3H)-one

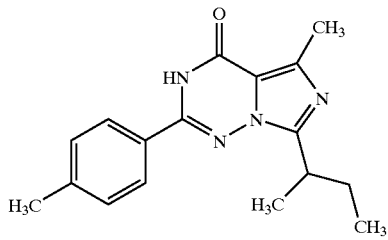

Preparation analogously to Example 63A from 500 mg (2.17 mmol) of Example 62A, 288 mg (2.39 mmol) of 2-methylbutanoyl chloride and the appropriate amounts of the remaining reagents.

Yield: 650 mg (quant.)

$^1$H-NMR (400 MHz, CD$_3$OD): δ=0.88 (t, 3H), 1.38 (d, 3H), 1.71–1.97 (m, 2H), 2.43 (s, 3H), 2.58 (s, 3H), 3.46 (m, 1H), 7.36 (d, 2H), 7.83 (d, 2H).

Example 65A 7-(1-Ethylpropyl)-5-methyl-2-(4-methylphenyl)imidazo[5,1-f][1,2,4]triazin-4(3H)-one

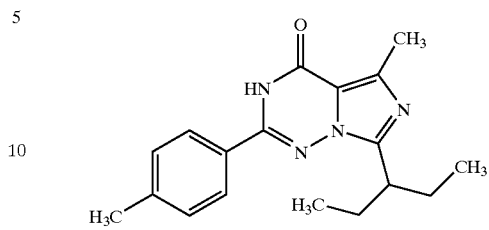

Preparation analogously to Example 63A from 500 mg (2.17 mmol) of Example 62A, 322 mg (2.39 mmol) of 2-ethylbutanoyl chloride and the appropriate amounts of the remaining reagents.

Yield: 230 mg (49% of theory)

$^1$H-NMR (400 MHz, CD$_3$OD): δ=0.91 (t, 6H), 1.88–2.00 (m, 4H), 2.45 (s, 3H), 2.73 (s, 3H), 3.50 (m, 1H), 7.41 (d, 2H), 7.86 (d, 2H).

Example 66A 5,7-Dimethyl-2-(4-nitrophenyl)imidazo[5,1-f][1,2,4]triazin-4(3H)-one

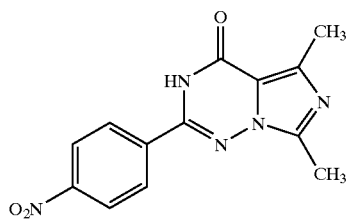

Analogously to Example 33A, 3.60 g (11.9 mmol) of Example 57A and 5.46 g (35.6 mmol) of phosphorus oxychloride are reacted.

Yield: 3.4 g (quant.)

$^1$H-NMR (400 MHz, CD$_3$OD): δ=2.59 (s, 3H), 2.64 (s, 3H), 8.19 (d, 2H), 8.40 (d, 1H).

Example 67A 2-(4-Methoxyphenyl)-5,7-dimethylimidazo[5,1-f][1,2,4]triazin-4(3H)-one

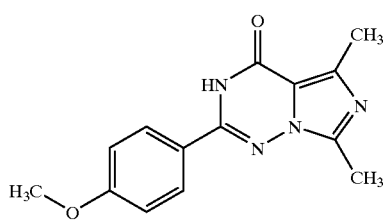

Analogously to Example 33A, 5.03 g (17.5 mmol) of Example 58A and 8.03 g (52.4 mmol) of phosphorus oxychloride are reacted.

Yield: 4.39 g (93% of theory)

$^1$H-NMR (400 MHz, CD$_3$OD+DMSO-d$_6$): δ=2.55 (s, 3H), 2.60 (s, masked, 3H), 3.88 (s, 3H), 7.09 (d, 2H), 7.95 (d, 2H).

Example 68A
7-Isopropyl-2-(4-methoxyphenyl)-5-methylimidazo[5,1-f][1,2,4]triazin-4(3H)-one

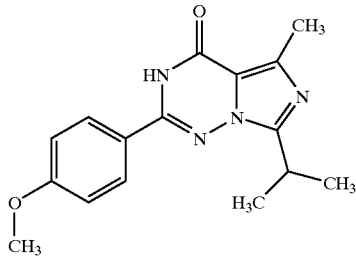

Preparation analogously to Example 63A from 300 mg (1.22 mmol) of Example 59A, 195 mg (1.83 mmol) of 2-methylpropanoyl chloride and the appropriate amounts of the remaining reagents.
Yield: 85 mg (23% of theory)
$^1$H-NMR (300 MHz, CD$_3$OD): δ=1.52 (d, 6H), 2.74 (s, 3H), 3.86 (m, 1H), 3.90 (s, 3H), 7.11 (d, 2H), 7.14 (d, 2H).

Example 69A
2-(2,4-Dimethoxyphenyl)-5,7-dimethylimidazo[5,1-f][1,2,4]triazin-4(3H)-one

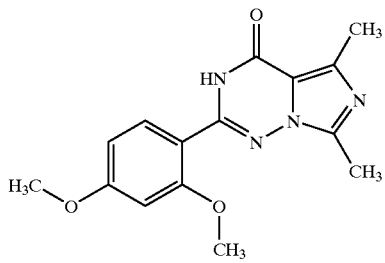

Analogously to Example 33A, 1.20 g (3.77 mmol) of Example 60A and 1.73 g (11.3 mmol) of phosphorus oxychloride are reacted.
Yield: 412 mg (37% of theory)
$^1$H-NMR (300 MHz, CD$_3$OD): δ=2.67 (s, 3H), 2.73 (s, 3H), 3.89 (s, 3H), 3.95 (s, 3H), 6.67–6.74 (m, 2H), 7.76 (d, 1H).

Example 70A
2-[4-(Benzyloxy)phenyl]-5,7-dimethylimidazo[5,1-f][1,2,4]triazin-4(3H)-one

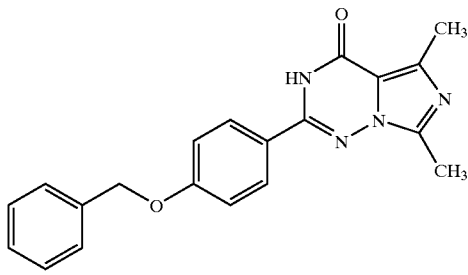

Analogously to Example 33A, 2.19 g (6.02 mmol) of Example 61A and 1.85 g (12.0 mmol) of phosphorus oxychloride are reacted.
Yield: 2.1 g (quant.)
$^1$H-NMR (400 MHz, CD$_3$OD): δ=2.66 (s, 3H), 2.74 (s, 3H), 5.20 (s, 2H), 7.17 (d, 2H), 7.32 (t, 1H), 7.38 (t, 2H), 7.46 (d, 2H), 7.94 (d, 2H).

Example 71A
7-Isopropyl-5-methyl-2-(4-methylphenyl)-4-(1H-1,2,4-triazol-1-yl)imidazo-[5,1-f]-[1,2,4]triazine

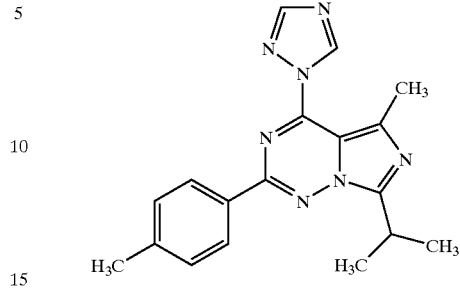

Preparation analogously to Example 37A starting from 247 mg (0.875 mmol) of Example 63A.
Yield: 168 mg (58%)
$^1$H-NMR (300 MHz, CDCl$_3$): δ=1.51 (d, 6H), 2.45 (s, 3H), 2.88 (s, 3H), 3.80 (m, 1H), 7.33 (d, 2H), 8.23–8.27 (m, 3H), 9.36 (s, 1H).

Example 72A
7-sec-Butyl-5-methyl-2-(4-methylphenyl)-4-(1H-1,2,4-triazol-1-yl)imidazo[5,1-f]-[1,2,4]triazine

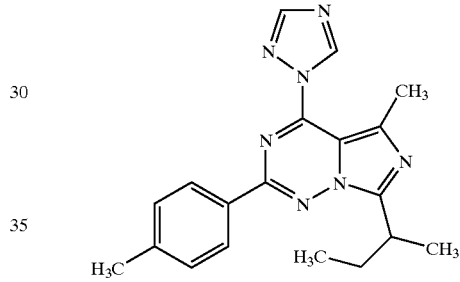

Preparation analogously to Example 37A starting from 865 mg (2.92 mmol) of Example 64A.
Yield: 216 mg (21%)
$^1$H-NMR (300 MHz, CDCl$_3$): δ=0.93 (t, 3H), 1.48 (d, 3H), 1.78–2.12 (m, 2H), 2.45 (s, 3H), 2.88 (s, 3H), 3.58–3.71 (m, 1H), 7.32 (d, 2H), 8.21–8.27 (m, 3H), 9,36 (s, 1H).

Example 73A
7-(1-Ethylpropyl)-5-methyl-2-(4-methylphenyl)-4-(1H-1,2,4-triazol-1-yl)imidazo-[5,1-f][1,2,4]triazine

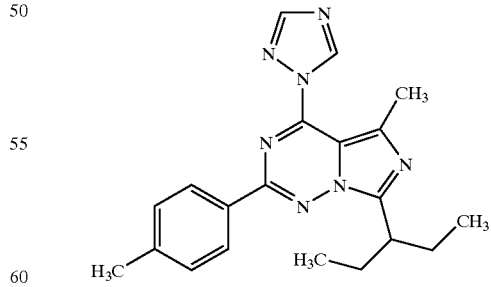

Preparation analogously to Example 37A starting from 634 mg (2.04 mmol) of Example 65A.
Yield: 413 mg (56%)
$^1$H-NMR (300 MHz, CD$_3$OD): δ=0.86 (t, 6H), 1.85–2.07 (m, 4H), 2.43 (s, 3H), 2.84 (s, 3H), 3.50–3.62 (m, 1H), 7.34 (d, 2H), 8.28 (d, 2H), 9.39 (s, 1H), 9.64 (s, 1H).

Example 74A 5,7-Dimethyl-2-(4-nitrophenyl)-4-(1H-1,2,4-triazol-1-yl)imidazo[5,1-f][1,2,4]triazine

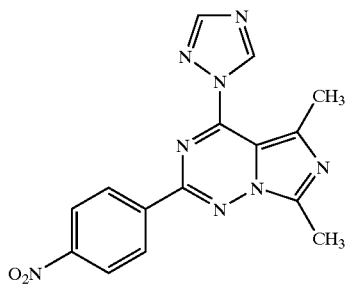

Preparation analogously to Example 37A starting from 1.57 g (5.50 mmol) of Example 66A.

Yield: 1.06 g (54%)

$^1$H-NMR (300 MHz, CD$_3$OD): δ=2.85 (s, 3H), 2.91 (s, 3H), 8.41–8.46 (m, 3H), 8.70–8.75 (d, 2H), 9.79 (s, 1H).

Example 75A 2-(4-Methoxyphenyl)-5,7-dimethyl-4-(1H-1,2,4-triazol-1-yl)imidazo [5,1-f][1,2,4]-triazine

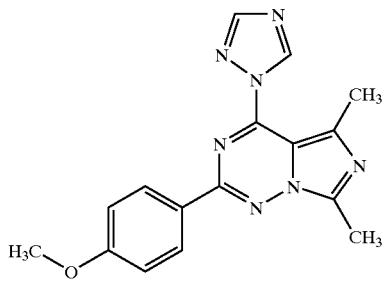

Preparation analogously to Example 37A starting from 1.5 g (5.55 mmol) of Example 67A.

Yield: 520 mg (29%)

$^1$H-NMR (400 MHz, CDCl$_3$): δ=2.81 (s, 3H), 2.87 (s, 3H), 3.91 (s, 3H), 7.03 (d, 2H), 8.26 (s, 1H), 8.33 (d, 2H), 9.37 (s, 1H).

Example 76A

7-Isopropyl-2-(4-methoxyphenyl)-5-methyl-4-(1H-1,2,4-triazol-1-yl)imidazo[5,1-f]-[1,2,4]triazine

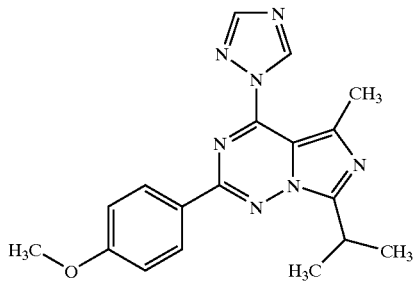

Preparation analogously to Example 37A starting from 70 mg (0.23 mmol) of Example 68A.

Yield: 80 mg (quant.)

MS (ESI): m/z=350 [M+H]$^+$

Example 77A 2-(2,4-Dimethoxyphenyl)-5,7-dimethyl-4-(1H-1,2,4-triazol-1-yl)imidazo[5,1-f]-[1,2,4]triazine

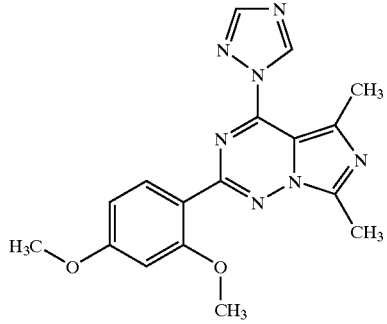

Preparation analogously to Example 37A starting from 410 mg (1.37 mmol) of Example 69A.

Yield: 290 mg (61%)

MS (ESI): m/z=352 [M+H]$^+$

Example 78A

2-[4-(Benzyloxy)phenyl]-5,7-dimethyl-4-(1H-1,2,4-triazol-1-yl)imidazo[5,1-f]-[1,2,4]triazine

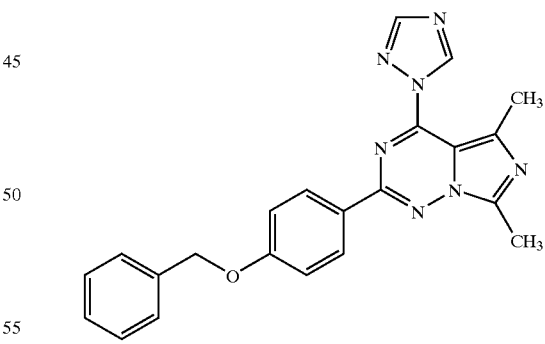

Preparation analogously to Example 37A starting from 2.25 g (6.50 mmol) of Example 70A.

Yield: 1.39 g (54%)

$^1$H-NMR (300 MHz, CDCl$_3$): δ=2.80 (s, 3H), 2.87 (s, 3H), 5.17 (s, 2H), 7.11 (d, 2H), 7.31–7.50 (m, 5H), 8.26 (s, 1H), 8.32 (d, 2H), 9.36 (s, 1H).

Example 79A

2-[4-(Benzyloxy)phenyl]-5,7-dimethyl-4-(3,4,5-trimethoxyphenoxy)imidazo[5,1-f]-[1,2,4]triazine

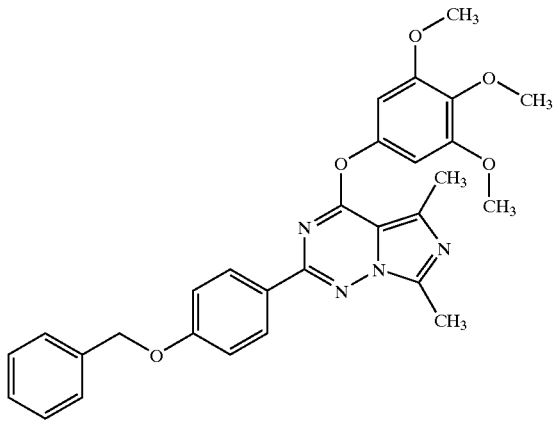

280 mg (2.45 mmol) of potassium tert-butoxide and 450 mg (2.45 mmol) of 3,4,5-trimethoxyphenol are stirred at room temperature for half an hour in 30 ml of THF. After addition of 650 mg (1.64 mmol) of Example 78A, the mixture is stirred under reflux for 2 h. The mixture is then concentrated from the solvent, extracted in dichloromethane/1N sodium hydroxide solution, and the organic phase is dried, concentrated in a rotary evaporator and flash chromatographed using dichloromethane/methanol 100/1.

Yield: 822 mg (98% of theory)

$^1$H-NMR (300 MHz, CDCl$_3$): δ=2.72 (s, 3H), 2.74 (s, 3H), 3.87 (s, 6H), 3.91 (s, 3H), 5.11 (s, 2H), 6.61 (s, 2H), 6.99 (d, 2H), 7.29–7.46 (m, 5H), 8.10 (d, 2H).

Example 80A

Ethyl 3-(acetylamino)-2-oxopentanoate

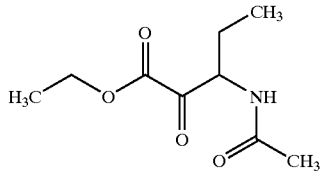

Preparation is carried out analogously to Example 6A by reaction of 4.35 g (30 mmol) of ethyl N-acetyl-2-aminobutanoate with 8.19 g (60 mmol) of ethyl oxalyl chloride and 7.12 g (90 mmol) of pyridine in tetrahydrofuran. The crude product is immediately reacted further.

Example 81A

N-{1-[3-(3,4-Dimethoxyphenyl)-5-oxo-4,5-dihydro-1,2,4-triazin-6-yl]propyl}-acetamide

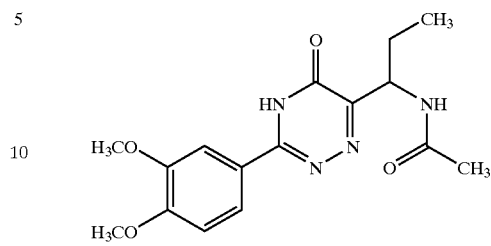

Preparation is carried out analogously to Example 11A by reaction of 4.0 g (18.5 mmol) of Example 1A, 1.11 g (22.2 mmol) of hydrazine hydrate and 5.57 g (27.7 mmol) of Example 80A.

Yield: 1.10 g (10% of theory)
LC-MS (ESI$^+$): R$_t$=2.48 min.
MS: m/z=355 [M+Na]$^+$

Example 82A 2-(3,4-Dimethoxyphenyl)-5-ethyl-7-methylimidazo[5,1-f][1,2,4]triazin-4(3H)-one

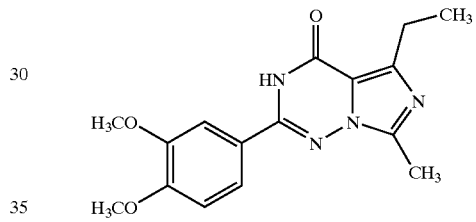

Preparation analogously to Example 26A by reaction of 1.10 g (3.3 mmol) of Example 81 A and 1.52 g (9.9 mmol) of phosphoryl chloride in 1,2-dichloroethane.

Yield: 187 mg (18% of theory)
LC-MS (LCMS8 min-centr): R$_t$=1.93 min.
MS: m/z=315 [M+H]$^+$

Example 83A 2-(3,4-Dimethoxyphenyl)-7-isopropyl-5-methylimidazo[5,1-f][1,2,4]triazin-4(3H)-one

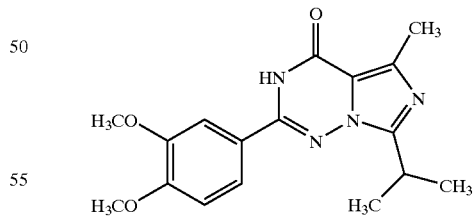

Preparation is carried out analogously to Example 63A by reaction of 1.11 g (4 mmol) of Example 12A with 639 mg (6 mmol) of isobutyryl chloride.

Yield: 1.03 g (75% of theory)
LC-MS (ESI+): R$_t$=3.61 min.
MS: m/z=329 [M+H]$^+$
$^1$H-NMR (300 MHz, DMSO-d$_6$): δ=1.31 (d, 6H), 2.47 (s, 3H), 3.49 (quint, 1H), 3.84 (s, 3H), 3.86 (s, 3H), 7.11 (d, 1H), 7.57 (d, 1H), 7.62 (dd, 1H), 11.69 (bs, 1H).

Example 84A 7-sec-Butyl-2-(3,4-dimethoxyphenyl)-5-methylimidazo[5,1-f][1,2,4]triazin-4(3H)-one

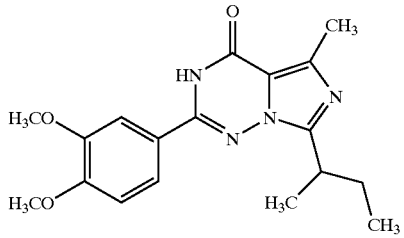

Preparation is carried out analogously to Example 63A by reaction of 600 mg (2.17 mmol) of Example 12A with 524 mg (4.34 mmol) of 2-methylbutyryl chloride.

Yield: 384 mg (51% of theory)
LC-MS (ESI$^+$): R$_t$=3.50 min.
MS: m/z=343 [M+H]$^+$
$^1$H-NMR (300 MHz, CDCl$_3$): δ=0.92 (t, 3H), 1.41 (d, 3H), 1.78 (m, 1H), 1.95 (m, 1H), 2.66 (s, 3H), 3.43 (sext, 1H), 3.98 (s, 3H), 4.00 (s, 3H), 6.99 (d, 1H), 7.45–7.51 (m, 2H), 9.6 (bs, 1H).

Example 85A 2-(3,4-Dimethoxyphenyl)-7-(1-ethylpropyl)-5-methylimidazo[5,1-f][1,2,4]triazin-4(3H)-one

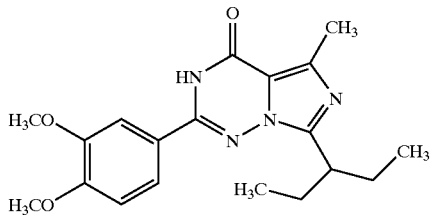

Preparation is carried out analogously to Example 63A by reaction of 600 mg (2.17 mmol) of Example 12A with 585 mg (4.34 mmol) of 2-ethylbutyryl chloride.

Yield: 432 mg (56% of theory)
LC-MS (ESI+): R$_t$=3.70 min.
MS: m/z=357 [M+H]$^+$
$^1$H-NMR (300 MHz, CDCl$_3$): δ=0.86 (t, 6H), 1.78–1.98 (m, 4H), 2.67 (s, 3H), 3.28 (m, 1H), 3.98 (s, 3H), 4.00 (s, 3H), 6.99 (d, 1H), 7.49 (d, 1H), 7.54 (dd, 1H), 9.55 (bs, 1H).

Example 86A 2-(3,4-Dimethoxyphenyl)-5-ethyl-7-methyl-4-(1H-1,2,4-triazol-1-yl)imidazo [5,1-f]-[1,2,4]triazine

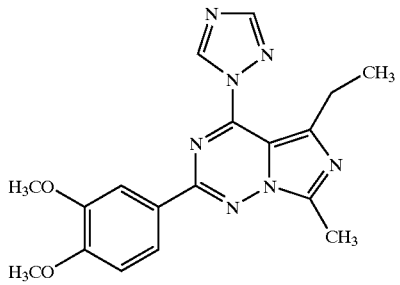

Preparation is carried out analogously to Example 37A from 186 mg (0.59 mmol) of Example 82A.

Yield: 189 mg (87% of theory)
LC-MS (ESI$^+$): R$_t$=3.92 min.
MS: m/z=366 [M+H]$^+$
$^1$H-NMR (200 MHz, DMSO-d$_6$): δ=1.19 (t, 3H), 2.73 (s, 3H), 3.17 (q, 2H), 3.85 (s, 3H), 3.90 (s, 3H), 7.12 (d, 1H), 7.88 (d, 1H), 8.04 (dd, 1H), 8.57 (s, 1H), 9.83 (s, 1H).

Example 87A 2-(3,4-Dimethoxyphenyl)-7-isopropyl-5-methyl-4-(1H-1,2,4-triazol-1-yl)imidazo-[5,1-f][1,2,4]triazine

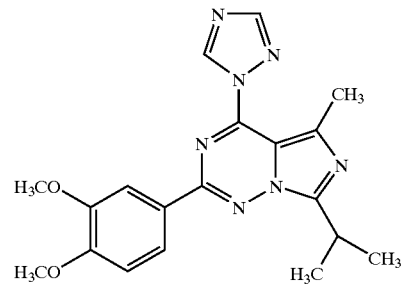

Preparation is carried out analogously to Example 37A from 128 mg of Example 83A.

Yield: 135 mg (91% of theory)
LC-MS (ESI$^+$): R$_t$=4.40 min.
MS: m/z=380 [M+H]$^+$
$^1$H-NMR (300 MHz, CDCl$_3$): δ=1.50 (d, 6H), 2.88 (s, 3H), 3.79 (sept, 1H), 3.99 (s, 3H), 4.01 (s, 3H), 7.0 (d, 1H), 7.88 (d, 1H), 8.00 (dd, 1H), 8.26 (s, 1H), 9.33 (s, 1H).

Example 88A 7-sec-Butyl-2-(3,4-dimethoxyphenyl)-5-methyl-4-(1H-1,2,4-triazol-1-yl)imidazo-[5,1-f][1,2,4]triazine

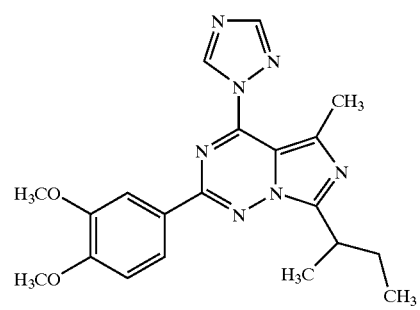

Preparation is carried out analogously to Example 37A from 360 mg (1.05 mmol) of Example 84A.

Yield: 262 mg (63% of theory)
LC-MS (ESI$^+$): R$_t$=4.70 min.
MS: m/z=394 [M+H]$^+$
$^1$H-NMR (500 MHz, CDCl$_3$): δ=0.95 (t, 3H), 1.49 (d, 3H), 1.87 (m, 1H), 2.04 (m, 1H), 2.88 (s, 3H), 3.62 (sext, 1H), 3.98 (s, 3H), 4.02 (s, 3H), 6.99 (d, 1H), 7.87 (d, 1H), 7.98 (dd, 1H), 8.27 (s, 1H), 9.35 (s, 1H).

Example 89A 2-(3,4-Dimethoxyphenyl)-7-(1-ethylpropyl)-5-methyl-4-(1H-1,2,4-triazol-1-yl)imidazo-[5,1-f][1,2,4]triazine

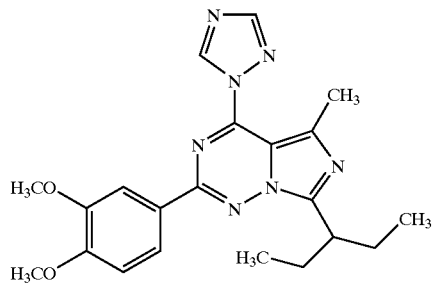

Preparation is carried out analogously to Example 37A from 415 mg (1.16 mmol) of Example 85A.

Yield: 428 mg (90% of theory)

LC-MS (ESI$^+$): $R_t$=4.80 min.

MS: m/z=408 [M+H]$^+$ $^1$H-NMR (300 MHz, CDCl$_3$): δ=0.88 (t, 6H), 1.85–2.10 (m, 4H), 2.89 (s, 3H), 3.50 (m, 1H), 3.99 (s, 3H), 4.02 (s, 3H), 7.00 (d, 1H), 7.88 (d, 1H), 7.99 (dd, 1H), 8.27 (s, 1H), 9.35 (s, 1H).

Example 55

N-[2-(3-Chlorophenyl)ethyl]-2-(2-ethoxyphenyl)-5-methyl-7-propylimidazo[5,1-f]-[1,2,4]triazin-4-amine

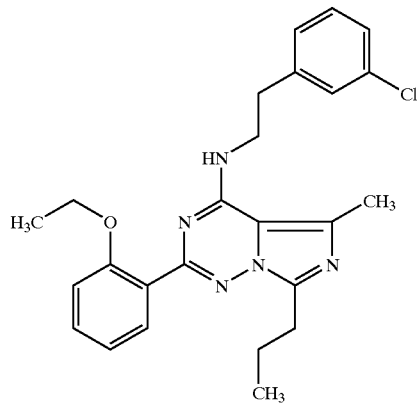

In a parallel synthetic run, 18.7 mg (0.12 mmol) of 2-(3-chlorophenyl)ethylamine are introduced into a reaction vessel and treated with 1,2-dichloroethane solutions of Example 39A and triethylamine. The amount added is 29.1 mg (0.08 mmol; solution: 0.08 mol/l) of Example 39A and 8.10 mg (0.08 mmol; solution: 0.08 mol/l) of triethylamine.

The batch is stirred at RT for 16 h, then 100 mg of scavenger N-methylisatoic anhydride polystyrene are added and it is stirred for a further 16 h. For work-up, the batch is added to a silica gel cartridge (500 mg of silica gel, filling volume 3 ml) and the product is eluted with dichloromethane/methanol 100/1. The substance is freed from the solvent in a vacuum centrifuge.

Yield: 13.4 mg (37% of theory)

LC-MS (ESI$^+$): Retention time=3.63 min., m/z=449 [M]$^+$

Example 56

2-(2-Ethoxyphenyl)-N-[2-(3-methoxyphenyl)ethyl]-5-methyl-7-propylimidazo[5,1-f]-[1,2,4]triazin-4-amine

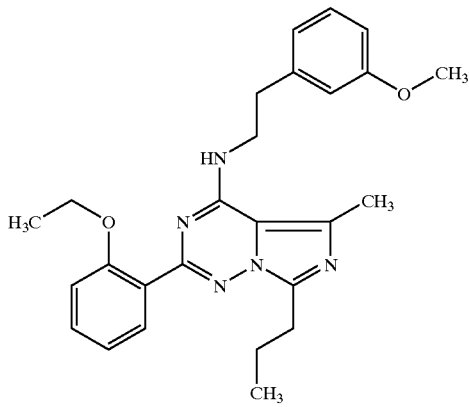

Analogously to Example 55, 18.3 mg (0.12 mmol) of 2-(3-methoxyphenyl)ethyl-amine are reacted with 29.4 mg (0.08 mmol) of Example 39A and 8.20 mg (0.08 mmol) of triethylamine.

Yield: 3.00 mg (5% of theory)

LC-MS (ESI$^+$): Retention time=3.39 min., m/z=445 [M]$^+$

Example 57

N-Benzyl-2-(4-bromophenyl)-5,7-dimethylimidazo[5,1-f][1,2,4]triazin-4-amine

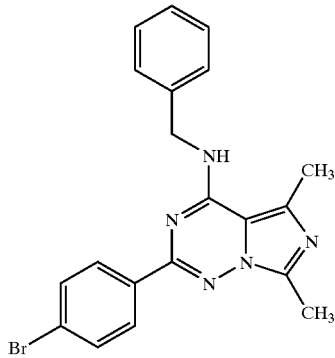

In a parallel synthetic run, 3.91 mg (0.04 mmol) of benzylamine were introduced into a reaction vessel and treated with dimethylformamide solutions of Example 50A and triethylamine. The amount added was 9.00 mg (0.02 mmol; solution: 0.03 mol/l) of Example 50A and 2.46 mg (0.02 mmol; solution: 0.12 mol/l) of triethylamine. The batch was stirred at RT for 24 h, then at 80° C. for a further 8 h. The reaction mixture was separated by means of a preparative HPLC unit.

Yield: 5.00 mg (34% of theory)

MS (DCI/NH$_3$): m/z=408 [M]$^+$

Example 58

2-(4-Bromophenyl)-N-(4-chlorobenzyl)-5,7-dimethylimidazo[5,1-f][1,2,4]triazin-4-amine

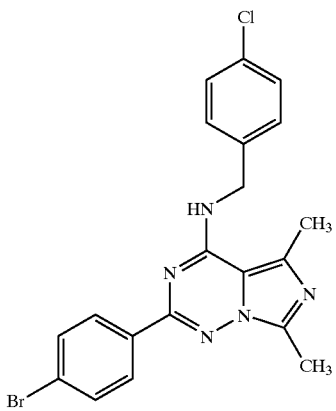

Analogously to Example 57, 5.24 mg (0.04 mmol) of 4-chlorobenzylamine are reacted with 9.26 mg (0.03 mmol) of Example 50A and 2.53 mg (0.03 mmol) of triethylamine.

Yield: 3.10 mg (28% of theory)

LC-MS (ESI$^+$): Retention time=3.93 min., m/z=441 [M]$^+$

Example 59

N-[2-(4-Bromophenyl)-5,7-dimethylimidazo[5,1-f][1,2,4]triazin-4-yl]-N-(4-methoxybenzyl)amine

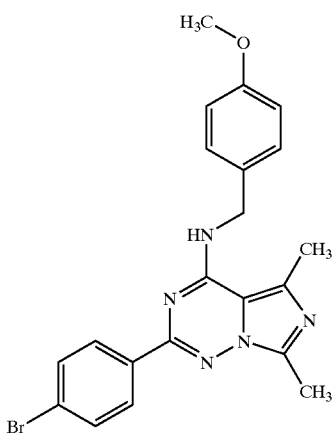

Analogously to Example 57, 7.13 mg (0.05 mmol) of 4-methoxybenzylamine are reacted with 9.63 mg (0.03 mmol) of Example 50A and 2.63 mg (0.03 mmol) of triethylamine.

Yield: 11.5 mg (quant.)

LC-MS (ESI$^+$): Retention time=3.55 min., m/z=437 [M]$^+$

Example 60

2-(4-Bromophenyl)-5,7-dimethyl-N-(2-pyridinylmethyl)imidazo[5,1-f][1,2,4]triazin-4-amine

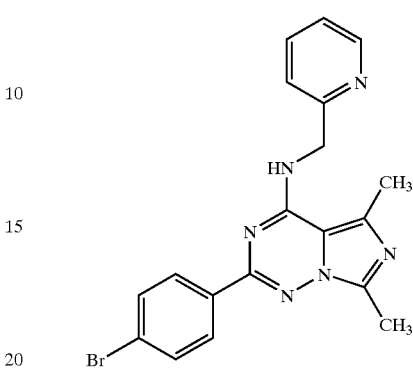

Analogously to Example 57, 5.30 mg (0.05 mmol) of 2-pyridinylmethanamine are reacted with 9.26 mg (0.03 mmol) of Example 50A and 2.53 mg (0.03 mmol) of triethylamine.

Yield: 5.90 mg (57.7% of theory, purity: 100%)

LC-MS (ESI$^+$): Retention time=2.81 min., m/z=408 [M]$^+$

Example 61

2-(4-Bromophenyl)-5,7-dimethyl-N-(3-pyridinylmethyl)imidazo[5,1-f][1,2,4]triazin-4-amine

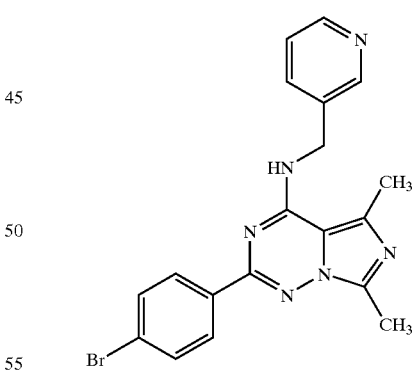

Analogously to Example 57, 5.41 mg (0.05 mmol) of 3-pyridinylmethylamine are reacted with 9.26 mg (0.03 mmol) of Example 50A and 2.53 mg (0.03 mmol) of triethylamine.

Yield: 16.3 mg (quant.)

LC-MS (ESI$^+$): Retention time=2.40 min., m/z=408 [M]$^+$

Example 62

2-(4-Bromophenyl)-5,7-dimethyl-N-(4-pyridinylmethyl)imidazo[5,1-f][1,2,4]triazin-4-amine

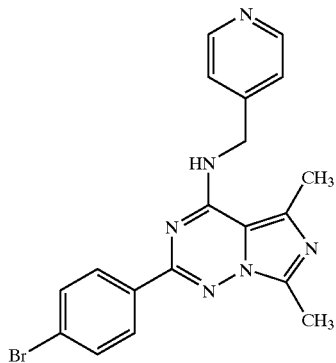

Analogously to Example 57, 5.73 mg (0.05 mmol) of 4-pyridinylmethylamine are reacted with 10.0 mg (0.03 mmol) of Example 50A and 2.73 mg (0.03 mmol) of triethylamine.

Yield: 3.7 mg (34% of theory)

LC-MS (ESI$^+$): Retention time=2.32 min., m/z=408 [M]$^+$

Example 63

4-[(1H-Benzimidazol-2-ylmethyl)sulphanyl]-2-(4-bromophenyl)-5,7-dimethyl-imidazo-[5,1-f][1,2,4]triazine

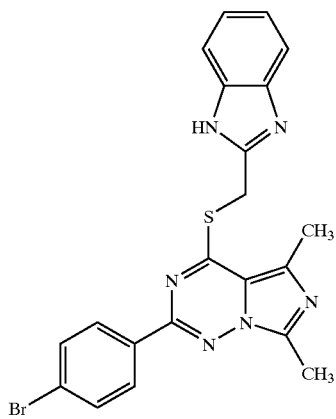

In a parallel synthetic run, 5.75 mg (0.04 mmol) of 1H-benzimidazol-2-ylmethylthiol are introduced into a reaction vessel and treated with dimethylformamide solutions of 8.51 mg (0.02 mmol; solution: 0.03 mol/l) of Example 50A and 2.63 mg (0.03 mmol; solution: 0.12 mol/l) of triethylamine. The mixture is then stirred at room temperature for 3 days. The reaction mixture is purified by means of a 500 mg silica gel cartridge and rinsed with ethyl acetate; then concentrated in a vacuum centrifuge.

Yield: 6.4 mg (57% of theory)

LC-MS (ESI$^+$): Retention time=2.99 min., m/z=464 [M]$^+$

Example 64

2-(3–Chloro-4-methoxyphenyl)-N-(4-methoxybenzyl)-5,7-dimethylimidazo[5,1-f]-[1,2,4]triazin-4-amine

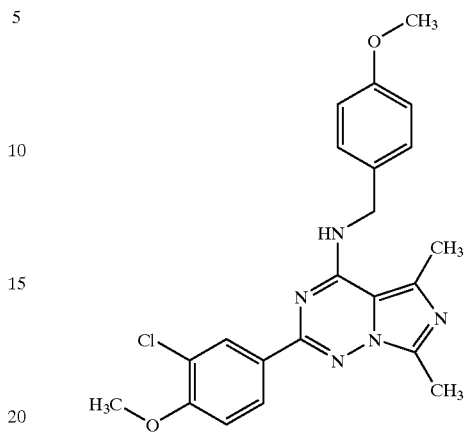

In a parallel synthetic run, 6.86 mg (0.05 mmol) of 4-methoxybenzylamine are introduced into a reaction vessel and treated with dimethylformamide solutions of 8.89 mg (0.03 mmol; solution: 0.05 mol/l) of Example 33A and 2.53 mg (0.03 mmol; solution: 0.13 mol/l) of triethylamine.

The batch is stirred at RT for 24 h, then at 60° C. for a further 4 h. The reaction mixture is separated by means of a preparative HPLC unit.

Yield: 1.2 mg (11% of theory)

LC-MS (ESI$^+$): Retention time=3.57 min., m/z=423 [M]$^+$

Example 65

N-[4-({[2-(4-Bromophenyl)-5,7-dimethylimidazo[5,1-f][1,2,4]triazin-4-yl]amino}-methyl)phenyl]acetamide

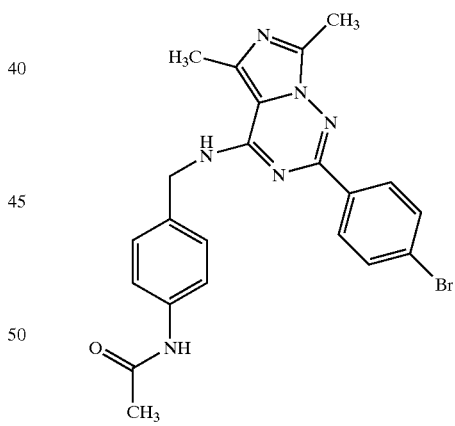

2-(4-Bromophenyl)-5,7-dimethyl-4-(1H-1,2,4-triazol-1-yl)imidazo[5,1-f][1,2,4]-triazine (3.7 mg, 10 mmol) is treated in dioxane (100 µl) with 4-acetylamino-benzylamine (3.3 mg, 20 mmol) and triethylamine (4 µl). The mixture is heated at 80° C. with shaking for 12 h, filtered and washed with DMSO (2×100 µl). The combined filtrates are purified chromatographically by preparative LC-MS.

LC-MS (LCMS8 min-centr)=488 [M+H]$^+$

R$_t$=4.11 min

The further examples shown in Table 1 are prepared from the appropriate starting materials in an analogous manner and characterized.

TABLE 1
| Example No. | Structure | R_t(min) | MS (m/z) [M + H]+ |
|---|---|---|---|
| 66 | 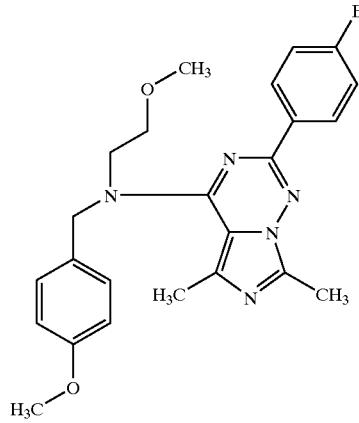 | 5.18 | 497 |
| 67 | 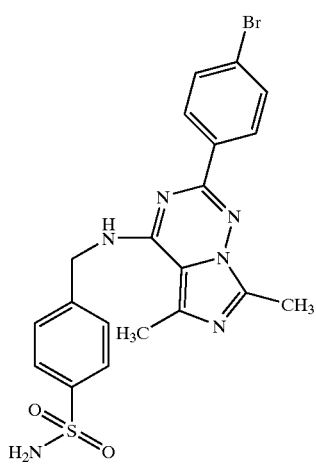 | 4.01 | 488 |
| 68 | 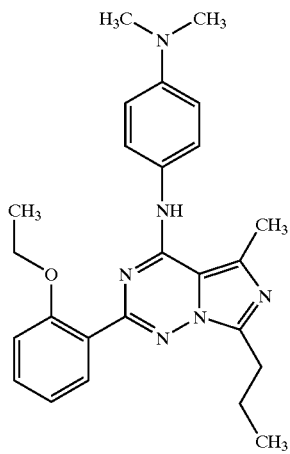 | 3.98 | 431 |

TABLE 1-continued

| Example No. | Structure | R_t(min) | MS (m/z) [M + H]+ |
|---|---|---|---|
| 69 | 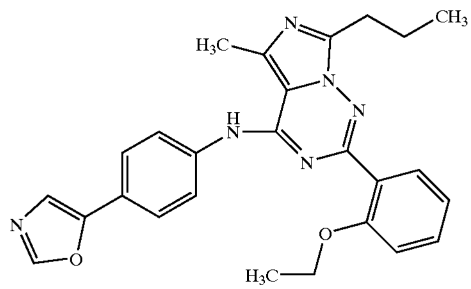 | 4.48 | 455 |
| 70 | 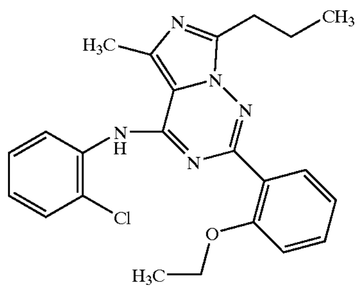 | [lacuna] | 422 |
| 71 | 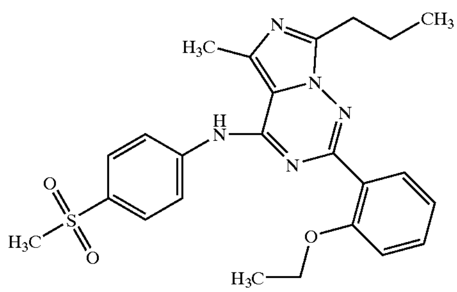 | 4.29 | 466 |
| 72 | 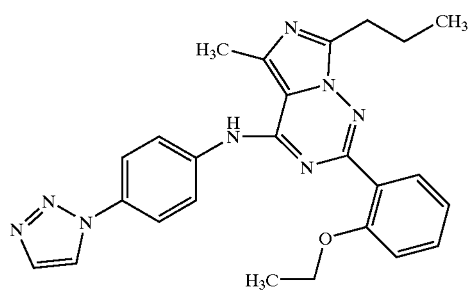 | 4.27 | 455 |
| 73 | 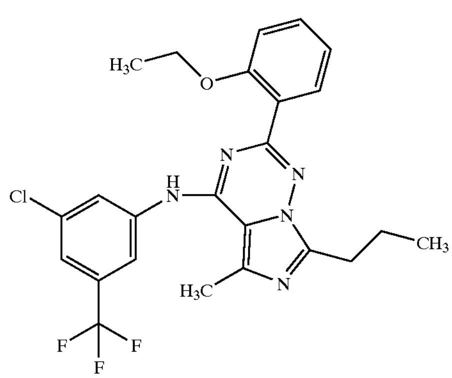 | 5.75 | 490 |

TABLE 1-continued

| Example No. | Structure | R$_t$(min) | MS (m/z) [M + H]$^+$ |
|---|---|---|---|
| 74 | 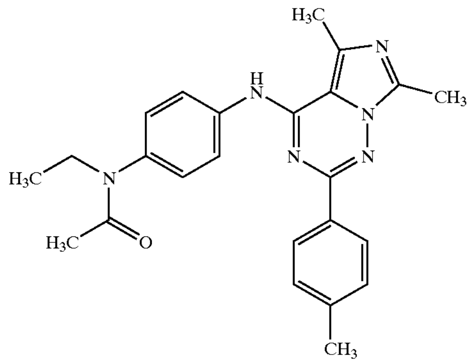 | 4.3 | 415 |
| 75 | 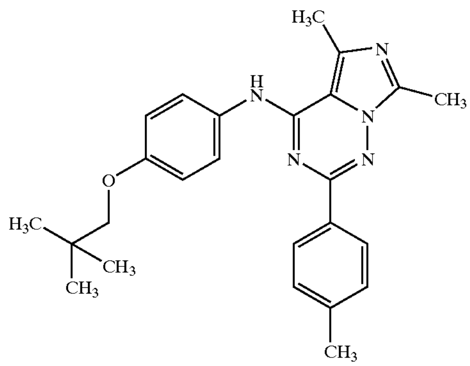 | 5.6 | 416 |
| 76 | 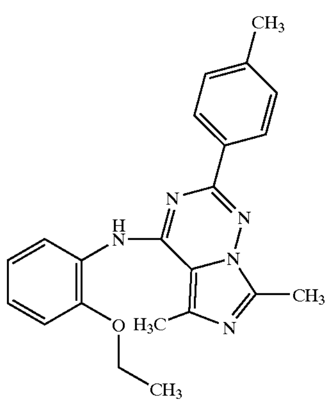 | 5.59 | 374 |
| 77 | 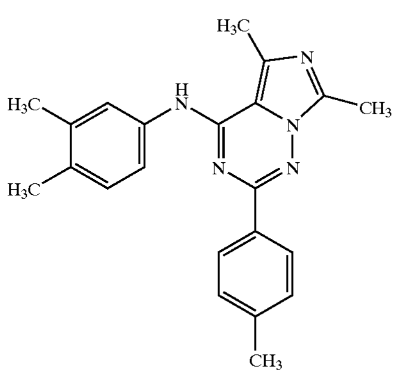 | 5.02 | 358 |

TABLE 1-continued
| Example No. | Structure | R$_t$(min) | MS (m/z) [M + H]$^+$ |
|---|---|---|---|
| 78 | 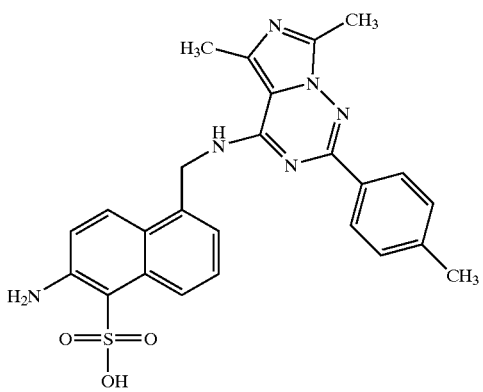 | 3.88 | 489 |
| 79 | 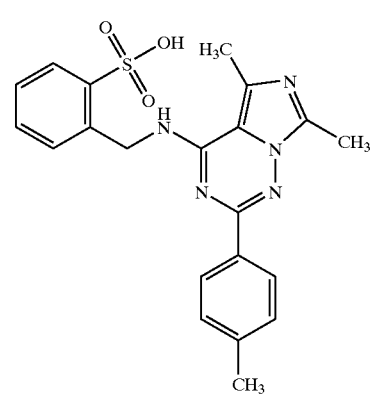 | 4.07 | 424 |
| 80 | 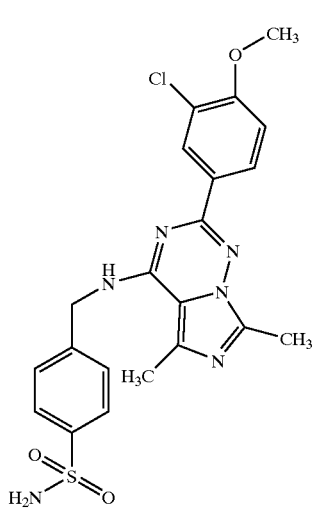 | 3.81 | 474 |

TABLE 1-continued

| Example No. | Structure | R_t(min) | MS (m/z) [M + H]+ |
|---|---|---|---|
| 81 | 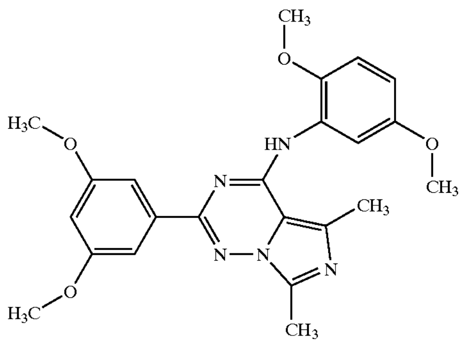 | 5.35 | 436 |
| 82 | 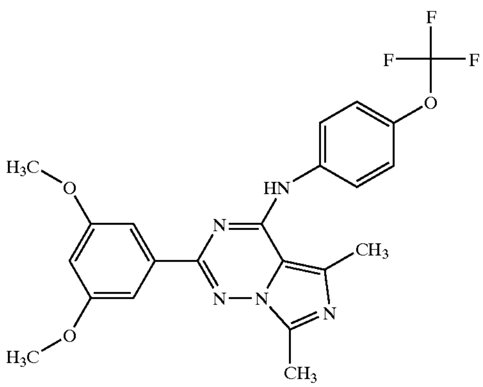 | 5.18 | 460 |
| 83 | 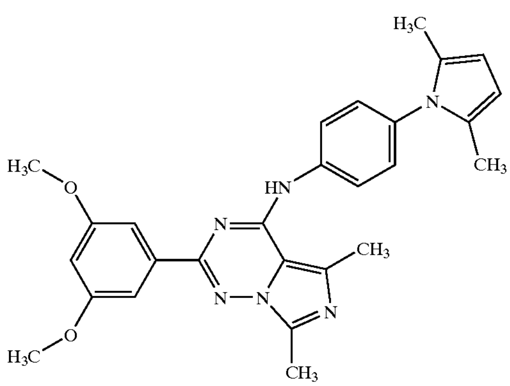 | 5.34 | 469 |
| 84 | 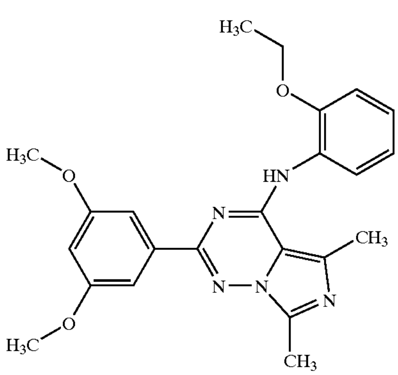 | 5.47 | 420 |

TABLE 1-continued

| Example No. | Structure | $R_t$(min) | MS (m/z) [M + H]⁺ |
|---|---|---|---|
| 85 | 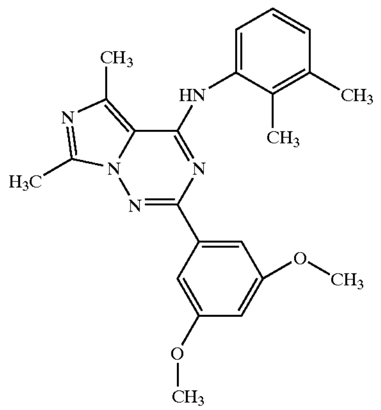 | 4.6 | 404 |
| 86 | 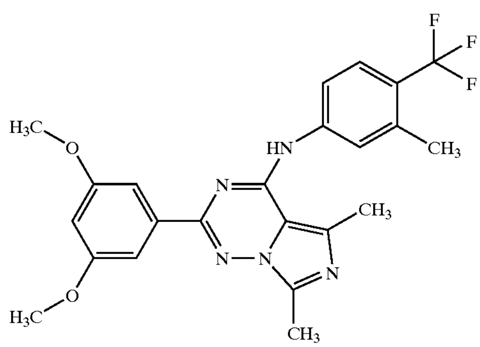 | 5.52 | 458 |

Example 87
5,7-Dimethyl-2-(4-methylphenyl)-4-(3,4,5-trimethoxyphenoxy)imidazo[5,1-f][1,2,4]-triazine

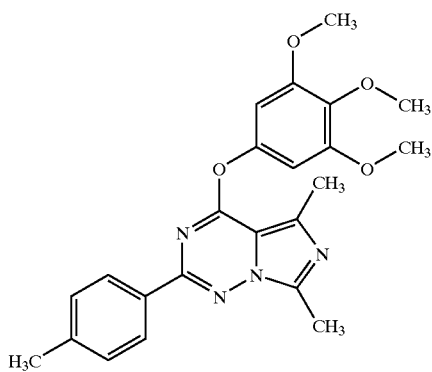

110 mg (0.98 mmol) of potassium tert-butoxide and 180 mg (0.98 mmol) of 3,4,5-trimethoxyphenol are stirred at room temperature for half an hour in 30 ml of THF. After addition of 200 mg (0.65 mmol) of Example 49A, the mixture is stirred under reflux for 2 h. It is then concentrated from the solvent, extracted in dichloromethane/1N sodium hydroxide solution, and the organic phase is dried, concentrated in a rotary evaporator and flash chromatographed using dichloromethane/methanol 100/1.

Yield: 264 mg (96% of theory)
MS (ESI): m/z=421 [M+H]⁺

¹H-NMR (200 MHz, CDCl₃): δ=2.39 (s, 3H), 2.73 (s, 3H), 2.76 (s, 3H), 3.88 (s, 6H), 3.91 (s, 3H), 6.63 (s, 2H), 7.21 (d, 2H), 8.06 (d, 2H).

Example 88
7-Isopropyl-5-methyl-2-(4-methylphenyl)-4-(3,4,5-trimethoxyphenoxy)imidazo-[5,1-f][1,2,4]triazine

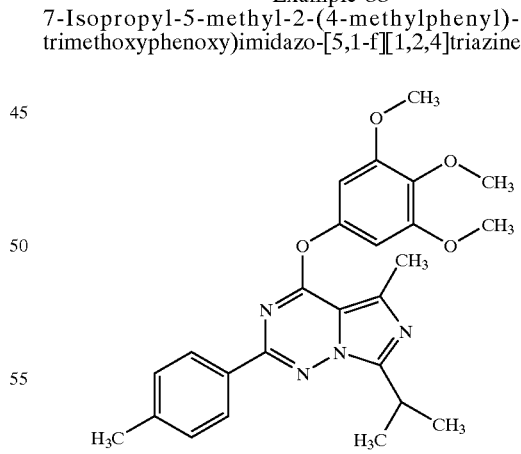

Analogously to Example 87, 84 mg (0.25 mmol) of Example 71A, 42.4 mg (0.38 mmol) of potassium tert-butoxide and 69.6 mg (0.38 mmol) of 3,4,5-trimethoxyphenol are reacted.

Yield: 86 mg (76% of theory)
MS (ESI): m/z=449 [M+H]⁺
¹H-NMR (400 MHz, CD₃OD): δ=1.46 (d, 6H), 2.36 (s, 3H), 2.70 (s, 3H), 3.71–3.79 (m, 1H), 3.83 (s, 3H), 3.85 (s, 6H), 6.75 (s, 2H), 7.21 (d, 2H), 8.00 (d, 2H).

Example 89

7-Isopropyl-5-methyl-2-(4-methylphenyl)-N-(3,4,5-trimethoxyphenyl)imidazo[5,1-f]-[1,2,4]triazin-4-amine

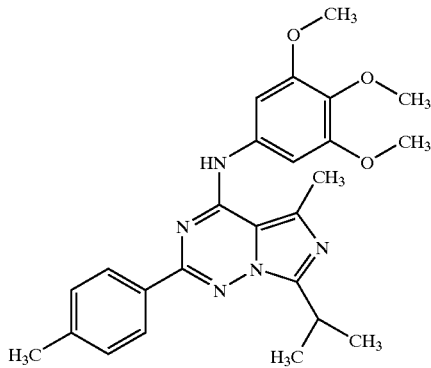

Analogously to Example 88, 750 mg (2.25 mmol) of Example 71A, 619 mg (3.37 mmol) of 3,4,5-trimethoxyaniline and 466 mg (3.37 mmol) of potassium carbonate are reacted. The product is flash chromatographed using cyclohexane/ethyl acetate 1/1.

Yield: 693 mg (69% of theory)

MS (ESI): m/z=448 [M+H]$^+$ $^1$H-NMR (300 MHz, CDCl$_3$): δ=1.47 (d, 6H), 2.42 (s, 3H), 2.80 (s, 3H), 3.71 (m, 1H), 3.88 (s, 3H), 3.94 (s, 6H), 7.05 (s, 1H), 7.16 (s, 2H), 7.24 (d, masked, 2H), 8.25 (d, 2H).

Example 90

7-sec-Butyl-5-methyl-2-(4-methylphenyl)-4-(3,4,5-trimethoxyphenoxy)imidazo-[5,1-f][1,2,4]triazine

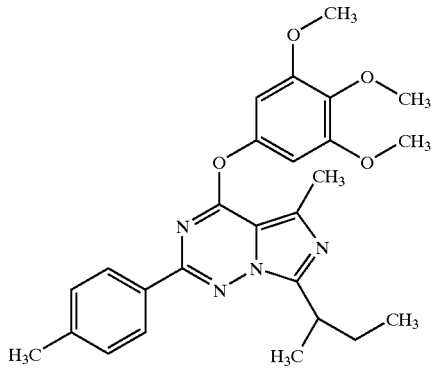

Analogously to Example 87, 100 mg (0.29 mmol) of Example 72A, 48.4 mg (0.43 mmol) of potassium tert-butoxide and 79.5 mg (0.43 mmol) of 3,4,5-trimethoxyphenol are reacted.

Yield: 55 mg (41% of theory)

MS (ESI): m/z=463 [M+H]$^+$ $^1$H-NMR (200 MHz, CDCl$_3$): δ=0.92 (t, 3H), 1.46 (d, 3H), 1.73–2.12 (m, 2H), 2.39 (s, 3H), 2.74 (s, 3H), 3.47–3.65 (m, 1H), 3.88 (s, 6H), 3.91 (s, 3H), 6.63 (s, 2H), 7.21 (d, 2H), 8.04 (d, 2H).

Example 91

7-sec-Butyl-5-methyl-2-(4-methylphenyl)-N-(3,4,5-trimethoxyphenyl)imidazo[5,1-f]-[1,2,4]triazin-4-amine

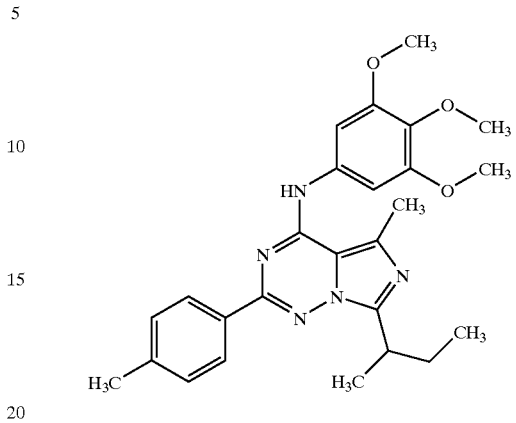

Analogously to Example 88, 216 mg (0.62 mmol) of Example 72A, 171 mg (0.93 mmol) of 3,4,5-trimethoxyaniline and 129 mg (0.93 mmol) of potassium carbonate are reacted.

Yield: 274 mg (95% of theory)

MS (ESI): m/z=462 [M+H]$^+$ $^1$H-NMR (200 MHz, CDCl$_3$): δ=0.92 (t, 3H), 1.44 (d, 3H), 1.72–2.09 (m, 2H), 2.42 (s, 3H), 2.81 (s, 3H), 3.48–3.63 (m, 1H), 3.89 (s, 3H), 3.95 (s, 6H), 7.06 (s, 1H), 7.16 (s, 2H), 7.25 (d, masked, 2H), 8.24 (d, 2H).

Example 92

7-(1-Ethylpropyl)-5-methyl-2-(4-methylphenyl)-4-(3,4,5-trimethoxyphenoxy)-imidazo[5,1-f][1,2,4]triazine

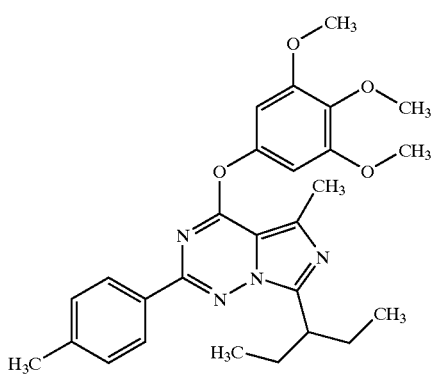

Analogously to Example 87, 200 mg (0.55 mmol) of Example 73A, 93.1 mg (0.83 mmol) of potassium tert-butoxide and 153 mg (0.83 mmol) of 3,4,5-trimethoxyphenol are reacted.

Yield: 213 mg (81% of theory)

MS (ESI): m/z=477 [M+H]$^+$ $^1$H-NMR (300 MHz, CD$_3$OD): δ=0.83 (t, 6H), 1.81–2.06 (m, 4H), 2.36 (s, 3H), 2.73 (s, 3H), 3.39–3.51 (m, 1H), 3.84 (s, 3H), 3.85 (s, 6H), 6.76 (s, 2H), 7.22 (d, 2H), 7.99 (d, 2H).

Example 93

7-(1-Ethylpropyl)-5-methyl-2-(4-methylphenyl)-N-(3,4,5-trimethoxyphenyl)imidazo-[5,1-f][1,2,4]triazin-4-amine

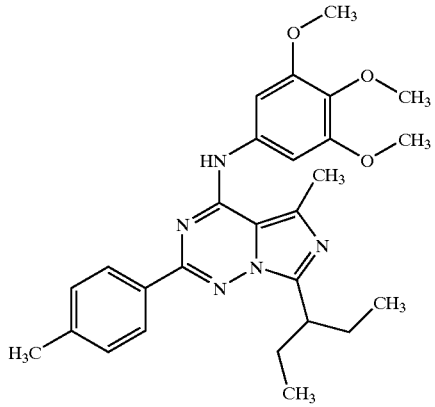

Analogously to Example 88, 209 mg (0.58 mmol) of Example 73A, 159 mg (0.87 mmol) of 3,4,5-trimethoxyaniline and 120 mg (0.87 mmol) of potassium carbonate are reacted. The compound is purified by HPLC separation.

Yield: 151 mg (55% of theory)

MS (ESI): m/z=476 [M+H]$^+$ $^1$H-NMR (300 MHz, CD$_3$OD): δ=0.83 (t, 6H), 1.79–2.06 (m, 4H), 2.40 (s, 3H), 2.78 (s, 3H), 3.37–3.48 (m, 1H), 3.81 (s, 3H), 3.91 (s, 6H), 7.26 (d, 2H), 7.33 (s, 2H), 8.18 (d, 2H).

Example 94

5,7-Dimethyl-2-(4-nitrophenyl)-4-(3,4,5-trimethoxyphenoxy)imidazo[5,1-f][1,2,4]-triazine

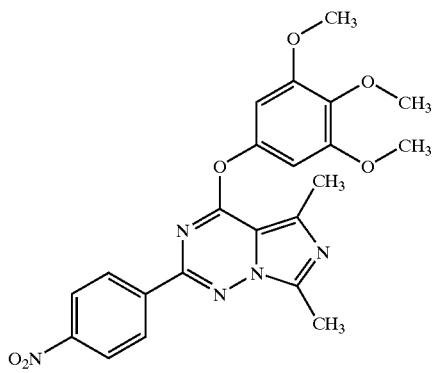

Analogously to Example 87, 75 mg (0.22 mmol) of Example 74A, 38 mg (0.33 mmol) of potassium tert-butoxide and 62 mg (0.33 mmol) of 3,4,5-trimethoxyphenol are reacted.

Yield: 76 mg (75% of theory)

MS (ESI): m/z=452 [M+H]$^+$ $^1$H-NMR (300 MHz, CDCl$_3$): δ=2.75 (s, 3H), 2.79 (s, 3H), 3.88 (s, 6H), 3.92 (s, 3H), 6.59 (s, 2H), 8.25 (d, 2H), 8.33 (d, 2H).

Example 95

5,7-Dimethyl-2-(4-nitrophenyl)-N-(3,4,5-trimethoxyphenyl)imidazo[5,1-f][1,2,4]-triazin-4-amine

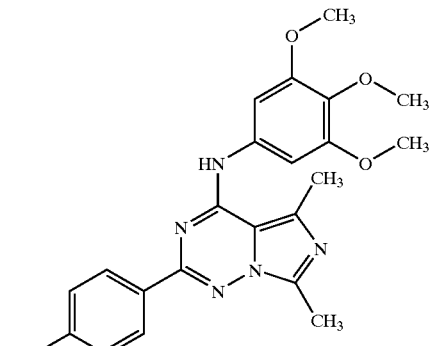

Analogously to Example 88, 75 mg (0.22 mmol) of Example 74A, 61 mg (0.34 mmol) of 3,4,5-trimethoxyaniline and 46 mg (0.34 mmol) of potassium carbonate are reacted. Yield: 52 mg (52% of theory)

MS (ESI): m/z=451 [M+H]$^+$ $^1$H-NMR (300 MHz, CD$_3$OD): δ=2.74 (s, 3H), 2.80 (s, 3H), 3.90 (s, 3H), 3.94 (s, 6H), 7.07 (s, 2H), 7.13 (s, 1H), 8.29 (d, 2H), 8.52 (d, 2H).

Example 96

2-(4-Methoxyphenyl)-5,7-dimethyl-4-(3,4,5-trimethoxyphenoxy)imidazo[5,1-f]-[1,2,4]triazine

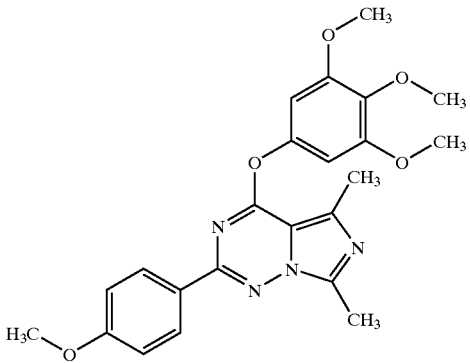

Analogously to Example 87, 260 mg (0.81 mmol) of Example 75A, 140 mg (1.21 mmol) of potassium tert-butoxide and 220 mg (1.21 mmol) of 3,4,5-trimethoxyphenol are reacted.

Yield: 294 mg (83% of theory)

MS (ESI): m/z=437 [M+H]$^+$ $^1$H-NMR (300 MHz, CD$_3$OD): δ=2.68 (s, 3H), 2.71 (s, 3H), 3.83 (s, 3H), 3.84 (s, 3H), 3.85 (s, 6H), 6.75 (s, 2H), 6.94 (d, 2H), 8.07 (d, 2H).

Example 97

2-(4-Methoxyphenyl)-5,7-dimethyl-N-(3,4,5-trimethoxyphenyl)imidazo[5,1-f]-[1,2,4]-triazin-4-amine

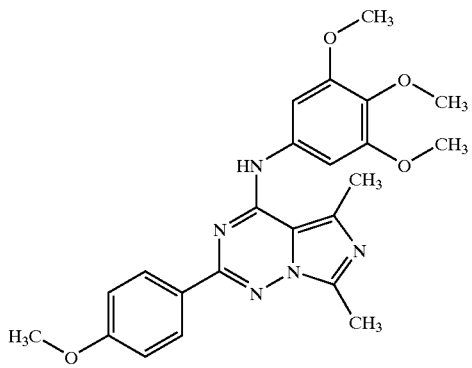

Analogously to Example 88, 260 mg (0.81 mmol) of Example 75A, 220 mg (1.21 mmol) of 3,4,5-trimethoxyaniline and 170 mg (1.21 mmol) of potassium carbonate are reacted. The product is obtained after washing by stirring with diethyl ether.

Yield: 158 mg (45% of theory)

MS (ESI): m/z=436 [M+H]$^+$ $^1$H-NMR (300 MHz, CD$_3$OD): δ=2.65 (s, 3H), 2.73 (s, 3H), 3.81 (s, 3H), 3.86 (s, 6H), 3.91 (s, 6H), 6.99 (d, 2H), 7.31 (s, 2H), 8.26 (d, 2H).

Example 98

7-Isopropyl-2-(4-methoxyphenyl)-5-methyl-4-(3,4,5-trimethoxyphenoxy)imidazo-[5,1-f][1,2,4]triazine

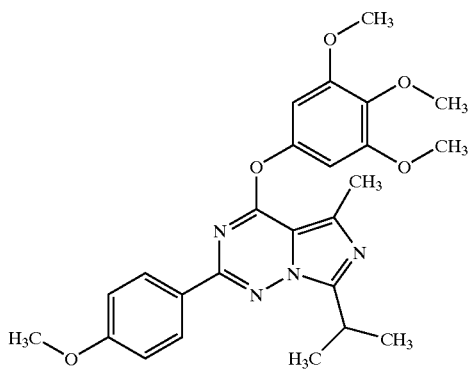

Analogously to Example 87, 146 mg (0.42 mmol) of Example 76A, 70 mg (0.63 mmol) of potassium tert-butoxide and 115 mg (0.63 mmol) of 3,4,5-trimethoxyphenol are reacted.

Yield: 91 mg (47% of theory)

MS (ESI): m/z=465 [M+H]$^+$ $^1$H-NMR (300 MHz, CDCl$_3$): δ=1.48 (d, 6H), 2.73 (s, 3H), 3.66–3.79 (m, 1H), 3.84 (s, 3H), 3.87 (s, 6H), 3.91 (s, 3H), 6.61 (s, 2H), 6.91 (d, 2H), 8.10 (d, 2H).

Example 99

7-Isopropyl-2-(4-methoxyphenyl)-5-methyl-N-(3,4,5-trimethoxyphenyl)imidazo-[5,1-f][1,2,4]triazin-4-amine

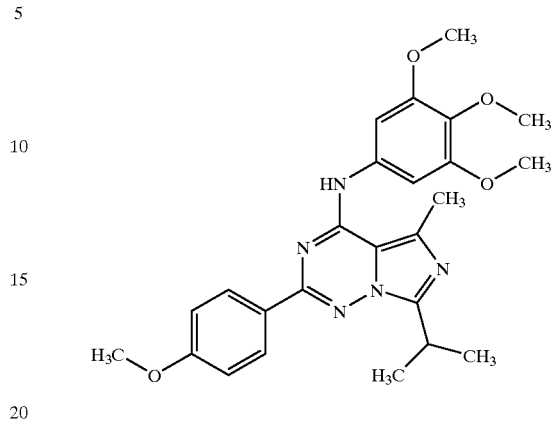

Analogously to Example 88, 70 mg (0.20 mmol) of Example 76A, 55 mg (0.30 mmol) of 3,4,5-trimethoxyaniline and 42 mg (0.30 mmol) of potassium carbonate are reacted. The product is obtained after washing by stirring with methanol.

Yield: 48 mg (52% of theory)

MS (ESI): m/z=464 [M+H]$^+$ $^1$H-NMR (200 MHz, CDCl$_3$): δ=1.46 (d, 6H), 2.80 (s, 3H), 3.62–3.79 (m, 1H), 3.88 (s, 3H), 3.89 (s, 3H), 3.95 (s, 6H), 6.96 (d, 2H), 7.05 (s, 1H), 7.14 (s, 2H); 8.30 (d, 2H).

Example 100

2-(2,4-Dimethoxyphenyl)-5,7-dimethyl-4-(3,4,5-trimethoxyphenoxy)imidazo[5,1-f]-[1,2,4]triazine

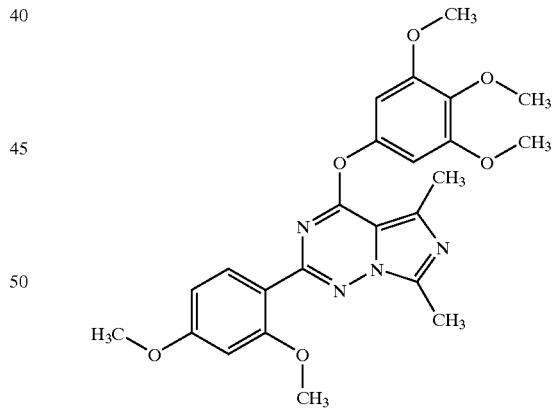

Analogously to Example 87, 125 mg (0.36 mmol) of Example 77A, 60 mg (0.53 mmol) of potassium tert-butoxide and 98 mg (0.53 mmol) of 3,4,5-trimethoxyphenol are reacted.

Yield: 150 mg (90% of theory)

MS (ESI): m/z=467 [M+H]$^+$ $^1$H-NMR (200 MHz, CD$_3$OD): δ=2.93 (s, 3H), 2.95 (s, 3H), 4.03 (s, 3H), 4.05 (s, 3H), 4.06–4.11 (s, 9H), 6.77–6.89 (m, 2H), 6.97 (s, 2H), 7.87 (d, 1H).

Example 101

2-(2-Ethoxyphenyl)-5-methyl-7-propyl-4-(3,4,5-trimethoxyphenoxy)imidazo[5,1-f]-[1,2,4]triazine

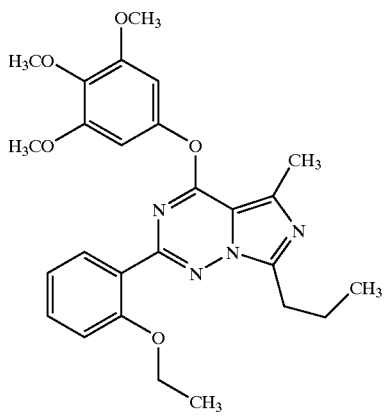

Preparation is carried out analogously to Example 22 from 500 mg (1.38 mmol) of Example 39A and 3,4,5-dimethoxyphenol.

Yield: 565 mg (85% of theory)

M.p.: 153° C.

MS (ESI+): m/z=479 [M+H]$^+$ $^1$H-NMR (300 MHz, DMSO-d$_6$): δ=0.95 (t, 3H), 1.23 (t, 3H), 1.8 (m, 2H), 2.65 (s, 3H), 2.98 (t, 2H), 3.65 (s, 3H), 3.74 (s, 6H), 4.0 (q, 2H), 6.78 (s, 2H), 6.92 (t, 1H), 7.09 (d, 1H), 7.35–7.55 (m, 2H)

Example 102

N-(3,4-Dimethoxyphenyl)-2-(2-ethoxyphenyl)-5-methyl-7-propylimidazo[5,1-f]-[1,2,4]triazin-4-amine

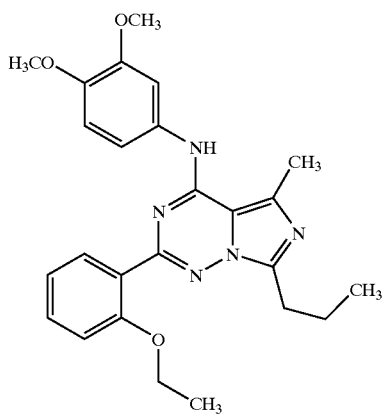

Preparation is carried out analogously to Example 1 from 500 mg (1.38 mmol) of Example 39A and 3,4-dimethoxyaniline.

Yield: 120 mg (19% of theory)

MS (ESI$^+$): m/z=448 [M+H]$^+$ $^1$H-NMR (300 MHz, DMSO-d$_6$): δ=0.93 (t, 3H), 1.28 (t, 3H), 1.8 (m, 2H), 2.7 (s, 3H), 2.9 (t, 2H), 3.72 (s, 3H), 3.74 (s, 3H), 4.07 (q, 2H), 6.92 (d, 1H), 6.98 (t, 1H), 7.1 (d, 1H), 7.3–7.6 (m, 4H), 8.62 (s, 1H)

Example 103

2-(2,4-Dimethoxyphenyl)-5,7-dimethyl-N-(3,4,5-trimethoxyphenyl)imidazo[5,1-f]-[1,2,4]triazin-4-amine

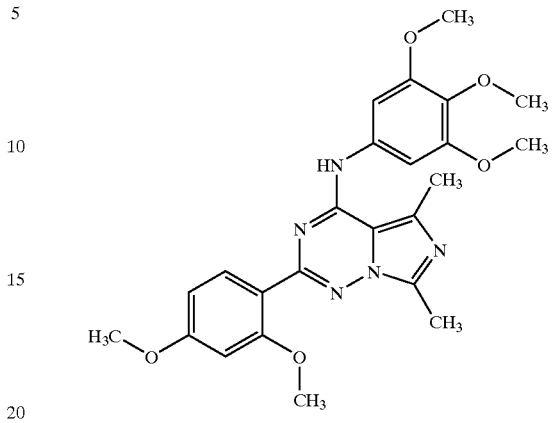

Analogously to Example 88, 140 mg (0.40 mmol) of Example 77A, 110 mg (0.60 mmol) of 3,4,5-trimethoxyaniline and 83 mg (0.60 mmol) of potassium carbonate are reacted. The product is purified by HPLC separation.

Yield: 48 mg (26% of theory)

MS (ESI): m/z=466 [M+H]$^+$ $^1$H-NMR (200 MHz, DMSO-d$_6$): δ=ca. 2.52 (s, masked, 3H), 2.69 (s, 3H), 3.64 (s, 3H), 3.76 (s, 6H), 3.78 (s, 3H), 3.81 (s, 3H), 6.60 (d, 1H), 6.65 (s, 1H), 7.29 (s, 2H); 7.57 (d, 1H), 8.64 (s, 1H).

Example 104

4-[5,7-Dimethyl-4-(3,4,5-trimethoxyphenoxy)imidazo[5,1-f][1,2,4]triazin-2-yl]-phenol

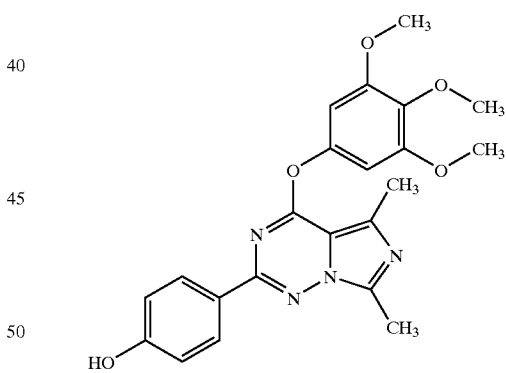

730 mg (1.42 mmol) of Example 79A are dissolved in 250 ml of methanol in a pear-shaped hydrogenating flask under an argon atmosphere. After the addition of 200 mg of 10% strength palladium on carbon, the reaction mixture is shaken at room temperature in a Parr apparatus for 96 h at a hydrogen pressure of 3 bar. Following this, the hydrogenation catalyst is separated off through a Seitz filter, and the solution is concentrated and flash-chromatographed using dichloromethane/methanol 50/1.

Yield: 297 mg (49% of theory)

MS (ESI): m/z=423 [M+H]$^+$ $^1$H-NMR (200 MHz, DMSO-d$_6$): δ=2.61 (s, 3H), 2.64 (s, 3H), 3.71 (s, 3H), 3.78 (s, 6H), 6.78–6.87 (m, 4H), 7.90 (d, 2H), 10.4 (s br, 1H).

Example 105

2-(3,4-Dimethoxyphenyl)-5-ethyl-7-methyl-N-(3,4,5-trimethoxyphenyl)imidazo-[5,1-f][1,2,4]triazin-4-amine

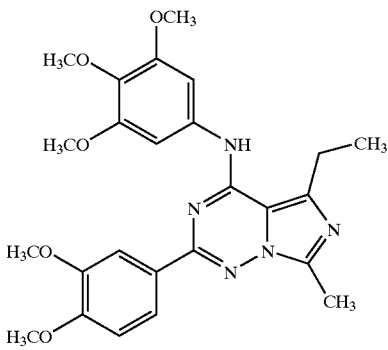

Preparation is carried out analogously to Example 88 from 80 mg (0.22 mmol) of Example 86A.

Yield: 66 mg (63% of theory)

LC-MS (ESI$^+$): $R_t$=3.55 min.

MS: m/z=480 [M+H]$^+$ $^1$H-NMR (200 MHz, DMSO-d$_6$): δ=1.29 (t, 3H), 2.62 (s, 3H), 3.12 (q, 2H), 3.70 (s, 3H), 3.78 (s, 3H), 3.81 (s, 9H), 7.08 (d, 1H), 7.19 (s, 2H), 7.77 (d, 1H), 7.85 (dd, 1H), 8.76 (bs, 1H).

Example 106

2-(3,4-Dimethoxyphenyl)-5-ethyl-7-methyl-4-(3,4,5-trimethoxyphenoxy)imidazo-[5,1-f][1,2,4]triazine

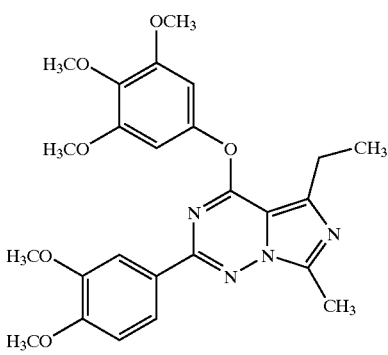

Preparation is carried out analogously to Example 87 from 80 mg (0.22 mmol) of Example 86A.

Yield: 69 mg (66% of theory)

LC-MS (ESI$^+$): $R_t$=4.28 min.

MS: m/z=481 [M+H]$^+$ $^1$H-NMR (200 MHz, DMSO-d$_6$): δ=1.34 (t, 3H), 2.69 (s, 3H), 3.01 (q, 2H), 3.70 (s, 3H), 3.71 (s, 3H), 3.79 (s, 6H), 3.80 (s, 3H), 6.84 (s, 2H), 7.08 (d, 1H), 7.60 (d, 1H), 7.66 (dd, 1H).

Example 107

2-(3,4-Dimethoxyphenyl)-7-isopropyl-5-methyl-N-(3,4,5-trimethoxyphenyl)imidazo-[5,1-f][1,2,4]triazin-4-amine

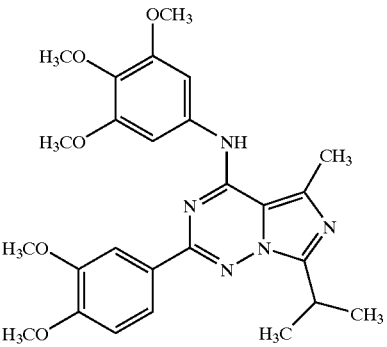

Preparation is carried out analogously to Example 88 from 60 mg (0.16 mmol) of Example 87A.

Yield: 62 mg (79% of theory)

LC-MS (ESI$^+$): $R_t$=4.20 min.

MS: m/z=494 [M+H]$^+$ $^1$H-NMR (200 MHz, CDCl$_3$): δ=1.49 (d, 6H), 2.80 (s, 3H), 3.72 (quint, 1H), 3.89 (s, 3H), 3.94 (s, 6H), 3.96 (s, 3H), 3.97 (s, 3H), 6.91 (d, 1H), 7.05 (bs, 1H), 7.09 (s, 2H), 7.88 (d, 1H), 7.98 (dd, 1H).

Example 108

7-sec-Butyl-2-(3,4-dimethoxyphenyl)-5-methyl-N-(3,4,5-trimethoxyphenyl)imidazo-[5,1-f][1,2,4]triazin-4-amine

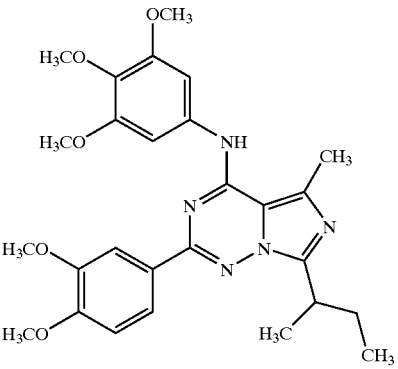

Preparation is carried out analogously to Example 88 from 50 mg (0.13 mmol) of Example 88A.

Yield: 41 mg (64% of theory)

LC-MS (ESI$^+$): $R_t$=4.28 min.

MS: m/z=508 [M+H]$^+$ $^1$H-NMR (300 MHz, CDCl$_3$): δ=0.93 (t, 3H), 1.50 (d, 3H), 1.86 (m, 1H), 2.04 (m, 1H), 2.89 (s, 3H), 3.61 (m, 1H), 3.89 (3H), 3.92 (s, 6H), 3.95 (s, 3H), 3.96 (s, 3H), 3.92 (d, 1H), 7.11 (s, 2H), 7.86 (d, 1H), 7.97 (dd, 1H).

Example 109

7-sec-Butyl-2-(3,4-dimethoxyphenyl)-5-methyl-4-(3,4,5-trimethoxyphenoxy)-imidazo[5,1-f][1,2,4]triazine

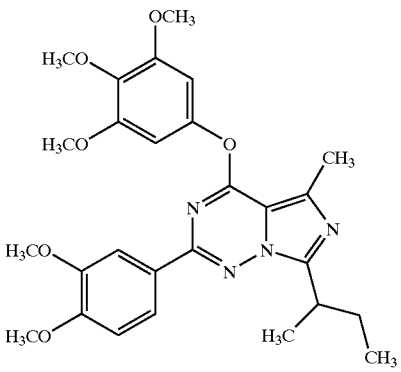

Preparation is carried out analogously to Example 87 from 50 mg (0.13 mmol) of Example 88A.

Yield: 51 mg (79% of theory)

LC-MS (ESI$^+$): $R_t$=5.01 min.

MS: m/z=509 [M+H]$^+$ $^1$H-NMR (300 MHz, CDCl$_3$): δ=0.94 (t, 3H), 1.52 (d, 3H), 1.39 (m, 1H), 2.06 (m, 1H), 2.80 (s, 3H), 3.62 (m, 1H), 3.88 (s, 3H), 3.89 (s, 6H), 3.90 (s, 3H), 3.92 (s, 3H), 6.60 (s, 2H), 6.89 (d, 1H), 7.69 (d, 1H), 7.78 (dd, 1H).

Example 110

2-(3,4-Dimethoxyphenyl)-7-(1-ethylpropyl)-5-methyl-N-(3,4,5-trimethoxyphenyl)-imidazo[5,1-f][1,2,4]triazin-4-amine

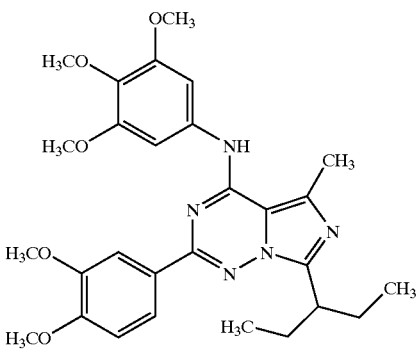

Preparation is carried out analogously to Example 88 from 60 mg (0.15 mmol) of Example 89A.

Yield: 48 mg (62% of theory)

LC-MS (ESI$^+$): $R_t$=4.39 min.

MS: m/z=522 [M+H]$^+$ $^1$H-NMR (200 MHz, CDCl$_3$): δ=0.87 (t, 6H), 1.78–2.10 (m, 4H), 2.81 (s, 3H), 3.39 (m, 1H), 3.89 (s, 3H), 3.93 (s, 6H), 3.95 (s, 3H), 3.96 (s, 3H), 6.92 (d, 1H), 7.04 (bs, 1H), 7.09 (s, 2H), 7.89 (d, 1H), 7.97 (dd, 1H).

Example 111

2-(3,4-Dimethoxyphenyl)-7-(1-ethylpropyl)-5-methyl-4-(3,4,5-trimethoxyphenoxy)-imidazo[5,1-f][1,2,4]triazine

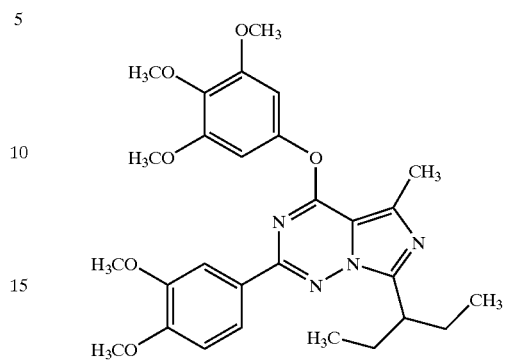

Preparation is carried out analogously to Example 87 from 60 mg (0.15 mmol) of Example 89A.

Yield: 54 mg (70% of theory)

LC-MS (ESI$^+$): $R_t$=5.10 min.

MS: m/z=523 [M+H]$^+$ $^1$H-NMR (300 MHz, CDCl$_3$): δ=0.88 (t, 6H), 1.85–2.10 (m, 4H), 2.79 (s, 3H), 3.85 (s, 3H), 3.88 (s, 6H), 3.90 (s, 3H), 3.92 (s, 3H), 6.62 (s, 2H), 6.89 (d, 1H), 7.70 (d, 1H), 7.78 (dd, 1H).

Method: ESI$^+$:

| Method: | MHZ 2T |
|---|---|
| Version No.: | 3 |
| Apparatus type MS: | Micromass TOF-MUX-Interface 4-fold parallel injection |
| | Ionization: ESI positive |
| Apparatus type HPLC: | Waters600 |
| | UV detector: 210 nm |
| | Oven temp.: 24° C. |
| Column: | Symmetry C 18 |
| | 50 mm × 2.1 mm 3.5 μm |
| Supply Company: | Waters |

| Gradient: | time (min) | A (vol %) | B (vol %) | flow (ml/min) |
|---|---|---|---|---|
| | 0.00 | 10 | 90 | 0.75 |
| | 0.50 | 10 | 90 | 0.75 |
| | 4.00 | 90 | 10 | 0.50 |
| | 5.50 | 90 | 10 | 0.75 |
| | 5.60 | 10 | 90 | 1.25 |
| | 6.50 | 10 | 90 | 0.75 |

A: CH$_3$CN + 0.1% formic acid
B: H$_2$O + 0.1% formic acid

Method 1:

Solution A: Acetonitrile
Solution B: 0.23 g of 30% HCl/l of water
Column oven 70° C.;
Column Symmetry C18 2.1 × 150 mm

| Gradient: | time [min] | % A | % B | flow [ml/min] |
|---|---|---|---|---|
| | 0 | 2 | 98 | 0.9 |
| | 2.5 | 95 | 5 | 1.2 |
| | 5 | 95 | 5 | 1.2 |

Method: LCMS8min_centr

| Method: | LCMS8min_centr | | | |
|---|---|---|---|---|
| Apparatus type MS: | TOF MS (LCT micromass) ionization: ESI positive | | | |
| Apparatus type HPLC: | Waters Alliance 2690 HPLC pump UF detector: 210 nm oven temperature: 40° C. | | | |
| Column: | YMC ODS-AQ 50 mm × 2.0 mm, 3 mm | | | |
| Gradient: | time (min) | A (vol %) | B (vol %) | flow (ml/min) |
| | 0.00 | 100 | 0 | 0.80 |
| | 0.30 | 100 | 0 | 0.80 |
| | 4.20 | 30 | 70 | 0.80 |
| | 4.80 | 10 | 90 | 0.80 |
| | 6.30 | 10 | 90 | 0.80 |
| | 6.31 | 100 | 0 | 0.80 |
| | 8.30 | 100 | 0 | 0.80 |

A: $H_2O$ (+0.1% $HCO_2H$)
B: $CH_3CN$ (+0.1% $HCO_2H$)

What is claimed is:

1. A compound of general formula (I),

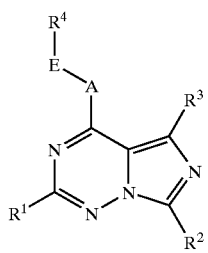

(I)

in which $R^1$ represents $(C_6-C_{10})$-aryl, which is optionally identically or differently substituted by radicals selected from the group consisting of halogen, formyl, carbamoyl, cyano, hydroxyl, trifluoromethyl, trifluoromethoxy, nitro, $(C_1-C_6)$-alkyl or $(C_1-C_6)$-alkoxy, and optionally by a radical of the formula $—SO_2NR^5R^6$, in which $R^5$ and $R^6$ independently of one another denote hydrogen or $(C_1-C_6)$-alkyl, or $NR^5R^6$ denotes 4- to 8-membered heterocyclyl, bonded via a nitrogen atom, optionally identically or differently substituted by radicals selected from the group consisting of oxo, halogen, $(C_1-C_6)$-alkyl and $(C_1-C_6)$-acyl, $R^2$ represents a saturated or partially unsaturated hydrocarbon radical having 1 to 10 carbon atoms, $R^3$ represents methyl or ethyl, A represents O, S or $NR^7$, in which $R^7$ denotes hydrogen or $(C_1-C_6)$-alkyl optionally substituted by $(C_1-C_3)$-alkoxy, E represents a bond or $(C_1-C_3)$-alkanediyl, $R^4$ represents $(C_6-C_{10})$-aryl or 5- to 10-membered heteroaryl, where aryl and heteroaryl are optionally identically or differently substituted by radicals selected from the group consisting of halogen, formyl, carboxyl, carbamoyl, $—SO_3H$, aminosulphonyl, cyano, hydroxyl, trifluoromethyl, trifluoromethoxy, nitro,
$(C_1-C_6)$-alkyl, $(C_1-C_6)$-alkoxy, 1,3-dioxa-propane-1,3-diyl, $(C_1-C_6)$-alkylthio, $(C_1-C_6)$-alkylsulphinyl and $(C_1-C_6)$-alkyl-sulphonyl, $—NR^8R^9$ end optionally methyl-substituted, 5- to 6-membered heteroaryl or phenyl, in which $R^8$ and $R^9$ independently of one another denote hydrogen, $(C_1-C_6)$-alkyl or $(C_1-C_6)$-acyl, or salt thereof.

2. The compound according to claim 1, where $R^1$ represents phenyl, which is optionally identically or differently mono- or disubstituted by radicals selected from the group consisting of fluorine, chlorine, methoxy, ethoxy or a radical of the formula $—SO_2NR^5R^6$, where $NR^5R^6$ is 5- to 7-membered heterocyclyl bonded via a nitrogen atom, $R^2$ represents $(C_1-C_8)$-alkyl or $(C_3-C_8)$-cycloalkyl, $R^3$ represents methyl or ethyl, A represents O or NH, E represents a bond, $R^4$ represents phenyl, which is optionally identically or differently substituted by radicals selected from the group consisting of fluorine, chlorine, methoxy or ethoxy, or salt thereof.

3. Process for the preparation of a compound according to claim 1, wherein a compound of formula (VI)

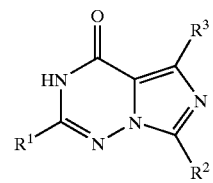

(VI)

in which $R^1$, $R^2$ and $R^3$ have the meaning indicated in claim 1, is reacted with 1,2,4-triazole in the presence of a chlorinating agent, optionally in inert solvents and optionally in the presence of a base, to give a compound of formula (II),

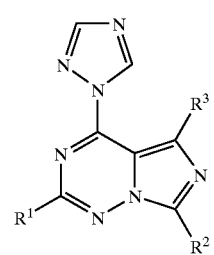

(II)

in which

R$^1$, R$^2$ and R$^3$ have the meaning indicated above, and subsequently reacted with a compound of formula (III),

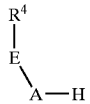
(III)

in which

R$^4$, A and E have the meaning indicated in claim 1, optionally in inert solvents, optionally in the presence of a base, optionally in the presence of auxiliary reagents, and optionally in the presence of crown ethers, or if A represents S, is reacted firstly with phosphorus pentasulphide or Lawesson's reagent, optionally in inert solvents, to give a compound of formula (IV),

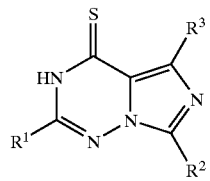
(IV)

in which

R$^1$, R$^2$ and R$^3$ have the meaning indicated above, and subsequently with a compound of formula (V),

(V)

in which

R$^4$ and E have the meaning indicated above, and

X$^1$ represents a leaving group or halogen, in inert solvents, optionally in the presence of a base.

4. Medicaments comprising at least one of the compounds of the general formula (I) according to claim 1 or 2 in admixture with at least one pharmaceutically tolerable, essentially non-toxic vehicle or excipient.

5. A method for the treatment of Parkinson's disease comprising administering to a subject a pharmaceutically effective amount of a compound of claim 1 or 2.

6. The process of claim 3, wherein the leaving group is mesylate or tosylate.

7. The process of claim 3, wherein the halogen is bromine or iodine.

* * * * *